US006458998B1

(12) United States Patent
Spevak et al.

(10) Patent No.: US 6,458,998 B1
(45) Date of Patent: Oct. 1, 2002

(54) NAPHTHALENE UREAS AS GLUCOSE UPTAKE ENHANCERS

(75) Inventors: Wayne R. Spevak, Albany; Songyuan Shi, Fremont; Prasad V. V. S. V. Manchem, South San Francisco; Michael R. Kozlowski, Palo Alto; Steven R. Schow, Redwood Shores; Robert T. Lum, Palo Alto, all of CA (US)

(73) Assignee: Telik, Inc., South San Francisco, CA (US)

( * ) Notice: Subject to any disclaimer, the term of this patent is extended or adjusted under 35 U.S.C. 154(b) by 0 days.

(21) Appl. No.: 09/579,279

(22) Filed: May 25, 2000

Related U.S. Application Data

(60) Provisional application No. 60/136,128, filed on May 26, 1999.

(51) Int. Cl.[7] .............................................. C07C 273/00
(52) U.S. Cl. ............................ 564/55; 564/48; 564/49; 564/50; 564/52; 514/596; 435/14
(58) Field of Search .............................. 564/55, 49, 50, 564/52, 48; 514/596; 435/14

(56) References Cited

U.S. PATENT DOCUMENTS

| | | | | |
|---|---|---|---|---|
| 3,716,368 A | * | 2/1973 | Froelich et al. ................. 96/99 |
| 4,051,176 A | * | 9/1977 | Bernstein et al. ........... 260/506 |
| 4,102,917 A | * | 7/1978 | Conrow et al. .............. 260/506 |
| 4,118,232 A | * | 10/1978 | Piller et al. ..................... 96/99 |
| 4,120,891 A | * | 10/1978 | Poletto et al. ............... 260/506 |
| 4,129,591 A | * | 12/1978 | Bernstein et al. ........... 260/506 |
| 4,132,730 A | * | 1/1979 | Conrow et al. .............. 260/506 |
| 4,591,604 A | * | 5/1986 | Conrow et al. |
| 5,830,918 A | * | 11/1998 | Sportsman et al. |

FOREIGN PATENT DOCUMENTS

| | | | |
|---|---|---|---|
| DE | 2216592 | * | 10/1972 |
| DE | 19521589 | * | 12/1996 |
| FR | 1578556 | * | 8/1969 |
| JP | 58-191772 | * | 11/1983 |
| WO | 98/32017 | * | 7/1998 |
| WO | 98/50347 | * | 11/1998 |

OTHER PUBLICATIONS

WO 98/50347. Kenyon et al. (1998). Naphthols useful in antiviral methods.*
Suramin sodium. The Merck Index, Tenth Edition, Merck & Co., Inc. Rahway, N.J. USA, 1983, p. 1294.*
STN, CAPLUS accession No. 1988:436172, XP002151699 abstract, and Ya. Ya. Aleksandrovskii: Vopr. Med. Khim. vol. 34, No. 3, 1988, pp. 7–15.*

* cited by examiner

Primary Examiner—Ralph Gitomer
Assistant Examiner—Mahreen Chaudhry
(74) Attorney, Agent, or Firm—Heller Ehrman White & McAuliffe LLP

(57) ABSTRACT

Compounds of formula I are useful for treating conditions associated with hyperglycemia, especially Type II diabetes. These compounds are useful in stimulating the kinase activity of the insulin receptor, activating the insulin receptor, and stimulating the uptake of glucose. Pharmaceutical compositions comprising the antidiabetic compounds are also disclosed.

37 Claims, 14 Drawing Sheets

Phosphorylation of IRS-1 and the insulin receptor with Compound 15 with and without the presence of insulin Increase in phosphorylation of the insulin receptor kinase by Compounds 13 and 15 as various concentrations Increase in glucose uptake at various concentrations of Compound 13, and 15 in the presence and absence of insulin.

Figure 5. Shows the effect of Compound 15 with Wortmannin and Cytochalasin B

Figure 6
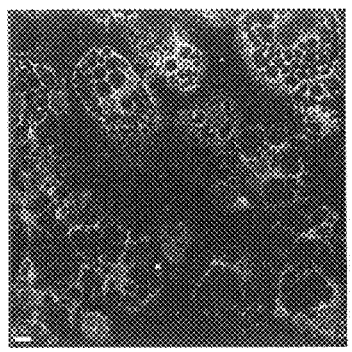
Control
Figure 6A
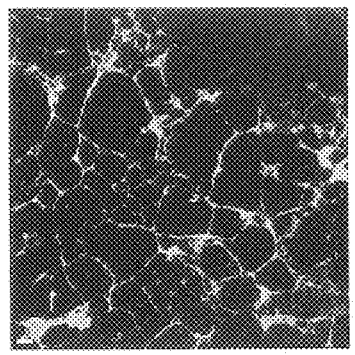
Insulin
Figure 6B
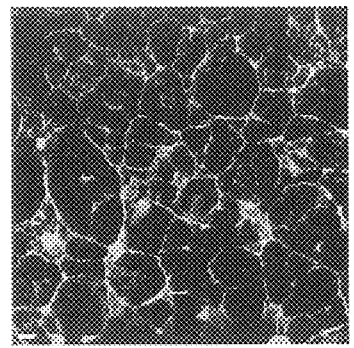
Compound 15
Figure 6C
Glut 4 migration to the cell surface when stimulated by either insulin or Compound 15

Effect of Compound 15 against the EGF receptor

Figure 8: Shows the glucose lowering effect of Compound 15 with insulin in the db/db mouse Figure 9. Shows the glucose lowering effect of Compound 15 without insulin in the db/db mouse Figure 10. Shows the effect on plasma components of Compound 15 in the ob/ob mouse

Figure 11 Effect of Compound 15 (30mg/kg, p.o.) on blood levels in the STZ/HFD rat. Results are the mean and standard error of two experiments.

Figure 12. Phosphorylation of the insulin receptor in the muscle of ST/HFD rats following the oral administration of Compound 15.

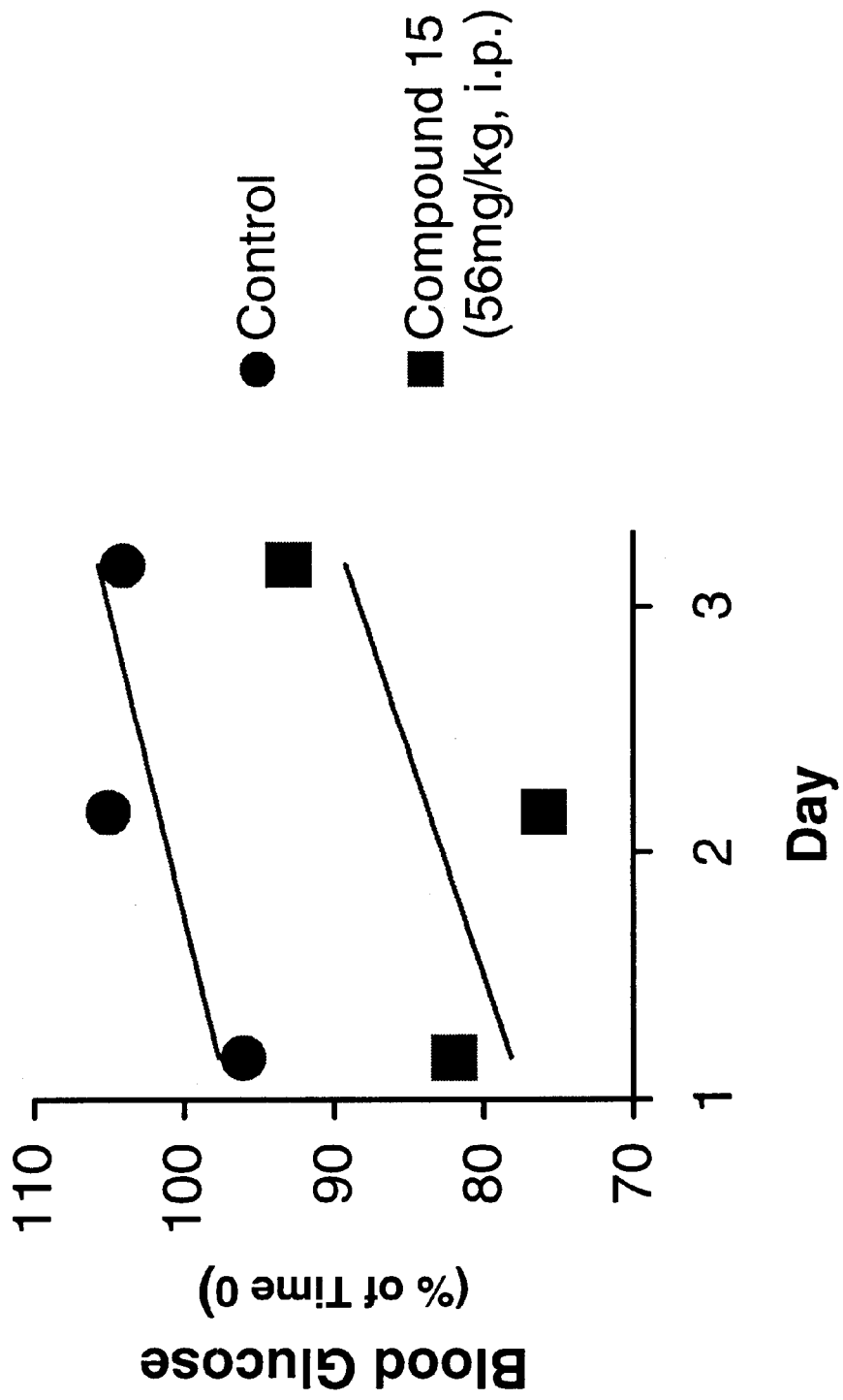
Figure 13. Shows the glucose lowering effect in the db/db mouse over three daily doses with Compound 15

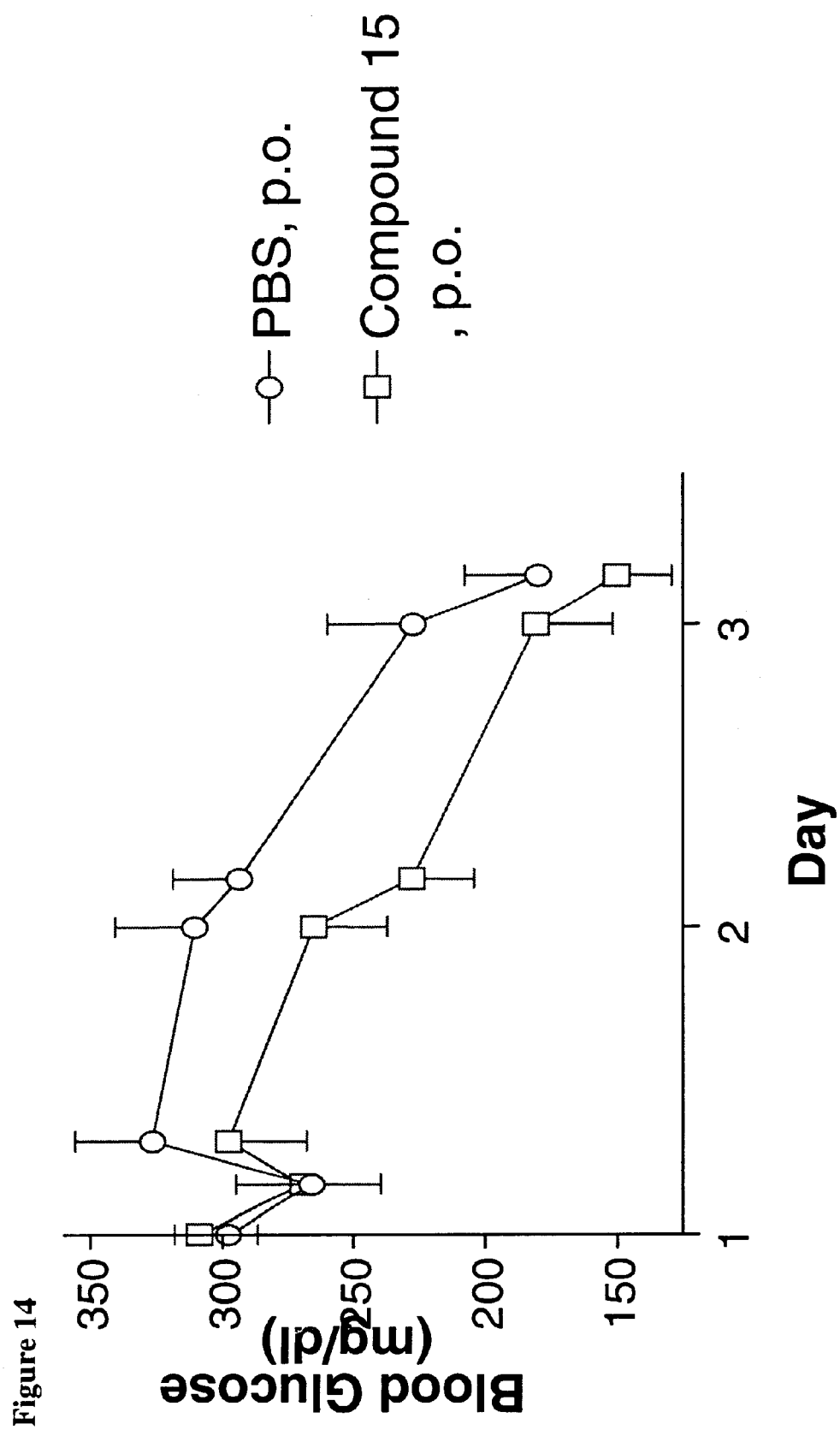
Figure 14. Shows the glucose lowering effect of Compound 15 dosed daily for three days in the STZ/HFD rat.

NAPHTHALENE UREAS AS GLUCOSE UPTAKE ENHANCERS

CROSS-REFERENCE TO RELATED APPLICATIONS

This application claims the priority under 35 USC 119(e) of Provisional Application No. 60/136,128, filed May 26, 1999.

BACKGROUND OF THE INVENTION (a) Field of the Invention

The invention relates to a means to enhance insulin-dependent glucose uptake. Specifically, the invention concerns compounds that activate the insulin receptor kinase leading to increased glucose uptake. The invention also concerns methods for treating hyperglycemia in humans, and especially methods for treating Type II diabetes.

(b) Description of Related Art

Among the many functions performed by peptide and protein hormones in metabolism is the ability to interact with receptors with high specificity. The insulin receptor is present on virtually all cells and at high concentrations on the cells for the liver, skeletal muscles, and adipose tissue. Stimulation of the insulin receptor with insulin is an essential element in carbohydrate metabolism and storage.

Diabetics either lack sufficient endogenous secretion of the insulin hormone (Type I) or have an insulin receptor-mediated signaling pathway that is resistant to endogenous or exogenous insulin (Type II, or non-insulin-dependent diabetes mellitus (NIDDM)). Type II diabetes is the most common form of diabetes, affecting about 5% of individuals in the industrialized nations. In Type II diabetics, major insulin-responsive tissues such as liver, skeletal muscle and fat exhibit the insulin resistance (Haring and Mehnert, *Diabetologia* 36:176–182 (1993); Haring et al., *Diabetologia*, 37 Suppl. 2:S149–54 (1994)). The resistance to insulin in Type II diabetes is complex and likely multi-factorial but appears to be caused by an impaired signal from the insulin receptor to the glucose transport system and to glycogen synthase. Impairment of the insulin receptor kinase has been implicated in the pathogenesis of this signaling defect. Insulin resistance is also found in many non-diabetic individuals, and may be an underlying etiologic factor in the development of the disease (Reaven, *Diabetes*, 37:1595–1607 (1988)).

Considerable information is known concerning the insulin receptor itself The receptor consists of four separate subunits consisting of two identical α and two identical β chains. The β subunits contain a tyrosine kinase activity and the ATP binding sites. The insulin receptor is activated by autophosphorylation of key tyrosine residues in its cytoplasmic tyrosine kinase domain. This autophosphorylation is required for subsequent activity of the insulin receptor. The autophosphorylation stabilizes the activated receptor kinase resulting in a phosphorylation cascade involving intracellular signaling proteins.

At present there are limited pharmacologic approaches to treatment of Type II diabetes. Insulin is currently used as a treatment, but is disadvantageous because insulin must be injected. Although several peptide analogs of insulin have been described, none with a molecular weight below about 5000 daltons retains activity. Some peptides which interact with sites on the β-subunit of the insulin receptor have shown enhancement of the activity of insulin on its receptor (Kole et al., *J. Biol. Chem.*, 271:31619–31626 (1996); Kasuya et al., *Biochem. Biophys. Res. Commun.*, 200:777–83 (1994)). Kohanski and others have reported on a variety of polycationic species that generate a basal effect, but do little to enhance insulin action (Kohanski, J. *Biol. Chem.*, 264:20984–91 (1989); Xu et al., *Biochemistry* 30:11811–19 (1991). These peptides apparently act on the cytoplasmic kinase domain of the insulin receptor.

In addition, certain non-peptide components have been found to enhance the agonist properties of peptide hormones, but none appear to act directly on the insulin receptor kinase. For instance, the ability of thiazolidinediones, such as pioglitazone, to enhance adipocyte differentiation has been described (Kletzien, et al., *Mol. Pharmacol.*, 41:393 (1992)). These thiazolidinediones represent a class of potential anti-diabetic compounds that enhance the response of target tissues to insulin (Kobayashi, *Diabetes*, 41:476 (1992)). The thiazolidinediones switch on peroxisome proliferator-activated receptor γ (PPARγ), the nuclear transcription factor involved in adipocyte differentiation (Kliewer et al., *J. Biol. Chem.*, 270:12953 (1995)) and do not have a direct effect on the insulin receptor kinase. Other anti-diabetic agents currently in use include both insulin secretagogues (such as the sulfonylureas) and biguanides (such as metfornin) that inhibit hepatic glucose output. To date, non-peptide substances which can mimic the activating effect of insulin on the insulin receptor have eluded discovery.

Bisnaphthalene ureas are known to the literature. They are heavily described as polysulfonic acid derivatives of suramin and as azo dyes. A variety of these polyanionic sulfonic acid derivatives have been established as potential therapeutics for a variety of disease indications. Suramin, described in 1917, is a polysulfonic acid that has been extensively researched (Dressel, *J. Chem. Ed.*, 38:585 (1961); Dressel, *J. Chem. Ed.*, 39:320 (1962)). It has therapeutic uses as an anthehnintic and antiprotozoal. More recently, it has been described as an inhibitor to reverse transcriptase in certain avian and murine retroviruses (De Clercq, *Cancer Letter*, 8:9 (1979); Mitsuya et al., *Science*, 226:172 (1984); Gagliardi et al., *Cancer Chemother. Pharmacol.*, 41:117 (1988); Doukas et al., *Cancer Res.* 55:5161 (1995); Mohan et al., *Antiviral Chem.*, 2:215 (1991)). Large numbers of compounds relating to suramin exist. Most of the suramin analogs which have been reported have multiple sulfonic acid functionality on each aryl ring. Recent studies indicate that polyanionic surarnin analogs have anti-angiogenic, antiproliferative activity, and anti-viral activity (Gagliardi et al., *Cancer Chemother. Pharmacol.*, 41:117 (1988); Doukas et al., *Cancer Res.*, 55:5161 (1995); Mohan et al., *Antiviral Chem.*, 2:215 (1991)). A number of bisnaphthylsulfonic acids have been described in the patent literature as complement inhibitors (U.S. Pat. Nos. 4,132,730, 4,129,591, 4,120,891, 4,102,917, 4,051,176). Additionally, there are a number of azo dye patents (DE 19521589, U.S. Pat. No. 3,716,368, DE 2216592, FR 1578556) which disclose polysulfonated naphthalene azo compounds. Bisnaphthalene urea 2-sulfonamide 3-azo compounds have been solely reported as a recording liquid (JP 58191772). However, none of the suramin analogs or azo dyes have been suggested to be useful in the treatment of hyperglycemia or diabetes.

SUMMARY OF THE INVENTION

This invention is directed to bisnaphthalene ureas which enhance glucose uptake in mammals, to pharmaceutical compositions thereof, and to methods for enhancing glucose uptake using these compounds.

In a first embodiment, this invention provides compounds of formula I:

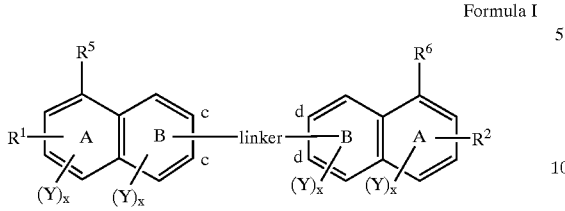

Formula I where

R$^1$ and R$^2$ are substituents on the A rings and are, independently, —SO$_2$NR$^7$$_2$, —C(O)NR$^7$$_2$, NR$^7$SO$_2$R$^7$, —NR$^7$C(O)R$^7$, —SO$_2$OR$^7$, —C(O)OR$^7$, —OSO$_2$R$^7$, or —OC(O)R$^7$, R$^3$ and R$^4$ are, independently, hydrogen or lower alkyl, or R$^3$ and R$^4$ together are —(CH$_2$)$_2$—, —(CH$_2$)$_3$—, or —(CH$_2$)$_4$—, or R$^3$ or R$^4$ may be an electron pair, R$^5$ and R$^6$ are, independently, hydrogen, alkyl, substituted alkyl, cyano, halo, nitro, —SR$^8$, —C(O)R$^8$, —SO$_2$OR$^8$, —OSO$_2$R$^8$, —SO$_2$NR$^8$$_2$, —NR$^8$SO$_2$R$^8$, —OC(O)R$^8$, —C(O)OR$^8$, —C(O)NR$^8$$_2$, —NR$^8$C(O)R$^8$, —OR$^8$, or —NR$^8$$_2$, each R$^7$ and R$^8$ is, independently, hydrogen, alkyl, substituted alkyl, aryl, substituted aryl, aryl(lower)alkyl, substituted aryl(lower)alkyl, heteroaryl(lower)alkyl, substituted heteroaryl(lower)alkyl, heterocyclyl, substituted heterocyclyl, heteroaryl, or substituted heteroaryl, each Y is, independently, a non-interfering substituent which is not linked to the naphthalene ring via an azo or amide linkage, each x is, independently, 0, 1 or 2, and linker connects a carbon designated as c to a carbon designated as d, and is

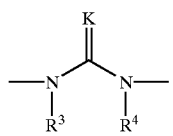

where K is O, S, or NR*, and R* is H, cyano, or lower alkyl; or

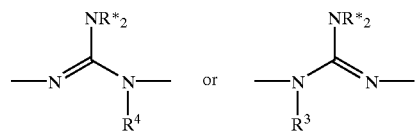

where R* is H or lower alkyl; or

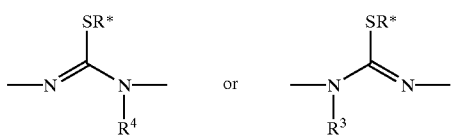

where R* is H, cyano, or lower alkyl;

or 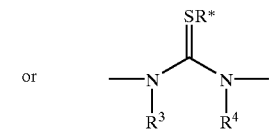

where R* is cyano or lower alkyl;
and, where, if R$^1$ and R$^2$ are both —SO$_2$OH, then:
(i) no Y is —SO$_2$OH;
(ii) neither R$^5$ nor R$^6$ is —SO$_2$OR$^8$ or —OSO$_2$R$^8$; and
(iii) R$^5$ and R$^6$ are not both selected from the group consisting of hydroxy and hydrogen unless at least one (Y)$_x$ is (Y')$_{x'}$ where x' is 1 or 2 and Y'is a halo, and the pharmaceutically acceptable salts thereof, as single stereoisomers or mixtures of stereoisomers. These compounds are useful as glucose uptake agonists and in the treatment of hyperglycemia and diabetes.

In a second embodiment, this invention provides pharmaceutical compositions comprising (a) a pharmaceutically acceptable carrier and (b) as an active ingredient, a compound of the first embodiment. These compositions are useful for stimulating the uptake of glucose into cells in a mammal or for treating a mammalian disease state selected from the group consisting of hyperglycemia, type I diabetes, and type II diabetes.

In a third embodiment, this invention provides a method of stimulating the kinase activity of the insulin receptor, comprising contacting the insulin receptor, or the kinase portion thereof, with a compound of the first embodiment, in an amount sufficient to stimulate the kinase activity of the insulin receptor.

In a fourth embodiment, this invention provides a method of activating the insulin receptor is provided, comprising contacting the insulin receptor, or the kinase portion thereof, with a compound of the first embodiment, in an amount sufficient to effect activation of the insulin receptor.

In a fifth embodiment, this invention provides a method for stimulating the uptake of glucose into cells which display the insulin receptor, involving contacting the cells, optionally in the presence of insulin, with a compound of the first embodiment, in an amount sufficient to stimulate the uptake of glucose into the cells. The uptake of glucose into cells in a mammal may be effected by administering the compound of the invention to the mammal.

In other embodiments, the invention provides methods of treating hyperglycemia, type I diabetes, or type II diabetes in a mammal, such as a human by administering a therapeutically effective amount of a compound of the first embodiment or a composition containing said compound.

BRIEF DESCRIPTION OF THE DRAWINGS

FIG. 6 shows GLUT4 immunofluorescence of cells when treated with Compound 15.

FIG. 13 shows the effect of Compound 15 after 3 single daily doses in the db/db mouse.

FIG. 14 shows the effect of Compound 15 after 3 single daily doses in the STZ/HFD rat.

Figure 1:
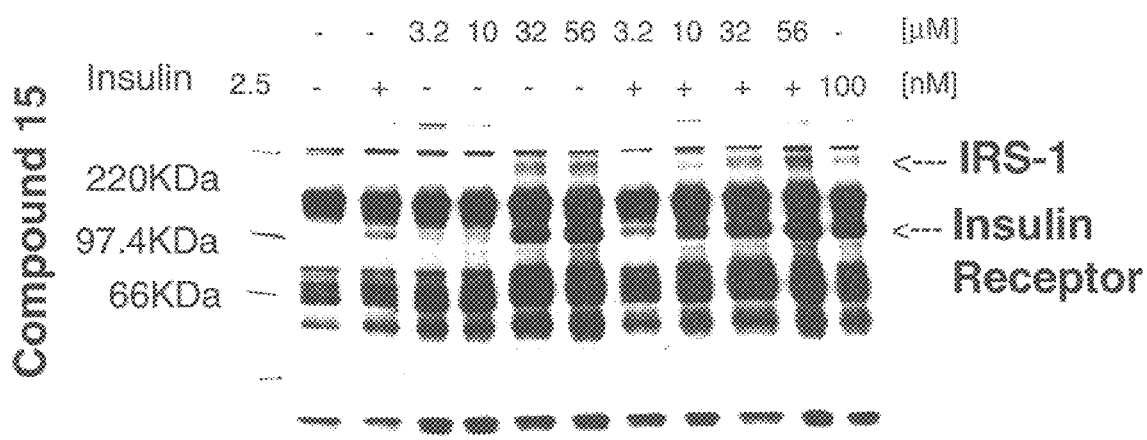
FIG. 1 shows the phosphorylation of IRS-1 and the insulin receptor with Compound 15 with and without insulin.

DETAILED DESCRIPTION OF THE INVENTION (a) Definitions and General Parameters

"Alkyl", as in "alkyl", or "alkyloxy", means $C_1$–$C_{20}$ monovalent hydrocarbyl moiety which may be linear, branched, or cyclic. "Lower alkyl", as in "lower alkyl" "halo-lower alkyl", "aryl(lower)alkyl", or "heteroaryl (lower)alkyl", means a $C_1$–$C_6$ alkyl. The term "lower akyl" includes such moieties as methyl, ethyl, isopropyl, propyl, butyl, isobutyl, sec-butyl, tert-butyl, pentyl, hexyl, cyclopentyl, cyclopropylmethyl, or cyclohexyl. $C_1$–$C_4$ lower alkyls are preferred. "Lower alkyl" as used herein includes moieties with one olefinic bond, such as allyl.

A "substituted alkyl" or "substituted lower alkyl" is an alkyl or lower alkyl, respectively, which is typically mono-, di-, or trisubstituted with a moiety such as aryl, R'-substituted aryl, heteroaryl, niitro, cyano, halo, —OR, —SR, —COR, —OC(O)R, —C(O)OR, —NR$_2$, —SO$_2$R, —OSO$_2$R, —SO$_2$NR$_2$, —NRSO$_2$R, —CONR$_2$, or —NRCOR, where each R is, independently, hydrogen, lower alkyl, R'-substituted lower alkyl, aryl, R'-substituted aryl, heteroaryl, heteroaryl(lower)alkyl, R'-substituted aryl (lower)alkyl, or aryl(lower)alkyl and each R' is, independently, hydroxy, halo, lower alkyloxy, cyano, thio, nitro, lower alkyl, halo-lower alkyl, or amino. Substituted alkyls or substituted lower alkyls which are substituted with one to three of the substituents selected from the group consisting of cyano, halo, lower alkyloxy, thio, nitro, amino, or hydroxy are particularly preferred.

The term "halo-lower alkyl" means a lower alkyl substituted with one to three halo groups, and is further exemplified by such radicals as —CF$_3$, —CH$_2$CF$_3$ and —CH$_2$CCl$_3$.

"Aryl", as in "aryl", "aryloxy", and "aryl(lower)alkyl", means a radical derived from an aromatic hydrocarbon containing 6 to 20 ring carbon atoms, having a single ring (e.g., phenyl), or two or more condensed rings, preferably 2 to 3 condensed rings (e.g., naphthyl), or two or more aromatic rings, preferably 2 to 3 aromatic rings, which are linked by a single bond (e.g., biphenyl). The aryl is preferably $C_6$–$C_{16}$ and even more preferably, $C_6$ to $C_{14}$.

A "substituted aryl" is an aryl radical which is mono-, di-, or trisubstituted, independently, with a moiety such as a hydroxy, triazolyl, tetrazolyl, hydroxyisoxazolyl, phosphonic acid or phosphonate residue, alkyl, R'-substituted alkyl, halo, trifluoromethyl, cyano, nitro, —SR, —OR, —COR, —OCOR, —SO$_2$OR, —OSO$_2$R, —SO$_2$NR$_2$, —NRSO$_2$R, —COOR, —NR$_2$, —CONR$_2$, or —NRCOR, where each R is, independently, hydrogen, lower alkyl, R'-substituted lower alkyl, aryl, R'-substituted aryl, heteroaryl, heteroaryl (lower)alkyl, aryl(lower)alkyl, or R'-substituted aryl(lower) alkyl and each R' is, independently hydroxy, halo, lower alkyloxy, cyano, thio, nitro, lower alkyl, halo-lower alkyl, amino, or —COOR, where R is as defined above. Especially preferred substituents on a substituted aryl are lower alkyl, halo-lower alkyl, halo, cyano, thio, nitro, amino, lower alkyloxy, or hydroxy. The radicals —SO$_2$OR, —SO$_2$NR$_2$, —COOR, and —CONR$_2$, where R is hydrogen or lower alkyl, are also especially preferred substituents of substituted aryls on the compounds of the present invention.

"Heteroaryl", as in "heteroaryl" and "heteroaryl(lower) alkyl", means a radical derived from an aromatic hydrocarbon containing 5 to 14 ring atoms, 1 to 5 of which are hetero atoms chosen, independently, from N, O, or S, and includes monocyclic, condensed heterocyclic, and condensed carbocyclic and heterocyclic aromatic rings (e.g., thienyl, fliryl, pyrrolyl, pyrimidinyl, isoxazolyl, oxazolyl, triazolyl, tetrazolyl, indolyl, isobenzofuranyl, purinyl, isoquinolyl, pteridinyl, imidazolyl, pyridyl, pyrazolyl, pyrazinyl, quinolyl, etc.).

A "substituted heteroaryl" may have from one to three substituents such as an alkyl, R'-substituted alkyl, halo, cyano, nitro, —SR, —OR, —COR, —OOCR, —SO$_2$OR, —OSO$_2$R, —SO$_2$NR$_2$, —NRSO$_2$R, —COOR, —NR$_2$, —CONR$_2$, or —NRCOR, where each R is independently hydrogen, lower alkyl, R'-substituted lower alkyl, aryl, R'-substituted aryl, heteroaryl, heteroaryl(lower)alkyl, aryl (lower)alkyl, or R'-substituted aryl(lower)alkyl and each R' is, independently, hydroxy, halo, lower alkyloxy, cyano, thio, nitro, lower alkyl, halo-lower alkyl, or amino. In addition, any two adjacent substituents on the heteroaryl may optionally together form a lower alkylenedioxy. Particularly preferred substituents on the substituted heteroaryl include hydroxy, halo, lower alkyloxy, cyano, thio, nitro, lower alkyl, halo-lower alkyl, halo-lower alkyl, or amino.

"Heterocyclyl" means a radical derived from an aliphatic, cyclic hydrocarbon containing 5 to 14 ring atoms, 1 to 5 of which are hetero atoms chosen, independently, from N, O, or S. Monocyclic rings (e.g., tetrahydrofuranyl, tetrahydropyranyl, piperidinyl, etc.) are preferred.

A "substituted heterocyclyl" may have from one to three substituents, preferably substituents like an alkyl, R'-substituted alkyl, halo, cyano, nitro, —SR, —OR, —COR, —OOCR, —SO$_2$OR, —OSO$_2$R, —SO$_2$NR$_2$, —NRSO$_2$R, —COOR, —NR$_2$, —CONR$_2$, or —NRCOR, where each R is, independently, hydrogen, loweralkyl, R'-substituted alkyl, aryl, R'-substituted aryl, heteroaryl, heteroaryl(lower)alkyl, aryl(lower)alkyl, or R'-substituted aryl(lower)alkyl and each R' is, independently hydroxy, halo, lower alkyloxy, cyano, thio, nitro, lower alkyl, halo-lower alkyl, or aimino. Preferred substituents on a substituted heterocyclyl include lower alkyl, halo-lower alkyl, halo, cyano, thio, amino, lower alkyloxy, or hydroxy.

"Aryl(lower)alkyl" means a lower alkyl radical which is substituted with an aryl, as previously defined. A "substituted aryl(lower)alkyl" means an aryl(lower)alkyl radical having one to three substituents on the aryl portion or the alkyl portion of the radical, or both.

"Heteroaryl(lower)alkyl" means a lower alkyl radical which is substituted with a heteroaryl, as previously defined. A "substituted heteroaryl(lower)aryl" means a heteroaryl (lower)alkyl radical having one to three substituents on the heteroaryl portion or the alkyl portion of the radical, or both.

A "lower alkyloxy" means an —OR radical, where R is a lower alkyl.

"Halo" means bromo, fluoro, or chloro.

A "non-interfering substituent" means a substituent which, when present on a given compound, does not substantially decrease or otherwise inhibit a particular, desired bioactivity of the compound, such as the ability of the compound to stimulate the kinase activity of the insulin receptor, to activate the insulin receptor, or to stimulate the uptake of glucose into cells displaying the insulin receptor. The presence of the non-interfering substituent should not detrimentally affect the bioactivity of the compound by more than about 30%. Preferably, the non-interfering substituent decreases the bioactivity of the compound by less than about 10%. Most preferably, the non-interfering substituent does not decrease the bioactivity of the compound to any detectable degree. However, the effect of the presence of the non-interfering substituent on the compound need not be neutral. For instance, the non-interfering substituent may optionally increase a particular bioactivity of the compound. Suitable non-interfering substituents include, but are not limited to, alkyl, substituted alkyl, cyano, halo, nitro, —SR, —OR, and —NR$_2$, where each R is, independently, hydrogen, lower alkyl, or substituted lower alkyl.

An "azo linkage" is the group —N=N—. A typical "amnide linkage" is the group

where R may be alkyl, aryl, or hydrogen.

A "pharmaceutically acceptable salt" may be any salt derived from an inorganic or organic acid or an inorganic or organic base. The term "pharmaceutically acceptable anion" refers to the anion of such acid addition salts. The term "pharmaceutically acceptable cation" refers to a cation formed by addition of a base. The salt and/or the anion or cation are chosen not to be biologically or otherwise undesirable.

"Stereoisomers" are compounds that have the same sequence of covalent bonds and differ in the relative disposition of their atoms in space.

"Inner salts"0 or "zwitterions" can be formed by transferring a proton from the carboxyl group onto the lone pair of electrons of the nitrogen atom in the amino group.

"Therapeutically effective amount" means that amount which, when administered to a mammal for treating a disease, is sufficient to effect such treatment for the disease.

"Treating" or "treatment" of a disease in a mammal includes:

(1) preventing the disease from occurring in a mammal which may be predisposed to the disease but does not yet experience or display symptoms of the disease, (2) inhibiting the disease, i.e., arresting its development, or (3) relieving the disease, i.e., causing regression of the disease.

The "kinase portion thereof", with respect to the insulin receptor, means the cytoplasmic tyrosine kinase domain of the insulin receptor.

(b) Nomenclature

The compounds of formula I are numbered and named as described below with reference to formula Ia.

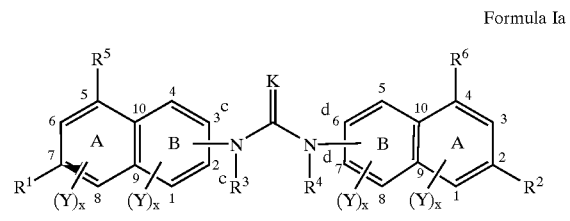

Formula Ia

In the compound of formula Ia shown, the substituent $R^1$ is in the 7-position of the naphthalene ring, and $R^2$ is in the 2-position of the naphthalene ring when the numbering of the ring atoms is as shown. For example, if $R^1$ is $SO_2OH$, $R^2$ is $SO_2OH$, $R^3$ is H, $R^4$ is H, $R^5$ is H, $R^6$ is H, and K is O, and the aminocarbonylamino linker is attached to C2 of the naphthalene ring with the $R^5$ substituent and is attached to C7 of the naphthalene ring with the $R^6$ substituent on it, the compound is 7-{[(7-sulfo-2-naphthyl)amino]carbonylamino}naphthalene-2-sulfonic acid.

(c) Compounds and Pharmaceutical Compositions Thereof

The compounds of the invention comprise compounds of formula I:

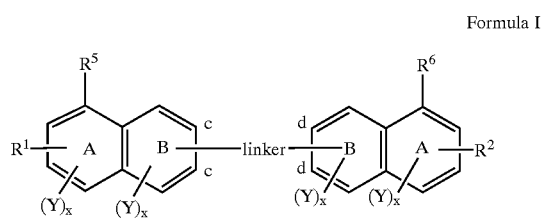

Formula I where $R^1$ and $R^2$ are substituents on the A rings and are, independently, —$SO_2NR^7_2$, $C(O)NR^7_2$, —$NR^7SO_2R^7$, —$NR^7C(O)R^7$, —$SO_2OR^7$, —$C(O)OR^7$, —$OSO_2R^7$, or —$OC(O)R^7$, $R^3$ and $R^4$ are, independently, hydrogen or lower alkyl, or $R^3$ and $R^4$ together are —$(CH_2)_2$—, —$(CH_2)_3$—, or —$(CH_2)_4$—, or $R^3$ or $R^4$ may be an electron pair, p1 $R^5$ and $R^6$ are, independently, hydrogen, alkyl, substituted alkyl, cyano, halo, nitro, —$SR^8$, —$C(O)R^8$, —$SO_2OR^8$, —$OSO_2R^8$, —$SO_2NR^8_2$, —$NR^8SO_2R^8$, —$OC(O)R^8$, —$C(O)OR^8$, —$C(O)NR^8_2$, —$NR^8C(O)R^8$, —$OR^8$, or —$NR^8_2$, each $R^7$ and $R^8$ is, independently, hydrogen, alkyl, substituted alkyl, aryl, substituted aryl, aryl(lower)alkyl, substituted aryl(lower)alkyl, heteroaryl(lower)alkyl, substituted heteroaryl(lower)alkyl, heterocyclyl, substituted heterocyclyl, heteroaryl, or substituted heteroaryl, each Y is, independently, a non-interfering substituent which is not linked to the naphthalene ring via an azo or amide linkage, each x is, independently, 0, 1 or 2, and the linker connects a carbon designated as c to c carbon designated as d, and is

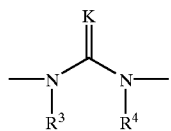

where K is O, S, or NR*, and R* is H, cyano, or lower alkyl; or

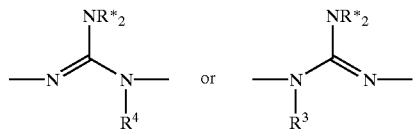

where R* is H or lower alkyl; or

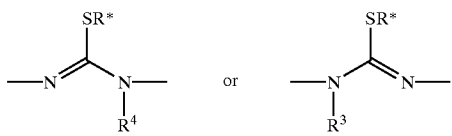

where R* is H, cyano, or lower alkyl;

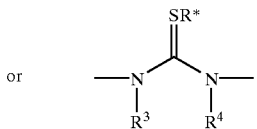

where R* is cyano or lower alkyl;

and, where, if $R^1$ and $R^2$ are both —SO$_2$OH, then:
(i) no Y is —SO$_2$OH;
(ii) neither $R^5$ nor $R^6$ is —SO$_2$OR$^8$ or OSO$_2$R$^8$; and
(iii) $R^5$ and $R^6$ are not both selected from the group consisting of hydroxy and hydrogen unless at least one $(Y)_x$ is $(Y')_{x'}$ where x' is 1 or 2 and Y' is a halo, and the pharmaceutically acceptable salts thereof, as single stereoisomers or mixtures of stereoisomers.

Preferred compounds of formula I include compounds of formula II:

Formula II

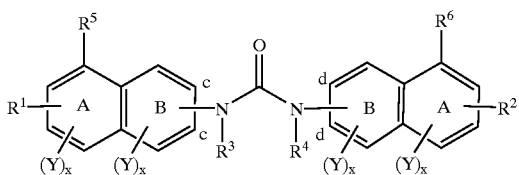

where the substituents and linker are as defined above, and pharmaceutically acceptable salts thereof, as single stereoisomers or mixtures of stereoisomers.

Preferably, the compounds of formula II include compounds of formula IIa

Formula IIa

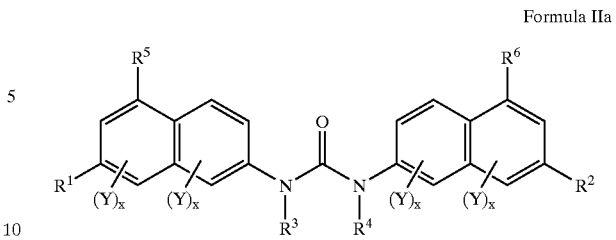

where the substituents and linker are as defined above, and pharmaceutically acceptable salts thereof, as single stereoisomers or mixtures of stereoisomers.

Preferably, each non-interfering substituent Y is alkyl, substituted alkyl, cyano, halo, nitro, —SR$^9$, —OR$^9$, or —NR$^9{}_2$, where each R$^9$ is, independently, hydrogen, lower alkyl, or substituted lower alkyl. Most preferably, each Y is lower alkyl, halo-lower alkyl, lower alkyloxy, cyano, halo, thio, nitro, amino, or hydroxy.

In the compounds of formula I, Ia, II, and IIa, each x is preferably zero or one. In particularly preferred embodiments, each x is zero.

In one preferred embodiment of the compounds of the invention, $R^1$ and $R^2$ are, independently, —SO$_2$OR$^{10}$, —C(O)OR$^{10}$, —SO$_2$NR$^{11}$R$^{10}$, —C(O)NR$^{11}$R$^{10}$, —OSO$_2$R$^{10}$, —OC(O)R$^{10}$, —NR$^{11}$SO$_2$R$^{10}$, or —NR$^{11}$C(O)R$^{10}$; each R$^{11}$ is, independently, hydrogen or lower alkyl; and each R$^{10}$ is, independently, alkyl, substituted alkyl, aryl, substituted aryl, aryl(lower)alkyl, substituted aryl(lower)alkyl, heteroaryl(lower)alkyl, substituted heteroaryl(lower)alkyl, heterocyclyl, substituted heterocyclyl, heteroaryl, or substituted heteroaryl. $R^1$ and $R^2$ are preferably, independently, —SO$_2$NR$^{11}$R$^{10}$, —C(O)NR$^{11}$R$^{10}$, —NR$^{11}$SO$_2$R$^{10}$, or —NR$^{11}$C(O)R$^{10}$. In a further preferred embodiment, R$^{11}$ is hydrogen. For instance, in particularly preferred compounds, $R^1$ and $R^2$ are, independently, —SO$_2$NHR$^{10}$ or —NHSO$_2$R$^{10}$.

In an alternative preferred embodiment, $R^1$ is —SO$_2$OR$^{10}$, —C(O)OR$^{10}$, —SO$_2$NR$^{11}$R$^{10}$, —C(O)NR$^{11}$R$^{10}$, —OSO$_2$R$^{10}$, —OC(O)R$^{10}$, —NR$^{11}$SO$_2$R$^{10}$, or —NR$^{11}$C(O)R$^{10}$, and $R^2$ is —SO$_2$OR$^{11}$, or —C(O)OR$^{11}$, where R$^{10}$ and R$^{11}$ are as previously defined in the preceding paragraph. $R^1$ is, preferably, —SO$_2$NR$^{11}$R$^{10}$, —C(O)NR$^{11}$R$^{10}$, —NR$^{11}$SO$_2$R$^{10}$, or —NR$^{11}$C(O)R$^{10}$. In a further preferred embodiment, R$^{11}$ is hydrogen. For instance, in particularly preferred compounds, $R^1$ is —SO$_2$NHR$^{10}$ or —NHSO$_2$R$^{10}$. In one preferred embodiment, $R^2$ is —C(O)NR$^{11}{}_2$ or —C(O)OR$^{11}$. In an alternative preferred embodiment, $R^2$ is —SO$_2$NR$^{11}{}_2$ or —SO$_2$OR$^{11}$, such as —SO$_2$OH.

In one preferred embodiment of the invention, each R$^{10}$ is, independently, a substituted alkyl, substituted aryl, substituted aryl(lower)alkyl, substituted heteroaryl(lower)alkyl, substituted heterocyclyl, or substituted heteroaryl; at least one of the substituents on R$^{10}$ is R$^{12}$; each $R^2$ is, independently, —SO$_2$OR$^{13}$, —C(O)OR$^{13}$, —SO$_2$NR$^{13}{}_2$, —C(O)NR$^{13}{}_2$, hydroxy, triazolyl, tetrazolyl, hydroxyisoxazolyl, a phosphonic acid residue, or a phosphonate residue; and each R$^{13}$ is, independently, hydrogen or lower alkyl. R$^{10}$ in this embodiment is preferably a substituted aryl or substituted heteroaryl. It is particularly preferred that R$^{10}$ be a substituted phenyl. In preferred compounds of the invention, each R$^{12}$ is, independently, —C(O)OR$^{13}$, —C(O)NR$^{13}{}_2$, —SO$_2$OR$^{13}$, hydroxy, triazolyl, tetrazolyl, hydroxyisoxazolyl, a phosphonic acid residue, or a phosphonate residue. In particular, it is preferred that $R^{12}$ be —C(O)OR$^{13}$, —SO$_2$OR$^{13}$, hydroxy, triazolyl, tetrazolyl, hydroxyisoxazolyl, a phosphonic acid residue, or a phosphonate residue. For instance, each $R^{12}$ may be —C(O)OH, —SO$_2$OR$^{13}$, or —C(O)OCH$_3$. In a alternatively preferred compounds, each $R^{12}$ is, independently, —SO$_2$OR$^{13}$ or —SO$_2$NR$^{13}_2$. It is particularly preferred that $R^{12}$ be —SO$_2$OR$^{13}$. In especially preferred compounds, $R^{12}$ is —SO$_2$OH. It is preferred that, when $R^{12}$ is —C(O)OR$^{13}$ or —SO$_2$OR$^{13}$, $R^{12}$ shall be adjacent on the aryl, heteroaryl, or heterocyclyl ring to a substituent such as chloro or hydroxy.

In an alternative preferred embodiment of the invention, each $R^{10}$ is, independently, an aryl, heteroaryl, aryl(lower) alkyl, or heteroaryl(lower)alkyl. In this embodiment, $R^{10}$ is preferably phenyl, pyridyl, pyrazinyl, or pyrimidinyl.

In still other preferred compounds of the invention, each $R^1$ and $R^2$ are, independently, —SO$_2$NR$^7_2$, —C(O)NR$^7_2$, —SO$_2$OR$^7$, or —C(O)OR$^7$; and each $R^7$ is, independently, hydrogen or lower alkyl. Preferably, $R^1$ and $R^2$ are, independently, —C(O)OR$^7$ or —C(O)NR$^7_2$. In other preferred compounds of formula I, however, $R^1$ and $R^2$ are, independently, —SO$_2$OR$^7$ or —SO$_2$NR$^7_2$. For instance, $R^1$ and $R^2$ may both be —SO$_2$OH. Preferably, if $R^1$ and $R^2$ are both —SO$_2$OH then $R^5$ and $R^6$ are not both either hydroxy or hydrogen.

Preferably, $R^3$ and $R^4$ of the compounds of the invention are hydrogen.

Preferably, $R^5$ and $R^6$ are independently, hydrogen, alkyl, substituted alkyl, cyano, halo, nitro, —OR$^8$, $^{NR8}_2$, or —SR$^8$, where each $R^8$ is, independently, hydrogen, lower alkyl, substituted lower alkyl, aryl, substituted aryl, aryl(lower) alkyl, substituted aryl(lower)alkyl, heteroaryl, or heteroaryl (lower)alkyl. Most preferably, $R^5$ and $R^6$ are, independently, hydrogen, hydroxy, halo, cyano, lower alkyl, halo-lower alkyl, lower alkyloxy, nitro, amino, or thio. In many preferred compounds of the invention, $R^5$ and $R^6$ are both hydrogen or hydroxy.

The compounds of formula I and formula II are preferably symmetrical.

Compounds of the invention comprising more than one preferred substituent are preferred. If one compound comprises more preferred substituents than a second compound, then the first compound is preferred over the second. For instance, compounds of formula I which have preferred radicals for each substituent $R^1$ through $R^4$ and $R^{10}$ through $R^{12}$ are preferred over those which have preferred radicals for only the substituents $R^1$ through $R^3$.

For example, preferred compounds of the invention include those of formula III:

Formula III

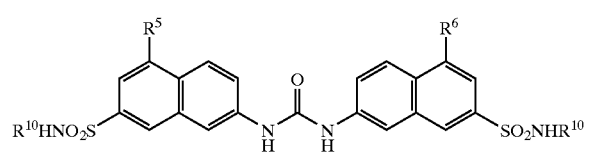

where $R^5$ and $R^6$ are selected from the group consisting of hydrogen and hydroxy; and each $R^{10}$ is, independently, substituted aryl or substituted heteroaryl; at least one of the substituents on $R^{10}$ is $R^{12}$; each $R^{12}$ is, independently, —SO$_2$OR$^{13}$, —C(O)OR$^{13}$, —SO$_2$NR$^{13}_2$, —C(O)NR$^{13}_2$, triazolyl, tetrazolyl, isoxazolyl, a phosphonic acid residue, or a phosphonate residue; and each $R^{13}$ is, independently, hydrogen or lower alkyl, and pharmaceutically acceptable salts thereof as single stereoisomers or mixtures of stereoisomers.

Preferably, when $R^{12}$ is —CO(O)R$^{13}$ or —SO$_2$OR$^{13}$, $R^{12}$ is adjacent on the aryl, heteroaryl, or heterocyclyl ring to a further substituent, such as chloro or hydroxy.

Other examples of compounds of the present invention include those of formula IV:

Formula IV

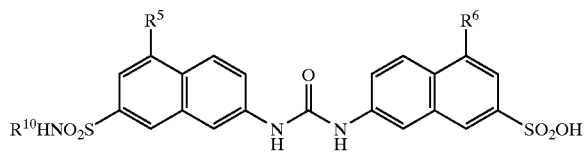

where $R^5$ and $R^6$ are selected from the group consisting of hydrogen and hydroxy; $R^{10}$ is substituted aryl or substituted heteroaryl; at least one of the substituents on $R^{10}$ is $R^{12}$; each $R^{12}$ is, independently, —SO$_2$OR$^{13}$, —C(O)OR$^{13}$, —SO$_2$NR$^{13}_2$, —C(O)NR$^{13}_2$, triazolyl, tetrazolyl, isoxazol, a phosphonic acid residue, or a phosphonate residue; and each $R^{13}$ is, independently, hydrogen or lower alkyl, and pharmaceutically acceptable salts thereof as single stereoisomers or mixtures of stereoisomers. Preferably, when $R^{12}$ is —CO(O)R$^{13}$ or —SO$_2$OR$^{13}$, $R^{12}$ shall be adjacent on the aryl, heteroaryl, or heterocyclyl ring to a substituent such as chloro or hydroxy.

Preferred compounds of the present invention include, but are not limited to, the following compounds:

4-hydroxy-7-{[(5-hydroxy-7-sulfo(2-naphthyl))amino] carbonylamino}naphthalene-2-sulfonic acid disodium salt;

3-{[(4-hydroxy-7-{[(5-hydroxy-7-{[(3-sulfophenyl)amino] sulfonyl}(2-naphthyl))amino]-carbonylamino}-2-naphthyl)sulfonyl]amino}benzenesulfonic acid;

2-[6-({[5-(carboxymethoxy)-7-sulfo(2-naphthyl)] amino}carbonylamino)-3-sulfonaphthyloxy]acetic acid;

3-bromo-7-{[(6-bromo-5-hydroxy-7-sulfo(2-naphthyl)) amino]carbonylamino}-4-hydroxynaphthalene-2-sulfonic acid;

4-[(2-sulfophenyl)methoxy]-7-[({7-sulfo-5-[(2-sulfophenyl)methoxy](2-naphthyl)}amino)-carbonylamino]naphthalene-2-sulfonic acid;

4-hydroxy-7-{[(5-methoxy-7-sulfo(2-naphthyl))amino] carbonylamino}naphthalene-2-sulfonic acid;

4-methoxy-7-{[(5-methoxy-7-sulfo(2-naphthyl))amino] carbonylamino}naphthalene-2-sulfonic acid;

7-[({5-[(ethoxycarbonyl)methoxy]-7-sulfo(2-naphthyl) }amino)carbonylamino]-4-hydroxynaphthalene-2-sulfonic acid;

4-[(ethoxycarbonyl)methoxy]-7-[({5-[(ethoxycarbonyl) methoxy]-7-sulfo(2-naphthyl)}amino)-carbonylamino] naphthalene-2-sulfonic acid;

4-(3-sulfopropoxy)-7-({[7-sulfo-5-(3-sulfopropoxy)(2-naphthyl)]amino}carbonylamino)naphthalene-2-sulfonic acid;

4-hydroxy-7-({[7-sulfo-5-(3-sulfopropoxy)(2-naphthyl)] amino}carbonylamino)naphthalene-2-sulfonmc acid;

N-(5-hydroxy-7-sulfamoyl(2-naphthyl))[(5-hydroxy-7-sulfamoyl(2-naphthyl))amino]-carboxamide;

4-hydroxy-7-{[(5-hydroxy-7-{[(3-sulfophenyl)amino] sulfonyl}(2-naphthyl))amino]-carbonylamino}naphthalene-2-sulfonic acid;

methyl 3-({[4-hydroxy-7-({[5-hydroxy-7-({[3-(methoxycarbonyl)phenyl]amino}sulfonyl)-(2-naphthyl)] amino}carbonylamino)-2-naphthyl]sulfonyl}amino) benzoate;

3-{[(7-{[(7-{[(3-carboxyphenyl)amino]sulfonyl}-5-hydroxy(2-naphthyl))amino]-carbonylamino}-4-hydroxy-2-naphthyl)sulfonyl]amino}benzoic acid;

4-{[(7-{[(7-{[(4-carboxyphenyl)amino]sulfonyl}-5-hydroxy(2-naphthyl))amino]-carbonylamino}-4-hydroxy-2-naphthyl)sulfonyl]amino}benzoic acid;

4-{[(4-hydroxy-7-{[N-(5-hydroxy-7-sulfo(2-naphthyl))carbamoyl]amino}-2-naphthyl)sulfonyl]-amino}benzoic acid;

methyl 4-({[4-hydroxy-7-({N-[5-hydroxy-7-({[4-(methoxycarbonyl)phenyl]amino}sulfonyl)-(2-naphthyl)]carbamoyl}amino)-2-naphthyl]sulfonyl}amino)benzoate;

4-hydroxy-7-({[5-hydroxy-7-({[4-(methoxycarbonyl)phenyl]amino}sulfonyl)(2-naphthyl)]amino}carbonylamino)naphthalene-2-sulfonic acid;

7-{[(7-sulfo-2-naphthyl)amino]carbonylamino}naphthalene-2-sulfonic acid;

7-{[(7-{[(3-sulfophenyl)amino]sulfonyl}-2-naphthyl)amino]carbonylamino}naphthalene-2-sulfonic acid;

3-{[(7-{[N-(7-{[(3-sulfophenyl)amino]sulfonyl}-2-naphthyl)carbamoyl]amino}-2-naphthyl)-sulfonyl]amino}benzenesulfonic acid;

methyl 3-({[7-({[7-({[3-(methoxycarbonyl)phenyl]amino}sulfonyl)-2-naphthyl]amino}-carbonylamino)-2-naphthyl]sulfonyl}amino)benzoate;

3-{[(7-{[N-(7-{[(3-carboxyphenyl)amino]sulfonyl}-2-naphthyl)carbamoyl]amino}-2-naphthyl)-sulfonyl]amino}benzoic acid;

N-{7-[(phenylamino)sulfonyl](2-naphthyl)}({7-[(phenylamino)sulfonyl](2-naphthyl)}amino)carboxamide;

N-(7-{[(3-sulfamoylphenyl)amino]sulfonyl}(2-naphthyl))[(7-{[(3-sulfamoylphenyl)amino]sulfonyl}(2-naphthyl))amino]carboxamide;

N-{7-[(3-pyridylamino)sulfonyl](2-naphthyl)}({7-[(3-pyridylamino)sulfonyl]-2-naphthyl}amino)carboxamide;

N-{7-[(pyrazin-2-ylamino)sulfonyl](2-naphthyl)}({7-[(pyrazin-2-ylamino)sulfonyl]-2-naphthyl}amino)carboxamide;

N-{7-[(pyrimidin-2-ylamino)sulfonyl](2-naphthyl)}({7-[(pyrimidin-2-ylamino)sulfonyl]-2-naphthyl}amino)carboxamide;

4-methylphenyl 3-[({7-[(N-{7-[({3-[(4-methylphenyl)oxysulfonyl]phenyl}amino)sulfonyl]-2-naphthyl}carbamoyl)amino]-2-naphthyl}sulfonyl)amino]benzenesulfonate;

4-methylphenyl 4-[({7-[({7-[({4-[(4-methylphenyl)oxysulfonyl]phenyl}amino)sulfonyl]-2-naphthyl}amino)carbonylamino]-2-naphthyl}sulfonyl)amino]benzenesulfonate;

7-[({7-[(pyrimidin-2-ylamino)sulfonyl]-2-naphthyl}amino)carbonylamino]naphthalene-2-sulfonic acid;

4-{[(7-{[N-(7-{[(4-sulfophenyl)amino]sulfonyl}-2-naphthyl)carbamoyl]amino}-2-naphtyl)-sulfonyl]amino}benzenesulfonic acid;

methyl 4-({[7-({N-[7-({[4-(methoxycarbonyl)phenyl]amino}sulfonyl)-2-naphthyl]carbamoyl}amino)-2-naphthyl]sulfonyl}amino)benzoate;

4-{[(7-{[N-(7-{[(4-carboxyphenyl)amino]sulfonyl}-2-naphthyl)carbamoyl]amino}-2naphthyl)-sulfonyl]amino}benzoic acid;

methyl (2S)-2-({[7-({N-[7-({[(1S)-2-(4-hydroxyphenyl)-1-(methoxycarbonyl)ethyl]amino}sulfonyl)(2-naphthyl)]carbamoyl}amino)(2-naphthyl)]sulfonyl}amino)-3-(4-hydroxyphenyl)propanoate; and (2S)-2-({[7-({N-[7-({[(1S)-1-carboxy-2-(4-hydroxyphenyl)ethyl]amino}sulfonyl)(2-naphthyl)]carbamoyl}amino)(2-naphthyl)]sulfonyl}amino)-3-(4-hydroxyphenyl)propanoic acid;

and their pharmaceutically acceptable salts, as single stereoisomers or mixtures of stereoisomers.

Syntheses and descriptions of these compounds are outlined in Examples 1 through 10 below.

Certain compounds of the invention may contain one or more chiral centers. In such cases, all stereoisomers also fall within the scope of this invention. The invention compounds include the individually isolated stereoisomers as well as mixtures of such stereoisomers.

The compounds of the invention further comprise pharmaceutically acceptable salts of the compounds disclosed herein. These pharmaceutically acceptable salts are suitable for use in all methods and pharmaceutical compositions of the present invention.

Pharmaceutically acceptable salts include salts which may be formed when acidic protons present are capable of reacting with inorganic or organic bases. Typically the parent compound is treated with an excess of an alkaline reagent, such as hydroxide, carbonate or alkoxide, containing an appropriate cation. Cations such as $Na^+$, $K^+$, $Ca^{2+}$ and $NH_4^+$ are examples of cations present in pharmaceutically acceptable salts. The $Na^+$ salts are especially useful. Acceptable inorganic bases, therefore, include calcium hydroxide, potassium hydroxide, sodium carbonate and sodium hydroxide. Salts may also be prepared using organic bases, such as ethanolamine, diethanolamine, triethanolamine, N-methylglucamine, ethanolamine, and tromethamine.

If a compound of the invention contains a basic group, an acid addition salt may be prepared. Acid addition salts of the compounds are prepared in a standard manner in a suitable solvent from the parent compound and an excess of an acid, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, hexanoic acid, heptanoic acid, cyclopentanepropionic acid, lactic acid, o-(4-hydroxy-benzoyl)benzoic acid, 1,2-ethanedisulfonic acid, 2-hydroxyethanesulfonic acid, benzenesulfonic acid, p-chlorobenzenesulfonic acid, 2-naphthalenesulfonic acid, camphorsulfonic acid, 4-methyl-bicyclo[2.2.2.]oct-2-ene-1-carboxylic acid, glucoheptonic acid, gluconic acid, 4,4'-methylenebis(3-hydroxy-2-naphthoic)acid, 3-phenylpropionic acid, trimethylacetic acid, t-butylacetic acid, laurylsulfuric acid, glucuronic acid, glutamic acid, 3-hydroxy-2-naphthoic acid, stearic acid, muconic acid and the like.

Certain of the compounds of the invention form inner salts or zwitterions.

The invention includes pharmaceutical compositions of all the compounds of the present invention. These pharmaceutical compositions comprise (i) a compound of the invention as an active ingredient and (ii) a pharmaceutically acceptable carrier.

Pharmaceutical compositions of the compounds of this invention, or derivatives thereof, may be formulated as solutions or lyophilized powders for parenteral administration. Powders may be reconstituted by addition of a suitable diluent or other pharmaceutically acceptable, carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration, but may also be used for oral administration. It may be desirable to add excipients such as polyvinylpyrrolidinone, gelatin, hydroxycellulose, acacia, polyethylene glycol, mannitol, sodium chloride or sodium citrate. Alternatively, these compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the, conventional techniques of pharmacy involving milling, mixing, granulation, and compressing, when necessary, for tablet forms; or milling, mixing and filling for hard gelatin capsule forms. When a liquid carrier is use, the preparation will be in the form of a syrup, elixir, emulsion or an aqueous or non-aqueous suspension. Such a liquid formulation may be administered directly p.o. or filled into a soft gelatin capsule. On a percent by weight basis, typical pharmaceutical compositions may contain from 0.1 to 95% of active ingredient, more preferably 1 to 80%.

Some specific examples of suitable pharmaceutical compositions are described in Example 25 below.

Typically, a pharmaceutical composition of the present invention would be packaged in a container with a label indicating use of the pharmaceutical composition in the treatment of hyperglycemia, type I diabetes, and type II diabetes, or a combination of any of these disease conditions. Compounds can be prophylactically administered prior to a meal to control excessive elevated glucose in type II diabetics for a period of time following the meal. Alternatively, the compounds can be administered to a diabetic to normalize excessively elevated glucose levels as measured by glucose monitoring device. Finally, it is known that the very small amount of residual circulating insulin found in type I diabetics is used by the body to prevent severe lipolysis and the resulting keto-acidosis. These compounds can be used to prophylactically against ketoacidosis in type I patient. Administration of these compounds could provide relief from ketoacidosis via insulin receptor activation, not for control of blood sugar, but for inhibition of severe lipolysis in type I diabetics who do not have ready access to insulin.

(c) Methods of Use of the Compounds of the Present Invention

Figure 11:
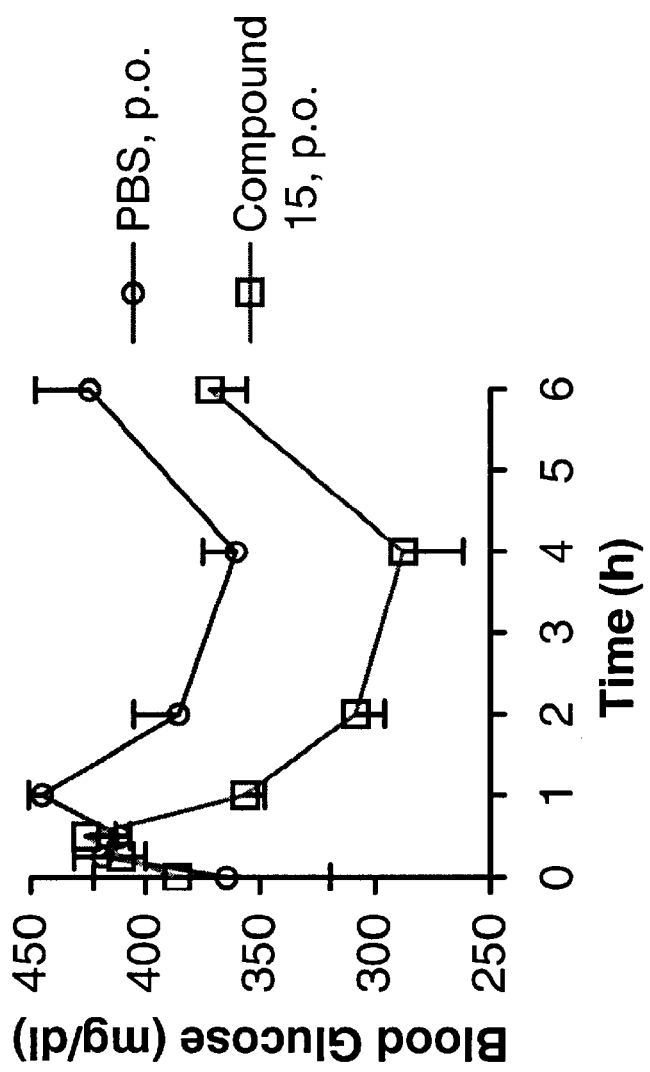
FIG. 11 shows the effect of Compound 15 on blood glucose levels in a STZ/BFD rat.

Compounds of the present invention have been found to stimulate autophosphorylation of the insulin receptor (Example 11 and 12, below). In addition, these compounds have been shown to enhance insulin's ability to effect the transport of glucose into cultured fibroblast cells (Example 13, below). The compounds have also been shown to lower blood glucose levels in db/db mice in an insulin independent manner (FIGS. 8 and 9, Example 17; FIG. 11, Example 19).

The ability of the compounds of this invention to stimulate autophosphorylation of the insulin receptor and to stimulate the uptake of glucose into cells which is demonstrated in the specific examples 11–24 below, indicates their usefulness in the treatment and management of subjects with diabetes. Without intending to be bound by any theory, it is believed that the compounds of the invention act directly on the kinase function of the insulin receptor and do not necessarily compete with insulin for binding at the insulin-binding site, nor do they effect activation of the receptor by a mechanism similar to that exhibited by insulin. Thus, they are able directly to activate the kinase to autophosphorylate, to potentiate the effect of insulin, to activate the kinase function of the receptor in phosphorylating exogenous substrates and to effect the increased uptake of glucose by adipocytes and insulin receptor-bearing cells in general and to lower blood glucose in diabetic subjects. Accordingly, by virtue of the activities of the compounds of the invention, they may be used to stimulate the kinase activity of an insulin receptor, to enhance the activation of the insulin receptor by insulin, to enhance the stimulation by insulin of cellular glucose uptake, and to stimulate the uptake of glucose in diabetic subjects. Thus, the compounds of this invention are useful in the treatment of hyperglycemia and diabetes in mammals.

One aspect of the invention is directed to a method of stimulating the kinase activity of the insulin receptor. This method comprises contacting the insulin receptor, or the kinase portion thereof, with a compound of the invention in an amount sufficient to stimulate the kinase activity of the insulin receptor. By stimulating the kinase activity of the insulin receptor, both autophosphorylation as well as the phosphorylation of exogenous substrates is enhanced. The stimulation of the kinase activity of the insulin receptor may occur either in vivo or in vitro. The method of stimulating the kinase activity of the insulin receptor may optionally further comprise also contacting the insulin receptor with insulin.

The compounds of the invention have been demonstrated to exhibit stimulatory activity at the insulin receptor with subsequent lowering of circulating glucose levels for a potential therapeutic effect in diabetes illness. Similarly, other compounds which show the same effects on the insulin receptor and, thus, on circulating glucose have the potential to be useful for the treatment of diabetes diseases. The compounds of this invention can be used as a model to discover other new agents that act on the insulin receptor and thereby lower circulating levels of glucose in diabetic patients. The steps in a process in which these agents can be utilized to discover new insulin receptor agonists/activators and glucose-lowering therapeutic agents may be achieved by the following. The compounds may be utilized to validate, optimize, and standardize assays necessary for the discovery of other compounds that:

1. Activate/stimulate the cytoplasmic kinase domain of the insulin receptor kinase or the insulin receptor kinase;
2. Activate/stimulate the insulin receptor;
3. Stimulate glucose uptake in to cells and tissues;
4. Lower circulating glucose levels in mammals;
5. Lower circulating glucose levels in humans;
6. Inhibit lipolysis in cells and tissues;
7. Inhibit lipolysis in mammals.

These compounds can be utilized as a bench mark to discover compounds that show improved activity in assays that:

1. Activate/stimulate the cytoplasmic kinase domain of the insulin receptor kinase or the insulin receptor kinase;
2. Activate/stimulate the insulin receptor;
3. Stimulate glucose uptake in to cells and tissues;

4. Lower circulating glucose levels in mammals;
5. Lower circulating glucose levels in humans;
6. Inhibit lipolysis in cells and tissues;
7. Inhibit lipolysis in mammals.

Combined with algorithms that compare structures or chemical properties and/or match structures or chemical properties within libraries of test compounds, these compounds can be utilized to discover compounds that display activity in bioassays that:

1. Activate/stimulate the cytoplasmic kinase domain of the insulin receptor kinase or the insulin receptor kinase.;
2. Activate/stimulate the insulin receptor;
3. Stimulate glucose uptake in to cells and tissues;
4. Lower circulating glucose levels in mammals;
5. Lower circulating glucose levels in humans;
6. Inhibit lipolysis in cells and tissues;
7. Inhibit lipolysis in mammals.

Combined with algorithms that compare structures and/or match structures for the purpose of modeling molecular interactions, these compounds can be utilized to discover compounds that display activity in bioassays that:

1. Activate/stimulate the cytoplasmic kinase domain of the insulin receptor kinase or the insulin receptor kinase;
2. Activate/stimulate the insulin receptor;
3. Stimulate glucose uptake in to cells and tissues;
4. Lower circulating glucose levels in mammals;
5. Lower circulating glucose levels in humans;
6. Inhibit lipolysis in cells and tissues;
7. Inhibit lipolysis in mammals.

Radioactive compounds of this invention can be used to diagnose diabetes, because there is a decrease in the number of insulin receptors in patients with type II diabetes and even in patients displaying pre-diabetic risk factors such as Syndrome-X. A simple tissue biopsy followed by exposure of the tissue sample to these radioactive compounds can yield a measure of the receptor count for the biopsy tissue. A low receptor density count can then be used to diagnose diabetes or pre-diabetes in the patient.

Radioactive compounds have a long history of use in the discovery of new drugs. The compounds of this invention all have the potential to be easily radiolabeled and can be used to discover other new agents that act on the insulin receptor and thereby lower circulating levels of glucose in diabetic patients. The process in which these agents can be utilized to discover new insulin receptor agonists/activators and glucose-lowering therapeutic agents are as follows:

Radioactive compounds of this invention can be utilized to validate, optimize, and standardize bioassays used for discovery of other compounds that:

1. Activate/stimulate the cytoplasmic kinase domain of the insulin receptor kinase or the insulin receptor kinase;
2. Activate/stimulate the insulin receptor;
3. Stimulate glucose uptake in to cells and tissues;
4. Lower circulating glucose levels in mammals;
5. Lower circulating glucose levels in humans;
6. Inhibit lipolysis in cells and tissues;
7. Inhibit lipolysis in mammals.

Radioactive compounds of this invention can be utilized as a bench mark to discover compounds that show improved activity in bioassays that:

1. Activate/stimulate the cytoplasmic kinase domain of the insulin receptor kinase or the insulin receptor kinase;
2. Activate/stimulate the insulin receptor;
3. Stimulate glucose uptake in to cells and tissues;
4. Lower circulating glucose levels in mammals;
5. Lower circulating glucose levels in humans;
6. Inhibit lipolysis in cells and tissues;
7. Inhibit lipolysis in mammals;

In another embodiment of the invention, the insulin receptor is activated by contacting the insulin receptor, or the kinase portion thereof, with a compound of the invention in an mount sufficient to activate the insulin receptor. The targeted insulin receptor may optionally be on the surface of a cell in a mammal. In such a case, the contacting is effected by administering the compound, or a pharmaceutical composition thereof, to the mammal. Optionally, the method may further comprise contacting the insulin receptor with insulin.

In an alternative embodiment, the compounds of the invention are used to stimulate the uptake of glucose into cells displaying the insulin receptor. This method comprises contacting the cells with a compound of the invention, optionally in the presence of insulin, and in an amount sufficient to stimulate the uptake of glucose into the cells. The targeted cells may optionally be in a mammal and the step of contacting the receptor with the compound may then be effected by administering the compound, or pharmaceutical composition thereof, to the mammal. In one embodiment of the method of stimulating the uptake of glucose into cells displaying the insulin receptor, the cells are also contacted with exogenous insulin.

A method of treating hyperglycemia in a mammal, preferably a human, is also contemplated by the present invention. The methods comprises administering a therapeutically effective amount of a compound of this invention, or a pharmaceutical composition thereof, to a mammal. Optionally, the method may further comprise treating the mammal with one or more additional forms of therapy or treatment for hyperglycemia. For instance, one method may comprise administering exogenous insulin to the mammal in addition to the compound of the invention. Alternatively, the compounds of the invention may be administered to the mammal in combination with a non-insulin drug or other alternative treatment for hyperglycemia. The total amount of the combination of drugs administered to the mammal must be a therapeutically effective amount, although the amounts of each of the individual drugs may by themselves be suboptimal for therapeutic purposes.

A very dangerous side-effect of the administration of insulin is insulin-induced hypoglycemia with the potential for coma and, possibly, death. This problem can become quite severe in diabetic patients who develop unpredictable responses to insulin or have hyper-variable levels of circulating glucose. For these patients, the co-administration of these compounds with sub-therapeutic doses of insulin will minimize the possibility that the diabetic patient will overdose on insulin and suffer from the severe consequences such as coma and death. These compounds appear to be incapable of inducing hypoglycemia in the presence or absence of insulin. They appear to increase the effectiveness of insulin, but do not display true insulin mimetic effects like hypoglycemia. These compounds are, thus, effective insulin safeners.

In one embodiment of the invention, the compounds are used to treat type I diabetes in a mammal. This method comprises administering a therapeutically effective amount of a compound of this invention, or a pharmaceutical composition thereof, to the mammal. In a preferred embodiment, the mammal is a human. The method of treating type I diabetes may optionally further comprise treating the mammal with one or more additional therapies or treatments for type I diabetes. For instance, in one embodiment of the method of treating type I diabetes, a compound of the invention and insulin may both be administered to the mammal. Alternatively, the additional form of treatment for type I diabetes which is combined with administration of the compound of the invention may be an antidiabetic agent other than insulin or another alternative form of treatment for type I diabetes. Again, the total amount of the combination of antidiabetic agents administered to the mammal must be a therapeutically effective amount, although the amounts of each of the individual drugs may be sub-optimal for therapeutic purposes if those drugs were to be delivered alone to the, mammal with type I diabetes.

In another embodiment of the invention, the compounds of the invention are used to treat type II diabetes in a mammal. This method comprises administering a therapeutically effective amount of a compound of this invention, or a pharmaceutical composition thereof, to the mammal. Again, the preferred subject is a human.

Again, like the other treatment methods of the invention, this method may further comprise treating the mammal with one or more additional forms of therapy for type II diabetes, such as administering insulin to the mammal. The insulin is delivered to the mammal in an amount which is therapeutically effective when used in conjunction with a compound of the invention. This therapeutically effective amount of insulin when used in combination with a compound of the invention may be less than the amount of insulin which would be therapeutically effective if delivered to the mammal alone. It is understood that the insulin which is administered in any of the treatments of the present invention may either be isolated from a natural source or be recombinant. In addition, an insulin analog may be substituted for insulin in any of the treatments of the present invention.

Use of the compounds of the invention for treating type II diabetes by combination therapy may also comprise the administration of the compound of the invention to the mammal in combination with a non-insulin, antidiabetic agent or other treatment for type II diabetes. For instance, the antidiabetic drug which is administered to the mammal in combination with a compound of the invention may optionally be a thiazolidinedione, such as troglitazone, or a sulfonylurea. The total amount of the combination of drugs (invention compound plus insulin, and/or other antidiabetic drug) administered to the mammal for the treatment of type II diabetes must be a therapeutically effective amount, although the amount of each of the individual drugs used in the combination therapy may be suboptimal for therapeutic purposes if that drug were to be delivered alone to the mammal with type II diabetes.

The compounds of this invention are thus used to enhance glucose uptake in patients which require such treatment. The method of treatment comprises the administration parenterally, and orally, of an effective quantity of the chosen compound of the invention, preferably dispersed in a pharmaceutical carrier. Dosage units of the active ingredient are generally selected from the range of 0.01 to 1000 mg/kg, preferably 0.01 to 100 mg/kg and more preferably 0.1 to 50 mg/kg, but will be readily determined by one skilled in the art depending upon the route of administration, age and condition of the patient. The compounds of the invention are most preferably administered in a dosage unit of 1 to 10 mg/kg. These dosage units may be administered one to ten times daily for acute or chronic disease. No unacceptable toxicological effects are expected when compounds of the invention are administered in accordance with the present invention.

The invention compounds may be administered by any route suitable to the subject being treated and the nature of the subject's condition. Routes of administration include, but are not limited to, administration by injection, including intravenous, intraperitoneal, intramuscular, and subcutaneous injection, by transmucosal or transdermal delivery, through topical applications, nasal spray, suppository and the like or may be administered orally. Formulations may optionally be liposomal formulations, emulsions, formulations designed to administer the drug across mucosal membranes or transdermal formulations. Suitable formulations for each of these methods of administration may be found, for example, in *Remington's Pharmaceutical Sciences,* latest edition, Mack Publishing Company, Easton, Pa.

Methods, uses, activities, administration, and pharmaceutical compositions delineated above for the compounds of the invention are preferred for those compounds in which K=O.

(d) EXAMPLES

The Examples which follow serve to illustrate this invention. The Examples are in no way intended to limit the scope of this invention, but are provided to show how to make and use the compounds of this invention.

The compounds of formula I may be prepared by:
(i) intermolecular or intramolecular condensation of a compound of the formula

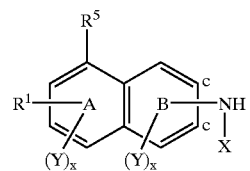

with a compound of the formula

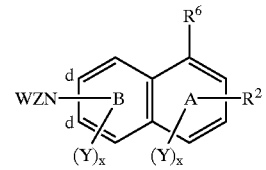

or the addition of one of these compounds to the other, where the amino groups of the compounds are optionally in a protected form, with an activated bifunctional reagent that provides the group K=C—, where K has the above meaning; where $R^1$, $R^2$, $R^3$, $R^4$, $R^5$, $R^6$, x, and Y are defined according to the first aspect of the Summary of the Invention, X may be $R^3$ or $R^4$, and WZ may be S=C= or O=C=, or W and Z may be $R^3$ or $R^4$;

to form a linker between the two compounds and prepare a compound of Formula I;

(ii) chemical elaboration of one or more substituents $R^3$, $R^2$, $R^5$, and $R^6$ or Y, where said substituent is convertible into another substituent;

(iii) introduction of a substituent $R^1$, $R^2$, $R^5$, and $R^6$ or Y into one or both of the naphthalene rings;

(iv) deprotection;

(v) elaboration of the linker to convert said linker into another linker;

(vi) salt formation or interconversion;

(vii) ester hydrolysis;

(viii) liberation of a free acid or base of a compound of claim 1; or (ix) stereoisomer separation or synthesis.

Details are apparent from the following table, which shows typical reactions for steps (i) through (viii).

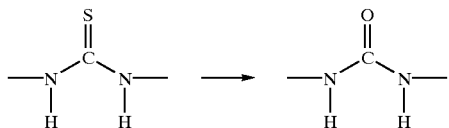

In a condensation reaction, a simple substance, such as. water, is released by the combination of two or more molecules. The condensation reaction may occur upon addition of any of a number of starting materials utilized in organic syntheses, such as dibromoethane and diiodopropane, at a temperature between 50 and 125 C. Should $R^3$ and $R^4$ in the formulae above together be —(CH$_2$)$_2$, —(CH$_2$)$_3$—, or (CH$_2$)$_4$—, then the condensation is intramolecular (see Reaction Scheme VI).

Chemical elaboration of one or more substituents $R_1$, $R^2$, $R^5$, and $R^6$ or Y via the conversion of one such substituent into another substituent may be accomplished via hydrolysis, salt formation, acidification, alkylation, esterification, oxidation, or reduction. In hydrolysis, an ester or amide compound is dissociated by reaction with water. Hydrolysis is catalyzed by acid or base, and hydrolysis of an amide generally requires more vigorous conditions (for example, a higher concentration of sulfuric acid at 1 to 100 C for 1 to hours) than those required for the hydrolysis of esters. Hydrolysis reactions can also be carried out with aqueous hydrochloric acid at 100 to 150 C. and may require as long as 18 hours.

In salt formation, a free acid is converted into a salt via addition of a basic reagent, such as aqueous sodium hydroxide or triethanolamine, that replaces all or part of the hydrogen ions of the acid with one or more cations of a base.

The conversion of a compound into its corresponding acid addition salt is accomplished via treatment with a stoichiometric amount of an appropriate acid, such as hydrochloric acid. Typically, the free base is dissolved in a polar organic solvent, such as methanol or ethanol, and the acid is added in methanol or ethanol. The temperature is maintained at 0 to 50 C. The corresponding salt precipitates spontaneously or can be brought out of solution with a less polar solvent. In acidification, a chemical compound is converted into an acid.

In alkylation, an alkyl group is added to or substituted in a compound. Alkylation is carried out in a suitable solvent, such as acetonitrile, DMF, or THF, at 0 to 160 C., typically at approximately 25 C. to reflux, and requires some 1 to 18 hours. Finally, an esterification reaction results in the formation of at least one ester product. In brief, the compound is reacted with from 1.0 to 5.0, preferable 2.0, molar equivalents of an alkanol, a thiol or ammonia, a monoalkylamine, or dialkylamine, or a heterocyclic aminoalkanol, optionally in the presence of from 1.0 to 1.5, preferably 1.25, molar equivalents of a tertiary organic base such as 4-dimethylaminopyridine or, preferably, triethylamine, in an organic solvent such as dioxane, tetrahydrofuran, or, preferably, dichloromethane. The reaction takes place at −10 to 50 C., preferably at ambient temperature, for 1 to 24 hours, preferably 4 hours.

Certain compounds of formula I can be prepared via acid addition. Furthermore, the compounds of formula I may be prepared by modifying K (where K has the above meaning), for example, by alkylating K, followed by amino substitution, in which an amino group replaces, for example, a leaving group such as the S-methyl group.

In those cases in which protective groups may be introduced and finally removed, suitable protective groups for amino, hydroxy, carboxyl groups are as described in Greene, et al., *Protective Groups in Organic Synthesis,* Second Edition, John Wiley and Sons, New York, 1991. Activation of carboxylic acids can be achieved by using a number of different reagents as described in Larock, *Comprehensive Organic Transformations,* VCH Publishers, New York, 1989.

Example 1

Compounds 3, 4, 8–16, and 19–93 were prepared according to Reaction Scheme I and Reaction Scheme II.

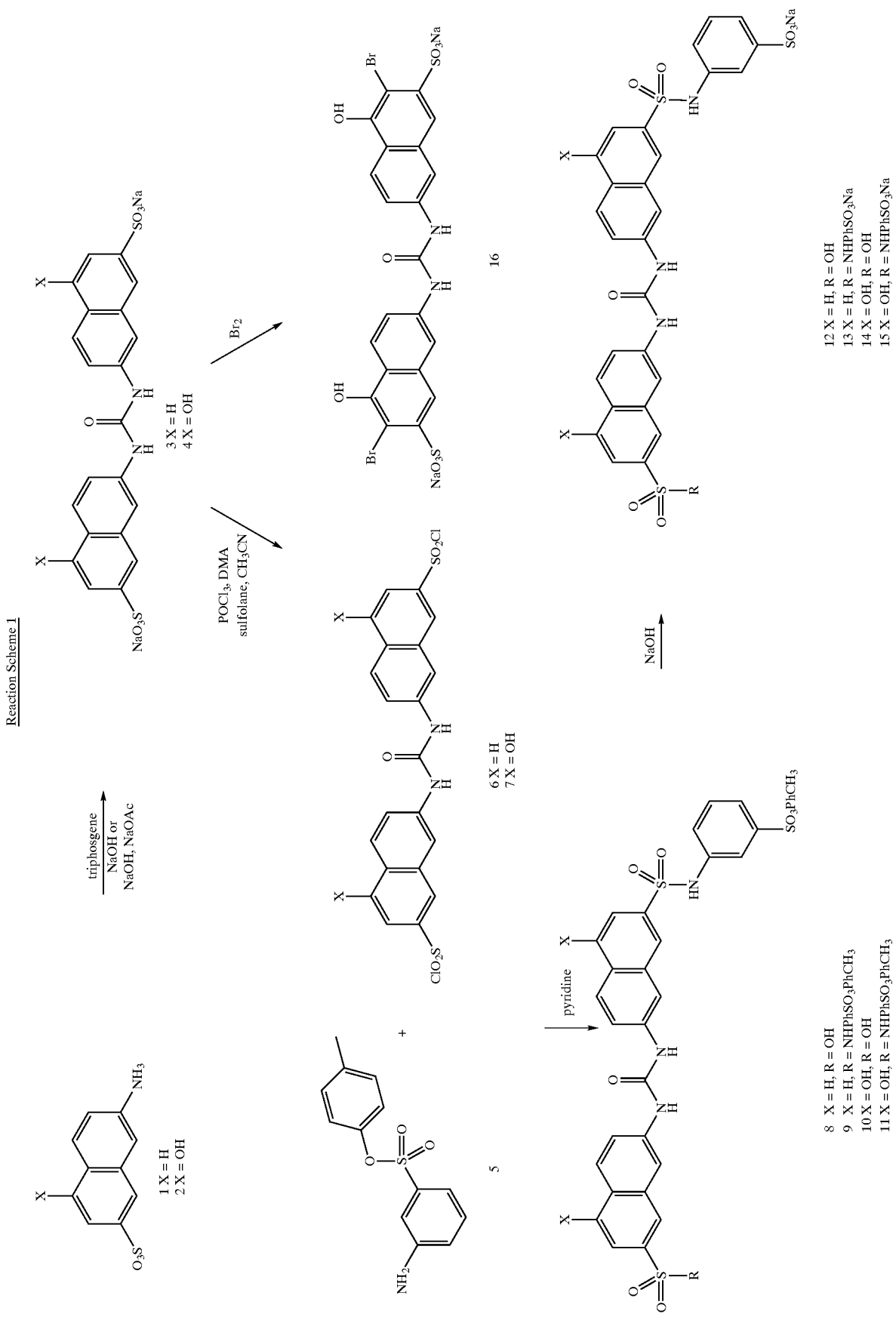

7-{[(7-sulfo-2-naphthyl)amino]carbonylamino}naphthalene-2-sulfonic acid disodium salt (Compound 3)

To 5.25 g (0.021 mol) of 7-amino-naphthalene-2-sulfonic acid suspended in 80 mL of water was added a solution of 6.5 mL of 10 N aqueous NaOH (0.065 mol) diluted to 30 mL with water and a solution of 3.20 g (0.011 mol) of triphosgene in 30 mL of THF portionwise, and alternating such that the pH of the reaction was maintained above 8. After the reaction was complete by TLC (6:2:1 ethyl acetate:isopropanol:water) the pH was lowered to 1 with aqueous HCl and the volatiles were removed by rotary evaporation. The solid product was collected by vacuum filtration and was washed with water. This afforded 3.41 g of compound 3.

4-hydroxy-7-{[(5-hydroxy-7-sulfo(2-naphthyl))amino]carbonylamino}naphthalene-2-sulfonic acid disodium salt (Compound 4)

To 10.77 g (0.045 moles) of 7-amino-4-hydroxynaphthalene-2-sulfonic acid dissolved in 45 mL of 1 N aqueous NaOH and 50 mL of water was added 3.70 g (0.045 moles) of sodium acetate. The pH of the solution was above 9. The reaction was cooled to under 5° C. in an ice-water bath. Then, 2.23 g (0.045 mole) of triphosgene dissolved in mL of THF was added in three portions. The pH of the reaction fell to 4–5 and was readjusted to 7–8 by the dropwise addition of 1N aqueous NaOH. TLC (6:2:1 ethyl acetate:isopropanol:water) indicated the reaction was incomplete. Another 2.20 grams (0.045 moles) of triphosgene in 10 mL of THF was added portionwise with the pH kept above 7 by the addition of 1N aqueous NaOH. When the reaction was judged complete by TLC, the pH was lowered to 1 with aqueous HCl and the volatiles were removed by rotary evaporation. The solid product was collected by vacuum filtration. This afforded 10.85 g of compound 4.

4-methylphenyl 3-aminobenzenesulfonate (Compound 5)

To 50 g (0.463 mole) of p-cresol (4-methylphenol) and 37 mL (0.458 mole) of pyridine dissolved in 250 mL of chloroform was added 50 g (0.226 mole) of 3-nitrobenzenesulfonyl chloride. The reaction was allowed to stir at ambient temperature. After 2 hours, the reaction was judged complete by TLC and the volatiles were removed by rotary evaporation. The resulting residue was treated with 400 mL of 0.5 M sodium bicarbonate. The insoluble product was collected and washed with sodium bicarbonate (2 times, 200 mL each) and water (2 times, 300 mL each). The solid was then treated with methanol (200 mL) followed by water (200 mL). The solid was collected by vacuum filtration and washed with water. This solid was treated with 170 g (0.897 mole) of tin (II) chloride dissolved in 250 mL of concentrated HCl. The reaction was allowed to stir at ambient temperature for 40 hours. TLC indicated that the reaction was incomplete, so the reaction was heated at 50 C. for 27 hours. The solid precipitate was collected by vacuum filtration and was washed with 6N HCl. The solid was extracted with ethyl acetate and, water. The ethyl acetate layer was washed with brine, dried with magnesium sulfate, filtered, and the volatiles removed by rotary evaporation to yield 42.5 g of compound as an oil that solidified on standing.

N-[7-(chlorosulfonyl)(2-naphthyl)]{[7-(chlorosulfonyl)(2-naphthyl)]amino}carboxamide (Compound 6)

To 2.35 g (4.86 mmol) of compound 3 was added 116 mL of sulfolane, 25 mL of acetonitrile, 31 mL of phosphorus oxychloride, and 1 mL of dimethylacetamide. The reaction was allowed to stir for 72 hours at ambient temperature. This produced a nearly clear solution. The reaction was poured onto 1.5 L of ice and the flask placed in an ice bath. After all the ice had melted, the solid was collected by vacuum filtration and was washed with water. The solid was dried under high vacuum for 24 hours. This provided 2.56 g of compound 6.

7-{[(7-(chlorosulfonyl)-5-hydroxy(2-naphthyl))amino]carbonylamino}-4-hydroxynaphthalene-2-sulfonyl chloride (Compound 7)

To 500 mg (0.912 mmol) of compound 4 suspended in 8 mL of phosphorous oxychloride was added 25 mL of 1:1 (v:v) sulfolane:acetonitrile and 0.5 mL of dimethylacetamide. The reaction mixture was allowed to stir at ambient temperature for 16 hours. The reaction became a clear solution which was poured onto 500 mL of ice. The ice mixture was placed in an ice bath and allowed to warm to room temperature. The resulting solid was collected by vacuum filtration and was washed with water. The solid was dried under high vacuum for 24 hours. This provided 412 mg of compound 7.

7-[({7-[({3-[(4-methylphenyl)oxysulfonyl]phenyl}amino)sulfonyl]-2-naphthyl}amino)carbonylamino]naphthalene-2-sulfonic acid (compound 8) and 4-methylphenyl 3-[({7-[(N-{7-[({3-[(4-methylphenyl)oxysulfonyl]phenyl}amino)sulfonyl]-2-naphthyl}carbamoyl)amino]-2-naphthyl}sulfonyl)amino]benzenesulfonate (Compound 9)

To 250 mg (0.95 mmol) 4-methylphenyl 3-aminobenzenesulfonate (compound 5). Dissolved in 40 mL of pyridine was added a solution of 250 mg (0.49 mmol) of compound 6 in 5 mL of THF. The reaction was allowed to stir at ambient temperature for 3 hours. Then, the reaction was extracted with ethyl acetate and 1 N HCl. The ethyl acetate layer was dried with magnesium sulfate, filtered, and the volatiles were removed by rotary evaporation. The products were purified by reverse-phase (RP) HPLC (C18, 30×250 mm column) using trifluoroacetic acid (TFA) buffer system (Buffer A: 5% acetonitrile, 95% water, 0.05% TFA; Buffer B: 95% acetonitrile, 5% water, 0.05% TFA; 35 mL/min, 0–100% B in 45 min.). Fractions containing the earlier eluting compound were combined and lyophilized to provide 9 mg of compound 8. Fractions containing the later eluting compound were combined and lyophilized to provide 51 mg of compound 9.

4-hydroxy-7-[({5-hydroxy-7-[({3-[(4-methylphenyl)oxysulfonyl]phenyl}amino)sulfonyl](2-naphthyl)}amino)carbonylamino]naphthalene-2-sulfonic acid (compound 10) and 4-methylphenyl 3-[({4-hydroxy-7-[(N-{5-hydroxy-7-[({3-[(4-methylphenyl)oxysulfonyl]phenyl}amino)sulfonyl](2-naphthyl)}carbamoyl)amino]-2-naphthyl}sulfonyl)amino]benzenesulfonate (Compound 11)

To 250 mg (0.95 mmol) 4-methylphenyl 3-aminobenzenesulfonate (compound 5) dissolved in 40 mL of pyridine was added a solution of 265 mg (0.49 mole) of compound 7 in 5 mL of THF. The reaction was allowed to stir at ambient temperature for 3 hours. Then, the reaction was extracted with ethyl acetate and 1 N HCl. The ethyl acetate layer was dried with magnesium sulfate, filtered, and the volatiles were removed by rotary evaporation. The products were purified by reverse-phase HPLC (C18, 30×250 mm column) using trifluoroacetic acid (TFA) buffer system (Buffer A: 5% acetonitrile, 95% water, 0.05% TFA; Buffer B: 95% acetonitrile, 5% water, 0.05% TFA; 35 mL/min, 0–100% B in 60 min.). Fractions containing the earlier eluting compound were combined and lyophilized to provide 15 mg of compound 10. Fractions containing the later eluting compound were combined and lyophilized to provide 65 mg of compound 11.

7-{[(7-{[(3-sulfophenyl)amino]sulfonyl}-2-naphthyl)amino]carbonylamino}naphthalene-2-sulfonic acid disodium salt (Compound 12)

To 8 mg ( 0.011 mmol) of compound 8 was added 2 mL of 5 N NaOH. The reaction was allowed to stir at ambient temperature for 6 hours. The reaction was acidified with 6 N HCl and the solution was added to a small reverse-phase (C18) solid phase extraction column. The column was washed with $H_2O$ followed by 50:50 (v:v) $CH_3CN:H_2O$ to elute the product. This provided 5 mg of compound 12.

3-{[(7-{[N-(7-{[(3-sulfophenyl)amino]sulfonyl}-2-naphthyl)carbamoyl]amino}-2-naphthyl)sulfonyl]amino}benzenesulfonic acid disodium salt (Compound 13)

To 35 mg ( 0.036 mmol) of compound 9 was added 2 mL of 5 N NaOH. The reaction was allowed to stir at ambient temperature for 6 hours. The reaction was acidified with 6 N HCl and the solution was added to a small reverse-phase (C18) solid phase extraction column. The column was washed with $H_2O$ followed by 50:50 (v:v) $CH_3CN:H_2O$ to elute the product. This provided 26 mg of compound 13.

4-hydroxy-7-{[(5-hydroxy-7-{[(3-sulfophenyl)amino]sulfonyl}(2-naphthyl))amino]carbonylamino}naphthalene-2-sulfonic acid (Compound 14)

This compound was prepared from compound 10 according to the procedure described for the synthesis of compound 12.

3-{[(4-hydroxy-7-{[N-(5-hydroxy-7-{[(3-sulfophenyl)amino]sulfonyl}(2-naphthyl))carbamoyl]amino}-2-naphthyl)sulfonyl]amino}benzenesulonic acid (Compound 15)

This compound was prepared from compound 11 according to the procedure described for the synthesis of compound 12.

3-bromo-7-{[(6-bromo-5-hydroxy-7-sulfo(2-naphthyl))amino]carbonylamino}-4-hydroxynaphthalene-2-sulfonic acid disodium salt (Compound 16)

To a solution of 123 mg (0.22 mmol) of compound 4 in 1 mL of water and 2 mL of dioxane was added 300 μL of a 1 M solution of bromine in carbon tetrachloride. After 1 hour, another 200 μL of the bromine solution was added to the reaction. After another hour, an additional 150 μL of the bromine solution was added to the reaction. After 30 minutes, the reaction was poured into 100 mL of THF to produce a brown precipitate that was collected by vacuum filtration. The desired product was purified by silica gel column chromatography (5:2:1 ethyl acetate:isopropanol:water) to provide 17 mg of compound 16.

Example 2

An alternative synthetic method for the compounds of the invention is described in Reaction Scheme II. This method was useful for the synthesis of larger quantities of the desired products and is illustrated by the synthesis of compound 15.

Reaction Scheme II

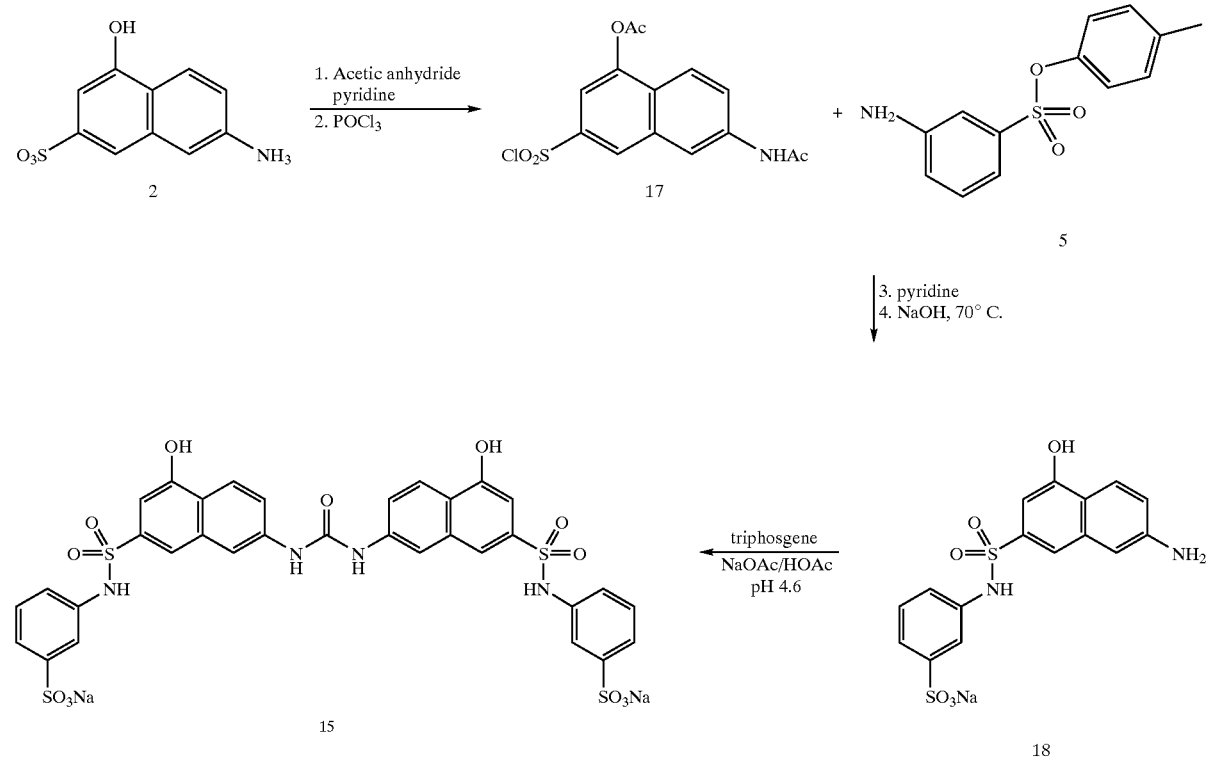

6-(acetylamino)-3-(chlorosulfonyl)naphthyl acetate
(Compound 17)

To 50 g (0.209 mmol) of compound 2 was added 100 mL of acetic anhydride and 100 mL of pyridine. The reaction was allowed to stir at ambient temperature for 16 hours. The solid precipitate was collected by vacuum filtration. This provided 83 g of product that was dried under high vacuum. To this solid was added 260 mL of phosphorous oxychloride. This suspension was allowed to stir at ambient temperature for 16 hours. Then, the dark solution was poured onto 3 L of ice. After all the ice had melted (about 3 hours), the solid was collected by vacuum filtration and washed with water. The solid was dried in vacuo to provide 50 g of compound 17.

3-{[(7-amino-4-hydroxy-2-naphthyl)sulfonyl]amino}benzenesulfonic acid sodium salt
(Compound 18)

To 25 g (0.095 mol) of compound 5 dissolved in 200 mL of THF was added 8.1 mL of pyridine. Then, 36.3 g (0.106 mol) of compound 17 was added followed by an additional 200 mL of THF. The reaction was allowed to stir at ambient temperature for 16 hours. Then, the volatiles were removed and the resulting residue was partitioned between ethyl acetate and 1N HCl. The ethyl acetate layer was washed with brine, treated with magnesium sulfate, filtered and the volatiles removed by rotary evaporation. The resulting solid was dissolved in 220 mL of 5N NaOH and 30 mL of dioxane. The solution was heated at 80 C. for hours. Then, the pH of the solution was lowered to 1 with concentrated HCl. The solid was collected by vacuum filtration and then dissolved in 200 mL of water with 20 mL of 5 N NaOH. The solution was heated to give a hazy solution that was filtered hot to produce a clear solution. The solution was diluted with water to 1.5 L and then the pH was adjusted to 1 with 6 N HCl. A solid precipitate formed. The suspension was cooled in the refrigerator overnight and the solid was collected by vacuum filtration to furnish, after drying, 21 g of compound 18.

3-{[(4-hydroxy-7-{[N-5-hydroxy-7-{[(3-sulfophenyl)amino]sulfonyl}(2-naphthyl))carbamoyl]-amino}-2-naphthyl)sulfonyl]amino}benzenesulfonic acid disodium salt
(Compound 15)

To 17.7 g (0.045 mol) of compound 18 was added 250 mL of acetate buffer (1M NaOAc/HOAc, pH 4.6) and 50 mL of THF. This formed a dark brown solution. A solution of 4.4 g (mmol) of triphosgene in 40 mL of THF was added dropwise to the above solution over a period of 3 hours and 10 min. HPLC indicated the reaction was complete. The reaction was acidified with concentrated HCl (15 mL). All the volatiles were removed by rotary evaporation, and the resulting goo was stripped from acetonitrile, acetonitrile/heptane, and then heptane. The resulting solid was dissolved in 140 mL of water with heating. Then, 250 mL of brine was added. A solid precipitate formed. The flask was kept at 4 C. for 15 hours, and then the solid was collected by vacuum filtration. The solid was washed with a small amount of ice-cold 3:1 water:brine. After drying under high vacuum, this provided 19.2 g of compound 15.

The following compounds (Table 1) were prepared according to the same general procedures as those outlined in Reaction Scheme I or Reaction Scheme II and detailed in the above procedures for the synthesis of compounds 3–18. The variety of molecules that were used in place of compound 5 for the synthesis of compounds 19–91 were either purchased from commercial suppliers or were prepared by standard methods known to those skilled in the art. Compounds in Table 1 with acidic groups are shown in the free acid form.

TABLE 1

| Compound | $R^0$ | $R^5$ | $R^6$ | $R^{00}$ | Y |
|---|---|---|---|---|---|
| 3 | OH | H | H | OH | H |
| 4 | OH | OH | OH | OH | H |
| 8 | OH | H | H | (3-[(4-methylphenoxy)sulfonyl]phenylamino) | H |

TABLE 1-continued

| Compound | R⁰ | R⁵ | R⁶ | R⁰⁰ | Y |
|---|---|---|---|---|---|
| 9 | -NH-C₆H₄-SO₂-O-C₆H₄-CH₃ (m-sulfonyl-p-tolyl ester anilide) | H | H | -NH-C₆H₄-SO₂-O-C₆H₄-CH₃ | H |
| 10 | OH | OH | OH | -NH-C₆H₄-SO₂-O-C₆H₄-CH₃ | H |
| 11 | -NH-C₆H₄-SO₂-O-C₆H₄-CH₃ | OH | OH | -NH-C₆H₄-SO₂-O-C₆H₄-CH₃ | H |
| 12 | OH | H | H | -NH-C₆H₄-SO₃H | H |
| 13 | -NH-C₆H₄-SO₃H | H | H | -NH-C₆H₄-SO₃H | H |
| 14 | OH | OH | OH | -NH-C₆H₄-SO₃H | H |
| 15 | -NH-C₆H₄-SO₃H | OH | OH | -NH-C₆H₄-SO₃H | H |
| 16 | OH | OH | OH | OH | Br |

TABLE 1-continued

[Structure: bis-naphthalene urea with R⁵, R⁶, Y substituents and sulfonyl R⁰/R⁰⁰ groups]

| Compound | R⁰ | R⁵ | R⁶ | R⁰⁰ | Y |
|---|---|---|---|---|---|
| 19 | OH | H | H | -NH-C₆H₄-SO₂-O-C₆H₄-CH₃ (p-tolyl ester) | H |
| 20 | OH | H | H | -NH-C₆H₄-SO₂-OH | H |
| 21 | -NH-C₆H₄-SO₂-O-C₆H₄-CH₃ | H | H | -NH-C₆H₄-SO₂-O-C₆H₄-CH₃ | H |
| 22 | -NH-C₆H₄-SO₂-OH | H | H | -NH-C₆H₄-SO₂-OH | H |
| 23 | -NH-C₆H₄(m)-SO₂-NH₂ | H | H | -NH-C₆H₄(m)-SO₂-NH₂ | H |
| 24 | -NH-C₆H₄-C(O)-OMe | H | H | -NH-C₆H₄-C(O)-OMe | H |
| 25 | -NH-C₆H₄-C(O)-OH | H | H | -NH-C₆H₄-C(O)-OH | H |
| 26 | OH | OH | OH | -NH-C₆H₄-C(O)-OMe | H |
| 27 | -NH-C₆H₄-C(O)-OMe | OH | OH | -NH-C₆H₄-C(O)-OMe | H |

TABLE 1-continued

| Compound | R⁰ | R⁵ | R⁶ | R⁰⁰ | Y |
|---|---|---|---|---|---|
| 28 | OH | OH | OH | HN–C₆H₄–COOH (para) | H |
| 29 | HN–C₆H₄–COOH (para) | | OH | OH | HN–C₆H₄–COOH (para) | H |
| 30 | OH | H | H | HN–C₆H₃(OH)–COOH (2-OH, 3-NH) | H |
| 31 | HN–C₆H₃(OH)–COOH (2-OH, 3-NH) | H | H | HN–C₆H₃(OH)–COOH (2-OH, 3-NH) | H |
| 32 | OH | H | H | HN–C₆H₃(OH)–COOH (5-NH, 2-OH, 1-COOH) | H |
| 33 | HN–C₆H₃(OH)–COOH (5-NH, 2-OH, 1-COOH) | H | H | HN–C₆H₃(OH)–COOH (5-NH, 2-OH, 1-COOH) | H |
| 34 | OH | H | H | HN–C₆H₃(OH)–COOH (4-NH, 2-OH, 1-COOH) | H |
| 35 | HN–C₆H₃(OH)–COOH (4-NH, 2-OH, 1-COOH) | H | H | HN–C₆H₃(OH)–COOH (4-NH, 2-OH, 1-COOH) | H |
| 36 | OH | H | H | HN–C₆H₃(NO₂)–COOMe (5-NH, 2-NO₂, 1-COOMe) | H |

TABLE 1-continued
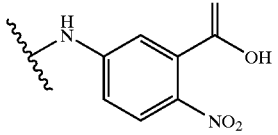
| Compound | R⁰ | R⁵ | R⁶ | R⁰⁰ | Y |
|---|---|---|---|---|---|
| 37 | OH | H | H | 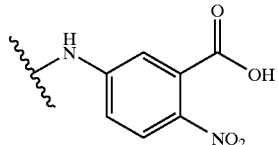 | H |
| 38 | 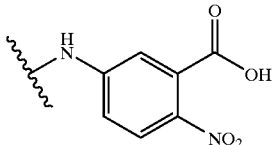 | H | H | 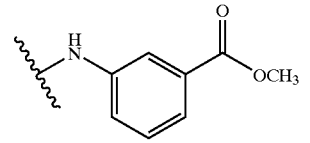 | H |
| 39 | 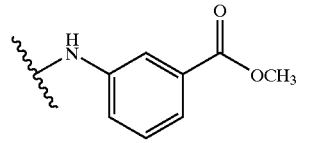 | H | H | 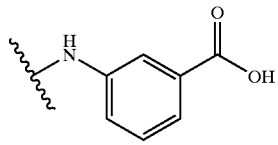 | H |
| 40 | 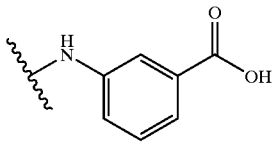 | H | H | 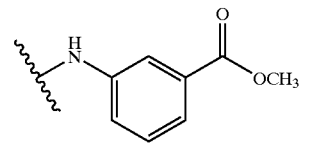 | H |
| 41 | 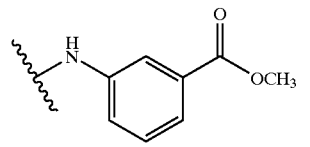 | OH | OH | 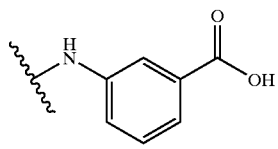 | H |
| 42 | 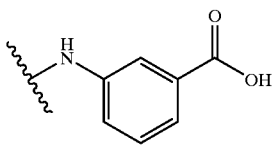 | OH | OH | 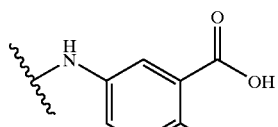 | H |
| 43 | 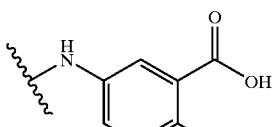 | OH | OH | 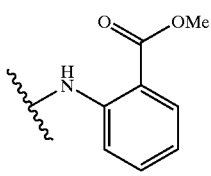 | H |
| 44 | 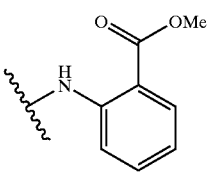 | H | H |  | H |

TABLE 1-continued
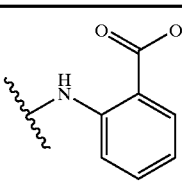
| Compound | R⁰ | R⁵ | R⁶ | R⁰⁰ | Y |
|---|---|---|---|---|---|
| 45 | 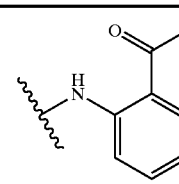 | H | H | 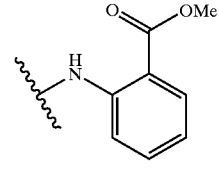 | H |
| 46 | 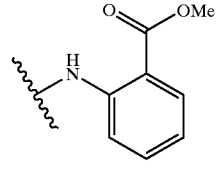 | OH | OH | 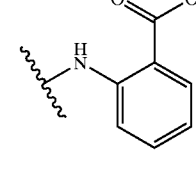 | H |
| 47 | 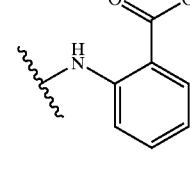 | OH | OH | 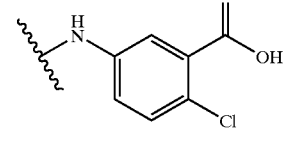 | H |
| 48 | 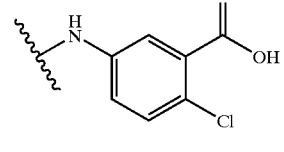 | H | H | 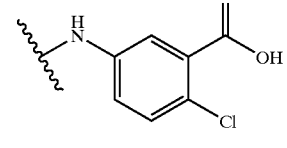 | H |
| 49 | 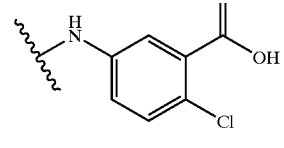 | OH | OH | 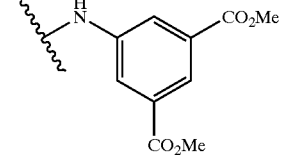 | H |
| 50 | 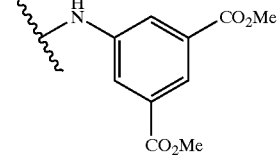 | OH | OH | 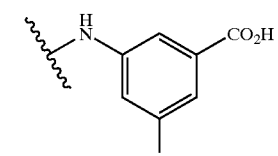 | H |
| 51 | 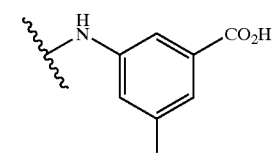 | OH | OH | 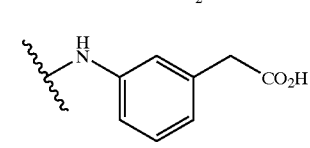 | H |
| 52 | 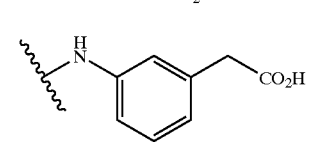 | OH | OH | | H |

TABLE 1-continued
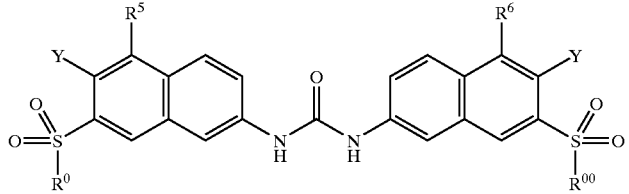
| Compound | R⁰ | R⁵ | R⁶ | R⁰⁰ | Y |
|---|---|---|---|---|---|
| 53 | 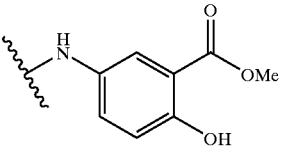 | H | H | 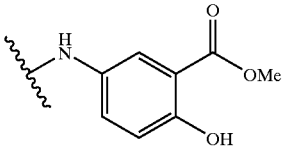 | H |
| 54 | 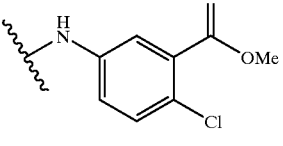 | H | H | 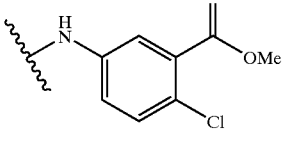 | H |
| 55 | 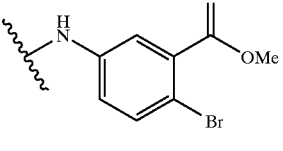 | H | H | 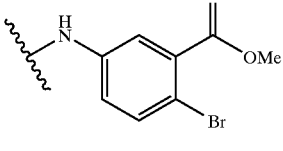 | H |
| 56 | 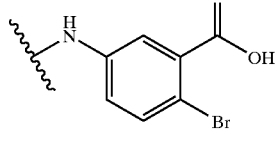 | H | H | 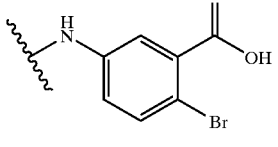 | H |
| 57 | 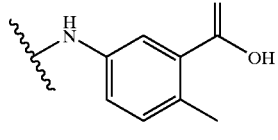 | H | H | 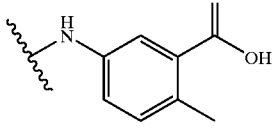 | H |
| 58 | 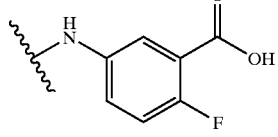 | H | H | 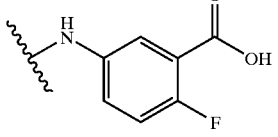 | H |
| 59 | 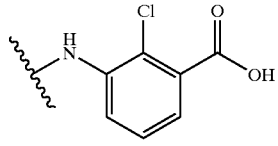 | OH | OH | 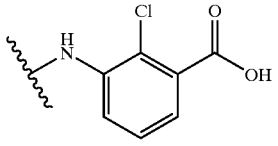 | H |
| 60 | 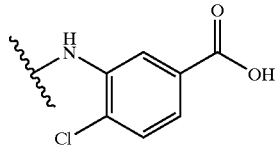 | OH | OH | 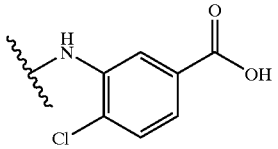 | H |

TABLE 1-continued

| Compound | R⁰ | R⁵ | R⁶ | R⁰⁰ | Y |
|---|---|---|---|---|---|
| 61 | 5-NH-, 2-OMe, benzoate methyl ester | H | H | 5-NH-, 2-OMe, benzoate methyl ester | H |
| 62 | 5-NH-, 2-OMe, benzoic acid | H | H | 5-NH-, 2-OMe, benzoic acid | H |
| 63 | 3-NH-, 4-OH, benzoate methyl ester | H | H | 3-NH-, 4-OH, benzoate methyl ester | H |
| 64 | 3-NH-, 4-OH, benzoic acid | H | H | 3-NH-, 4-OH, benzoic acid | H |
| 65 | 3-NH-, 4-OMe, benzoate methyl ester | H | H | 3-NH-, 4-OMe, benzoate methyl ester | H |
| 66 | 3-NH-, 4-OMe, benzoic acid | H | H | 3-NH-, 4-OMe, benzoic acid | H |
| 67 | 3-NH-phenyl-tetrazole | H | H | 3-NH-phenyl-tetrazole | H |
| 68 | 3-NH-phenyl-tetrazole | OH | OH | 3-NH-phenyl-tetrazole | H |

TABLE 1-continued

| Compound | R⁰ | R⁵ | R⁶ | R⁰⁰ | Y |
|---|---|---|---|---|---|
| 69 | 4-(1H-tetrazol-5-yl)phenyl-NH– | OH | OH | 4-(1H-tetrazol-5-yl)phenyl-NH– | H |
| 70 | 3-(diethoxyphosphoryl)phenyl-NH– | H | H | 3-(diethoxyphosphoryl)phenyl-NH– | H |
| 71 | 3-(ethoxy(hydroxy)phosphoryl)phenyl-NH– | H | H | 3-(ethoxy(hydroxy)phosphoryl)phenyl-NH– | H |
| 72 | OH | H | H | Tyr-OMe | H |
| 73 | OH | H | H | Tyr-OH | H |
| 74 | Tyr-OMe | H | H | Tyr-OMe | H |

TABLE 1-continued

| Compound | R⁰ | R⁵ | R⁶ | R⁰⁰ | Y |
|---|---|---|---|---|---|
| 75 | NH-CH(CH₂-C₆H₄-OH)-COOH (tyrosine) | H | H | NH-CH(CH₂-C₆H₄-OH)-COOH (tyrosine) | H |
| 76 | NH-phenyl | H | H | NH-phenyl | H |
| 77 | NH-(pyridin-3-yl) | H | H | NH-(pyridin-3-yl) | H |
| 78 | OH | H | H | NH-(pyrimidin-2-yl) | H |
| 79 | NH-(pyrimidin-2-yl) | H | H | NH-(pyrimidin-2-yl) | H |
| 80 | NH-(pyrazin-2-yl) | H | H | NH-(pyrazin-2-yl) | H |
| 81 | NH-(3-hydroxyphenyl) | H | H | NH-(3-hydroxyphenyl) | H |
| 82 | NH-(3-hydroxymethylphenyl) | OH | OH | NH-(3-hydroxymethylphenyl) | H |
| 83 | NH-(3-cyanophenyl) | H | H | NH-(3-cyanophenyl) | H |

TABLE 1-continued

| Compound | R⁰ | R⁵ | R⁶ | R⁰⁰ | Y |
|---|---|---|---|---|---|
| 84 | -NH-(3-nitrophenyl) | H | H | -NH-(3-nitrophenyl) | H |
| 85 | -NH-(5-(hydroxymethyl)-4-chlorophenyl) | H | H | -NH-(5-(hydroxymethyl)-4-chlorophenyl) | H |
| 86 | -NH-(3-chloro-4-hydroxyphenyl) | H | H | -NH-(3-chloro-4-hydroxyphenyl) | H |
| 87 | -NHCH₂-(3,4-dihydroxyphenyl) | H | H | -NHCH₂-(3,4-dihydroxyphenyl) | H |
| 88 | -NH-(3-trifluoromethylphenyl) | OH | OH | -NH-(3-trifluoromethylphenyl) | H |
| 89 | NH₂ | H | H | NH₂ | H |
| 90 | OH | H | H | -NH-(3-sulfo-4-chlorophenyl) | H |
| 91 | -NH-(3-sulfo-4-chlorophenyl) | H | H | -NH-(3-sulfo-4-chlorophenyl) | H |
| 92 | OH | OH | OH | -NH-(3-sulfo-4-chlorophenyl) | H |

TABLE 1-continued

| Compound | R⁰ | R⁵ | R⁶ | R⁰⁰ | Y |
|---|---|---|---|---|---|
| 93 | ⁓N(H)-C₆H₃(Cl)-SO₂-OH | OH | OH | ⁓N(H)-C₆H₃(Cl)-SO₂-OH | H |

Example 3

The compounds 94–102 were synthesized according to the procedures outlined in Reaction Scheme III.

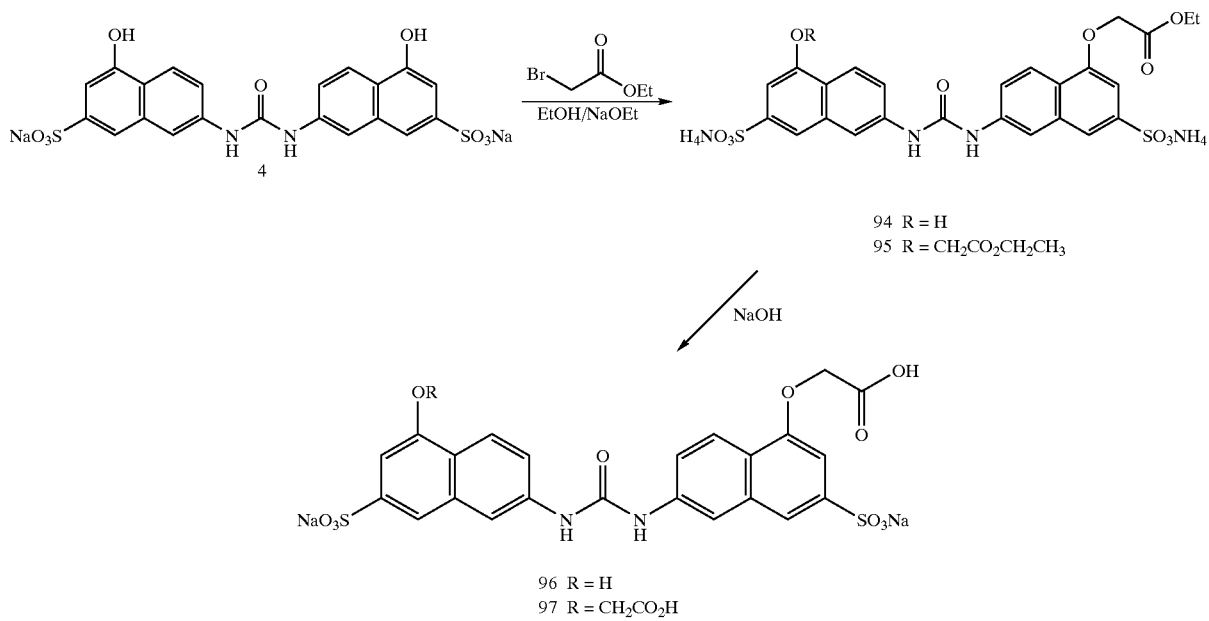

Reaction Scheme III

94 R = H
95 R = CH₂CO₂CH₂CH₃

96 R = H
97 R = CH₂CO₂H

7-[({5-[(ethoxycarbonyl)methoxy]-7-sulfo(2-naphthyl)}amino)carbonylamino]-4-hydroxynaphthalene-2-sulfonic acid, diammonium salt (Compound 94) and 4-[(ethoxycarbonyl)methoxy]-7-[((5-[(ethoxycarbonyl)methoxy]-7-sulfo(2-naphthyl)}amino)-carbonylamino]naphthalene-2-sulfonic acid, diammonium salt (Compound 95)

To 275 mg (0.5 mmol) of compound 4 suspended in 50 mL of ethanol was added 2.5 mL of a 0.2M solution of sodium ethoxide in ethanol. Then, 56 μL (0.5 mmol) of ethyl bromoacetate was added. The mixture was stirred and refluxed for 2 hours. Then, the solid was removed by filtration and the volatiles were removed from the filtrate to provide 220 mg of crude product. The products were purified by reverse-phase HPLC (C18, 20×250 mm column) using ammonium acetate ($NH_4OAc$) buffer system (Buffer A: 5% acetonitrile, 95% water, 50 mM $NH_4OAc$; Buffer B: 70% acetonitrile, 30% water, 15 mM $NH_4OAc$; 15 mL/min, 0–100% B in 30 min.). Fractions containing the earlier eluting compound were combined and lyophilized to provide 60 mg of compound 94. Fractions containing the later eluting compound were combined and lyophilized to provide 32 mg of compound 95.

2-(6-{[N-(5-hydroxy-7-sulfo(2-naphthyl)carbamoyl]amino}-3-sulfonaphthyloxy)acetic acid disodium salt (Compound 96)

To 25 mg (0.04 mmol) of compound 94 was added 1 ML of 5 N NaOH. The solution was allowed to stir for 18 hours at ambient temperature. The pH was lowered to 1 with aqueous HCl and the resulting solid was collected by vacuum filtration to afford 16 mg of compound 96.

2-[6-({N-[5-(carboxymethoxy)-7-sulo(2-naphthyl)]carbamoyl}amino)-3-sulfonaphthyloxy]acetic acid disodium salt (Compound 97)

Compound 95 was treated as above for compound 94 to provide 11 mg of compound 97.

The following compounds (Table 2) were prepared according to the same general procedures as those outlined in Reaction Scheme III and detailed in the above procedures for the synthesis of compounds 94–97. The variety of molecules that were used in place of ethyl bromoacetate for the synthesis of compounds 98–102 were either purchased from commercial suppliers or were prepared by standard methods known to those skilled in the art. All of the compounds in Table 2 are shown in the free acid form.

TABLE 2

| Compound | $R^0$ | $R^5$ | $R^6$ | $R^{00}$ |
|---|---|---|---|---|
| 94 | OH | OH | O-CH₂-CO₂Et | OH |
| 95 | OH | O-CH₂-CO₂Et | O-CH₂-CO₂Et | OH |
| 96 | OH | OH | O-CH₂-CO₂H | OH |
| 97 | OH | O-CH₂-CO₂H | O-CH₂-CO₂H | OH |
| 98 | OH | OH | OCH₃ | OH |
| 99 | OH | OCH₃ | OCH₃ | OH |
| 100 | OH | SO₃H | SO₃H | OH |
| 101 | OH | OH | O-(CH₂)₃-SO₃H | OH |
| 102 | OH | O-(CH₂)₃-SO₃H | O-(CH₂)₃-SO₃H | OH |

Example 4

The compounds 103–105 were synthesized according to the procedure outlined in Reaction Scheme IV.

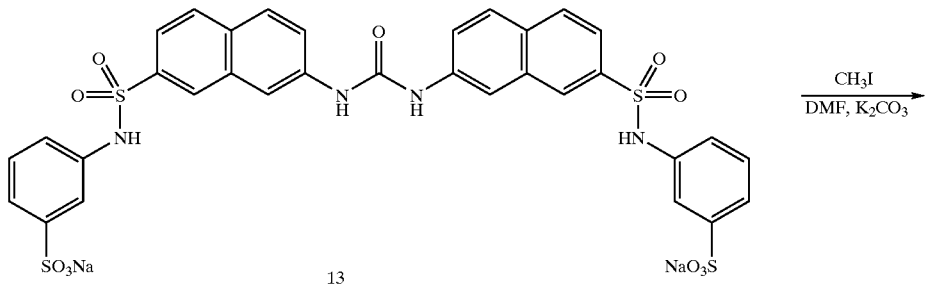

Reaction Scheme IV

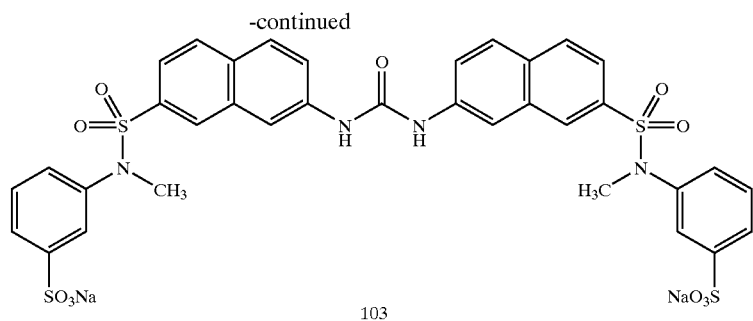

103

3-{methyl[(7-{[(7-{[methyl(3-sulfophenyl)amino] sulfonyl}(2-naphthyl))amino]-carbonylamino}(2-naphthyl))sulfonyl]amino}benzenesulfonic acid dipotassium salt (Compound 103)

To 59 mg (0.071 mmol) of compound 13 was added 2 mL of DMF. Then, 38 mg of potassium carbonate was added. The stirred suspension was heated at 70 C. in an oil bath. Then, 36 μL of iodomethane was added. The reaction was heated for 3 hours, and then the volatiles were removed by rotary evaporation. The resulting solid was dissolved in water and added to a C18 solid phase extraction column. The column was washed with 9 column volumes of water. The product was eluted with 80% acetonitrile to furnish, after evaporation of the volatiles, 55 mg of compound 103.

Compounds 104 and 105 (Table 3) were prepared by the same general procedure as indicated above for the synthesis of compound 103 except that allyl bromide was used in place of methyl iodide and compound 48 was used in place of compound 13. Compounds in Table 3 with acidic groups are shown in the free acid form.

TABLE 3

| Compound # | $R^I$ | $R^{II}$ | $R^{III}$ | $R^{IV}$ |
|---|---|---|---|---|
| 103 | 3-sulfophenyl | $CH_3$ | $CH_3$ | 3-sulfophenyl |
| 104 | 2-chloro-5-(allyloxycarbonyl)phenyl | $CH_2CH=CH_2$ | $CH_2CH=CH_2$ | 2-chloro-5-(allyloxycarbonyl)phenyl |
| 105 | 2-chloro-5-carboxyphenyl | $CH_2CH=CH_2$ | $CH_2CH=CH_2$ | 2-chloro-5-carboxyphenyl |

Example 5

The compounds 112–114 and 116 were synthesized according to procedures outlined in Reaction Scheme V.

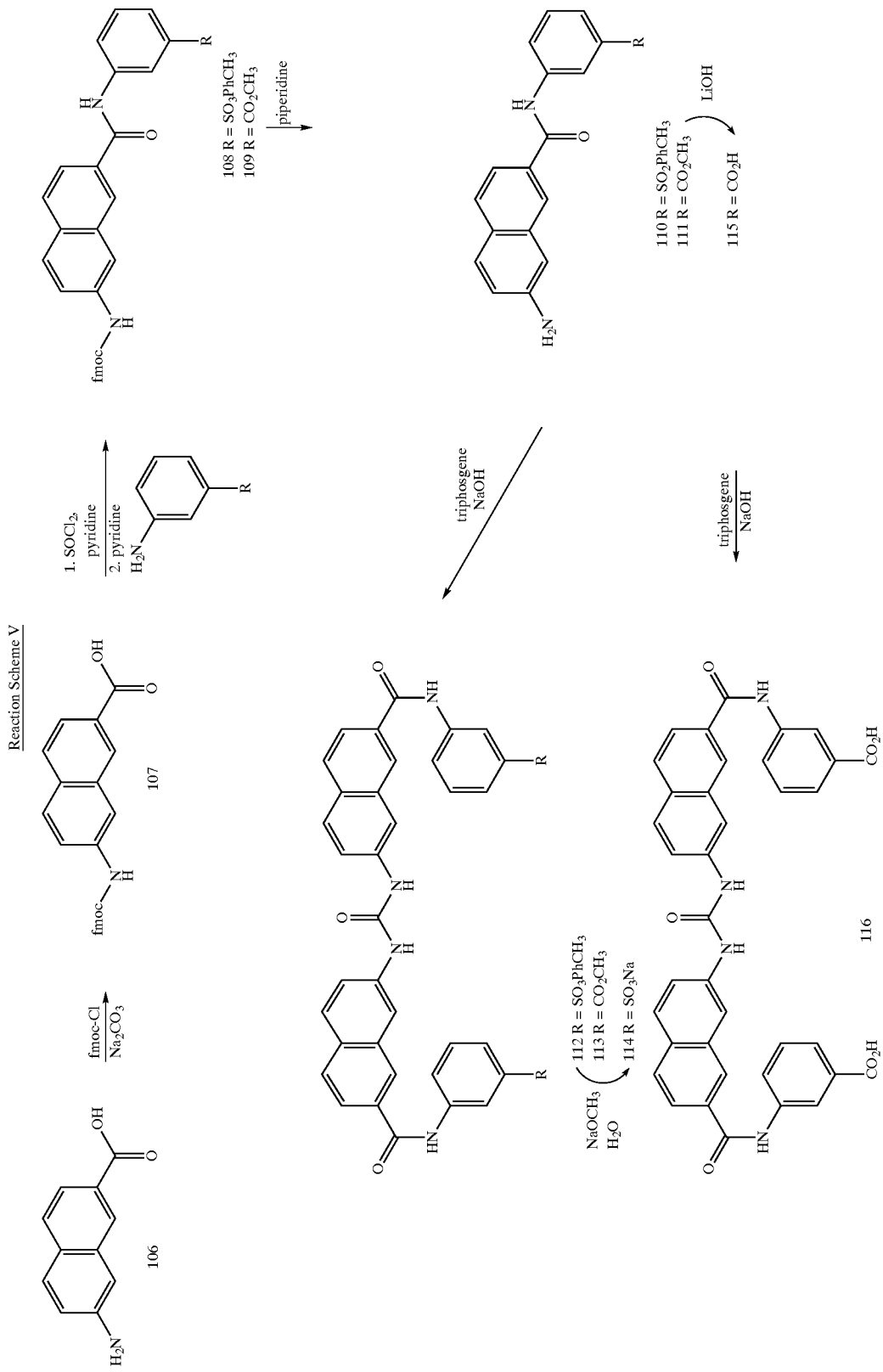

7-(fluoren-9-yloxycarbonylamino)naphthalene-2-carboxylic acid (107)

To 0.504 g (2.70 mmol) of 7-aminonaphthalene-2-carboxylic acid (106; prepared according to the procedure in Harrison, H. A. and Royle, F. A. *J. Chem. Soc.,* 1926, 84) was added 10 mL of dioxane, 5 mL of 10% sodium carbonate, and 35 mL of water. To this clear solution was added 0.786 g (2.97 mmol) of 9-fluorenylmethyl chloroformate, portionwise, over 15 minutes. After 3 hours, the reaction was acidified with 1N HCl and the resulting white precipitate was collected by vacuum filtration. This solid was suspended in diethyl ether and stirred to give a fine precipitate that was collected by vacuum filtration. This provided 0.948 g of compound 107.

4-methylphenyl 3-{[7-(fluoren-9-yloxycarbonylamino)-2-naphthyl]carbonylamino}benzenesulfonate (Compound 108)

To 104 mg (0.026 mmol) of compound 107 was added 6.5 mL of chloroform, 1.3 mL of thionyl chloride, and 100 µL of pyridine. The reaction was allowed to stir at ambient temperature for 3 hours and then all volatiles were removed in vacuo. The residue was stripped in vacuo from chloroform twice. To the resulting solid, suspended in 15 mL of chloroform was added 74 mg (0.028 mmol) of 4-methylphenyl 3-aminobenzenesulfonate (compound 5) and 27 µL (0.033 mmol) of pyridine as a solution in 1.5 mL of chloroform. The reaction was allowed to stir at ambient temperature for 16 hours, after which it was partitioned between ethyl acetate and 1 N HCl (aqueous). The organic layer was dried (magnesium sulfate), filtered, and the volatiles were removed in vacuo. The resulting residue was treated with diethyl ether. and the solid precipitate collected by vacuum filtration. This provided 110 mg of compound 108.

4-methylphenyl 3-{[[(7-amino-2-naphthyl)sulfonyl]amino}benzenesulfonate (Compound 110)

To 104 mg (0.16 mmol) of compound 108 was added 9 mL of THF and 360 µL of piperidine. The resulting clear solution was allowed to stir for 6 hours. Then, the reaction was extracted with ethyl acetate and 1N HCl (aqueous). The dried organic layer (magnesium sulfate) was filtered and the volatiles removed in vacuo. The resulting residue was dissolved in dichloromethane and 3 mL of 1 N HCl in diethyl ether and 50 mL of diethyl ether were added to form a precipitate that was collected by centrifugation. After drying, this provided 75 mg of compound 110 as the hydrochloride salt.

4-methylphenyl 3-[({7-[(N-{7-[{(3-[(4-methylphenyl)oxysulfonyl]phenyl}amino)sulfonyl]-2-naphthyl}carbamoyl)amino]-2-naphthyl}sulfonyl)amino]benzenesulfonate (Compound 112)

To 75 mg (0.17 mmol) of compound 110 dissolved in 3 mL of THF and 1 mL of water was added, portionwise and alternating, a solution of 280 µL of 5 N NaOH (aqueous) in 1 mL of water followed by a solution of 54 mg (0.18 mmol) of triphosgene in 1 mL of THF. The volatiles were removed until a solid precipitate formed and a clear solution. The solution was decanted and the solid was dissolved in dichloromethane, and evaporated 3 times. This produced a dichloromethane insoluble product that was collected by vacuum filtration to provide 24 mg of compound 112.

3-{[(7-{[N-(7-{[(3-sulophenyl)amino]sulfonyl)-2-naphthyl)carbamoyl]amino}-2-naphthyl)sulfonyl]amino}benzenesulfonic acid disodium salt (Compound 114)

To 20 mg (0.02 mole) of compound 112 was added 1.5 mL of 1.37 M sodium methoxide in methanol, 1 mL of water, and 0.5 mL of THF. The resulting solution was allowed to stir at ambient temperature for 2 days. The reaction was acidified with 1 N HCl (aqueous) and the organic volatiles removed in vacuo. The solid precipitate was collected by vacuum filtration to afford 15 mg of compound 114.

methyl 3-({7-[fluoren-9-ylmethoxy)carbonylamino]-2-naphthyl}carbonylamino)benzoate (Compound 109)

To 305 mg (0.75 mmol) of compound 107 was added. 10 mL of chloroform, 3.5 mL of thionyl chloride, and 180 µL of pyridine. The reaction was allowed to stir at ambient temperature for three hours, followed by removal of volatiles by rotary evaporation. The resulting residue was stripped two times from chloroform. Then, 50 mL of chloroform, 124 mg (0.82 mmol) of methyl-3-aminobenzoate, and 100 µL of pyridine were added. The reaction was allowed to stir at ambient temperature for 16 hours. The reaction was extracted twice with 1N HCl (aqueous) and once with water. The dried organic layer (magnesium sulfate) was filtered and the volatiles removed by rotary evaporation. The resulting residue was treated with methanol to form a solid precipitate that was collected by vacuum filtration. This afforded 380 mg of compound 109.

methyl 3-[(7-amino-2-naphthyl)carbonylamino]benzoate (Compound 111)

To 380 mg (0.70 mmol) of compound 109 was added 30 mL of dichloromethane , 3 mL of THF and 1 mL of piperidine. The resulting clear solution was allowed to stir for 3 hours. Then, the reaction was extracted with ethyl acetate and 1N HCl (aqueous). The dried organic layer (magnesium sulfate) was filtered and the volatiles removed in vacuo. The resulting residue was dissolved in dichloromethane and 3 mL of 1 N HCl in diethyl ether and 50 mL of diethyl ether were added to form a precipitate that was collected by vacuum filtration. After drying, this provided 212 mg of compound 111 as the hydrochloride salt.

methyl 3-[(7-{[N-(7-{N-[3-(methoxycarbonyl)phenyl]carbamoyl}-2-naphthyl)carbamoyl]amino}-2-naphthyl)carbonylamino]benzoate (Compound 113)

To 21 mg (0.07 mmol) of compound 111 dissolved in 2 mL of THF and 1 mL of water was added, portionwise and alternating, a solution of 112 µL of 5 N NaOH (aqueous) in 1 mL of water followed by a solution of 28 mg (0.10 mmol) of triphosgene in 1 mL of THF. The reaction was acidified with 1N HCl and the volatiles were removed until a solid precipitate formed and a clear solution. The solid was collected by vacuum filtration to provide 21 mg of compound 113.

3-[(7-amino-2-naphthyl)carbonylamino]benzoic acid (Compound 115)

To 51 mg (0.16 mmol) of compound 111 was added 1 mL of methanol, 1 mL of water, and 800 μL of 1N lithium hydroxide (aqueous). The reaction was allowed to stir for 16 hours at ambient temperature. The pH of the solution was lowered to 3 with 1N HCl (aqueous) and the volatiles removed in vacuo. The resulting solid was suspended in water and collected by vacuum filtration. This provided 16 mg of compound 115.

3-({7-[(N-(7-[N-(3-carboxyphenyl)carbamoyl]-2-naphthyl}carbamoyl)amino]-2-naphthyl}carbonylamino)benzoic acid (Compound 116)

To 10 mg (0.03 mmol) of compound 115 dissolved in 2 mL of THF and 1 mL of water was added, portionwise and alternating, a solution of 40 μL of 5 N NaOH (aqueous) in 0.2 mL of water followed by a solution of 4 mg (0.02 mmol) of triphosgene in 0.2 mL of THF. The reaction was acidified with 1N HCl and the volatiles were removed in vacuo. The solid was collected by vacuum filtration to provide 9 mg of compound 116.

The compounds 112–114 and 116 that were prepared by the procedures described above are indicated in Table 4. Compounds with acidic groups are shown in the free acid form.

TABLE 4

| Compound | R |
|---|---|
| 112 | —SO$_3$PhCH$_3$ |
| 113 | —CO$_2$CH$_3$ |
| 114 | —SO$_3$H |
| 116 | —CO$_2$H |

Example 6

The compounds 122 and 123 were synthesized according to the procedures outlined in Reaction Scheme VI.

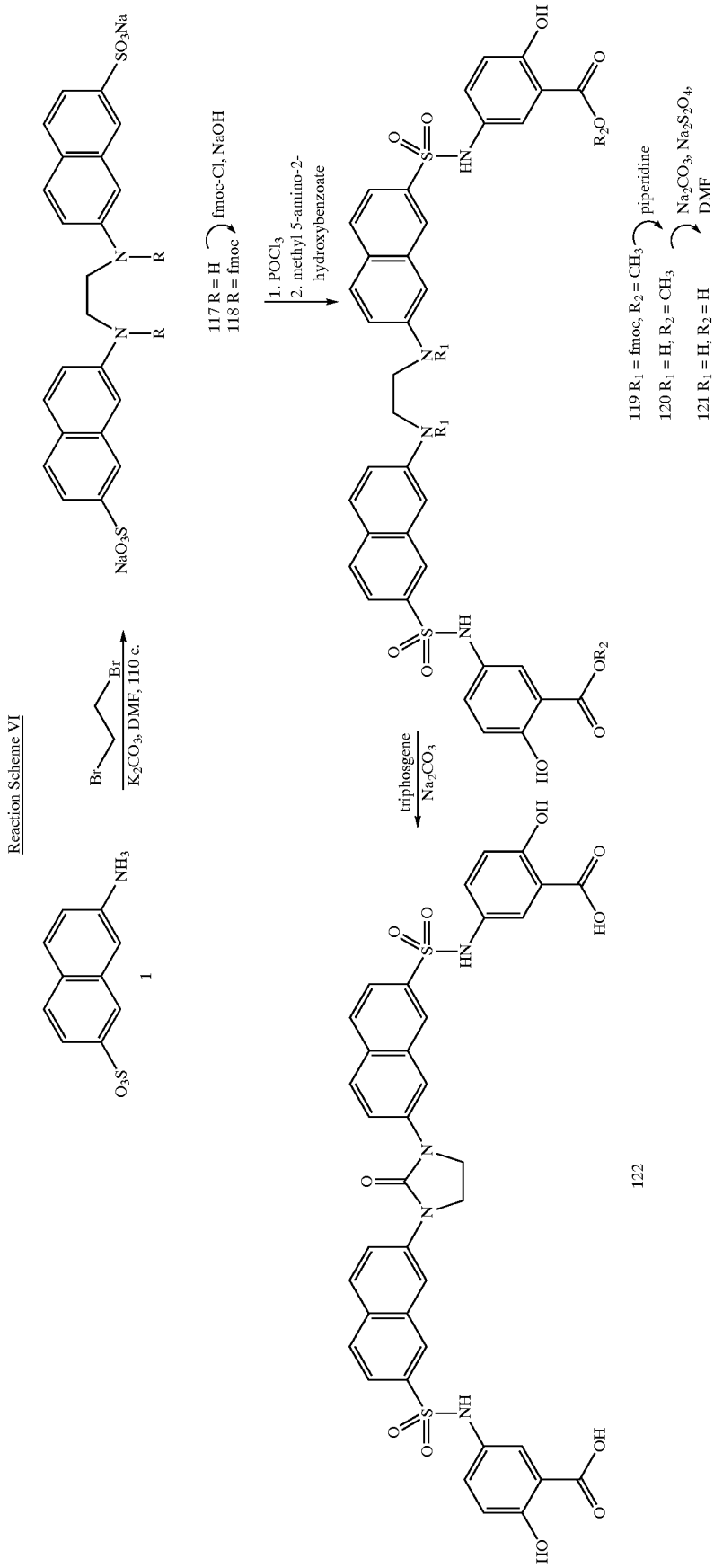
Reaction Scheme VI

7-({2-[(7-sulfo-2-naphthyl)amino]ethyl}amino) naphthalene-2-sulfonic acid, dipotassium salt (Compound 117)

To 2.04 g (9.15 mmol) of 7-amino-2-naphthalene sulfonic acid (compound 1) was added 50 mL of dry DMF. The stirred suspension was heated at 110 C. and then 1.4 g of potassium carbonate was added followed by 400 μL (4.6 mmol) of 1,2-dibromoethane. The reaction was kept at 110 C for 18 hours, and at 80 C. for an additional 18 hours. Then, the reaction was allowed to cool to ambient temperature. The resulting insoluble precipitate was collected by vacuum filtration and washed with methanol. The crude product was purified by silica gel column chromatography (6:2:1 ethyl acetate:isopropanol:water). This provided 596 mg of compound 117.

7-((fluoren-9-ylmethoxy)-N-{2-[(fluoren-9-ylmethoxy)-N-(7-sulfo(2-naphthyl))carbonylamino] ethyl}carbonylamino)naphthalene-2-sulfonic acid, disodium salt (Compound 118)

To 259 mg (0.47 mmol)of compound 117 was added 25 mL of water and 207 mg of sodium carbonate. Then, 20 mL of dioxane was added. To this stirred, hazy solution was added 290 mg (1.1 mmol) of 9-fluorenylmethyl chloroformate (FMOC-Cl) portionwise. After 2 hours, another 260 mg (1.0 mmol) of FMOC-Cl was added and the reaction was allowed to stir at ambient temperature for 12 hours. The volatiles were removed by rotary evaporation and the resulting solid was dissolved in water and lyophilized. This crude product was used without further purification.

methyl 5-[({7-[(fluoren-9-ylmethoxy)-N-(2-{(fluoren-9-ylmethoxy)-N-[7-({[4-hydroxy-3-(methoxycarbonyl)phenyl]amino}sulfonyl)(2-naphthyl)]carbonylamino}ethyl)carbonylamino](2-naphthyl))sulfonyl)amino]-2-hydroxybenzoate (Compound 119)

To all of the product compound 118 was added 15 mL of phosphorous oxychloride. This suspension was allowed to stir at ambient temperature for 24 hours. The yellow suspension was poured onto 700 mL of ice. After the ice melted, the yellow solid was collected by vacuum filtration and was washed with water.

The solid was dried in vacuo, overnight, to provide.194 mg of the intermediate disulfonyl chloride. To this solid was added 3 mL of THF followed by a solution of 72 mg (0.43 mmol) of methyl 5-amino-2-hydroxybenzoate and 41 μL of pyridine in 1.5 mL of THF. The reaction was allowed to stir at ambient temperature for 12 hours. The reaction was partitioned between ethyl acetate and 1N HCl. The organic layer was dried (MgSO$_4$), filtered, and the volatiles removed by rotary evaporation. The resulting solid was purified by silica gel column chromatography eluting with 0.5% methanol in dichloromethane. This provided 116 mg of compound 119.

methyl 2-hydroxy-5-[({7-[(2-{[7-({[4-hydroxy-3-(methoxycarbonyl)phenyl]amino}sulfonyl)(2-naphthyl)]amino}ethyl)amino](2-naphthyl) }sulfonyl)amino]benzoate (Compound 120)

To 99 mg (0.08 mmol) of compound 119 was added 9 mL of a 5% (v/v) solution of piperidine in THF. The suspension was allowed to stir at ambient temperature for 24 hours. The reaction was partitioned between ethyl acetate and 1N HCl. The organic layer was dried (MgSO$_4$), filtered, and the volatiles removed by rotary evaporation. The product was purified by silica gel column chromatography eluting with 1% methanol in dichloromethane and then 2% methanol in dichloromethane. This provided 64 mg of compound 120.

5-({[7-({2-[(7-{[(3-carboxy-4-hydroxyphenyl) amino]sulfonyl}(2-naphthyl))amino]-ethyl}amino) (2-naphthyl)]sulfonyl}amino)-2-hydroxybenzoic acid (Compound 121)

To 64 mg (0.08 mmol) of compound 120 was added 20 mL of saturated sodium carbonate, 76 mg of sodium hydrosulfite (Na$_2$S$_2$O$_4$), and 2 mL of DMF. The reaction was allowed to stir at ambient temperature for 22 hours. Then, the reaction was extracted with ethyl acetate and 1 N HCl. The organic layer was dried (MgSO$_4$), filtered, and the volatiles removed by rotary evaporation. The product was purified by reverse-phase BPLC (C18, 250×20 mm column) using trifluoroacetic acid (TFA) buffer system (Buffer A: 5% acetonitrile, 95% water, 0.05% TFA; Buffer B: 95% acetonitrile, 5% water, 0.05% TFA; 17 mL/min; 0–50% B in 10 min., 50% B for 17 min., 50–100% B in 20 min). Fractions containing the product were combined and lyophilized to provide 24 mg of compound 121.

5-[({7-[3-(7-{[(3-carboxy-4-hydroxyphenyl)amino] sulfonyl}(2-naphthyl))-2-oxoimidzoidinyl]-(2-naphthyl)}sulfonyl)amino]-2-hydroxybenzoic acid (Compound 122)

To 8 mg (0.011 mmol) of compound 121 in 2 mL of saturated sodium carbonate and 2 mL of water was added 3 mg (0.010 mmol) of triphosgene dissolved in 0.5 mL of THF, dropwise. The addition was made over a period of 15 min. The reaction was judged incomplete by HPLC, so another 4.5 mg (0.015 mmol) of triphosgene in 0.5 mL of THF was added as before. After 2 hours, the reaction was acidified with 6N HCl and a precipitate formed. The suspension was frozen and lyophilized. The resulting solid was dissolved in dimethyl sulfoxide/water/acetonitrile and purified by reverse-phase HPLC (C18, 250×20 mm column) using trifluoroacetic acid (TFA) buffer system (Buffer A: 5% acetonitrile, 95% water, 0.05% TFA; Buffer B: 95% acetonitrile, 5% water, 0.05% TFA; 19 mL/min; 0–100% B in 20 min). This provided 1 mg of the desired compound 122.

Compound 123 was prepared by a similar synthetic sequence as outlined in Reaction Scheme VI.

TABLE 6

[Structure diagram showing a symmetric molecule with two naphthalene-sulfonamide-benzoic acid groups connected through an imidazolidinone linker]

| Compound | R |
|----------|-----|
| 122 | OH |
| 123 | Cl |

Example 7

Compound 129 was prepared according to the procedure outlined in Reaction Scheme VII. Compound 126 was prepared from commercially available 3-sulfobenzoic acid using standard procedures known to those skilled in the art.

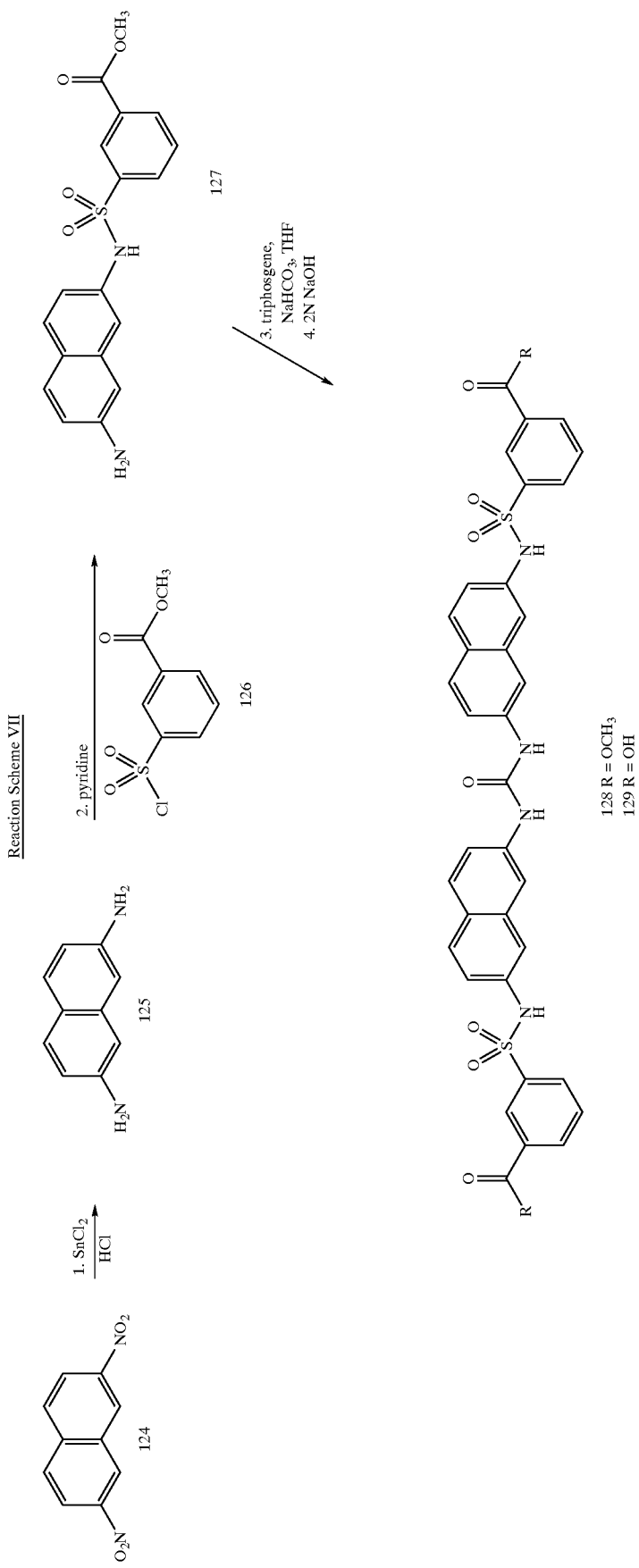

naphthalene-2,7-diamine (Compound 125)

To 1.39 g (6.37 mmol) of 2,7-dinitronaphthalene (124) was added 25 mL of concentrated HCA and 15 mL of ethanol. Then, 9.6 g (50.9 mmol) of tin (II) chloride was added and the reaction was heated at 78 C for 24 hours. The reaction was made basic with NaOH and extracted with ethyl acetate. The ethyl acetate layer was dried (MgSO$_4$), filtered, and the volatiles removed by rotary evaporation. The product was purified by silica gel column chromatography eluting with 1% methanol in dichloromethane. This provided 0.965 g of compound 125.

methyl 3-{[(7-amino-2-naphthyl)amino]sulfonyl}benzoate (Compound 127)

To 277 mg (1.19 mmol) of compound 125 was added 30 mL of THF. Then, 900 μL of pyridine and 10 mL of sulfolane was added to this suspension. A solution of 307 mg (1.31 mmol) of compound 126 in 10 mL of THF was added dropwise. The reaction was allowed to stir at ambient temperature for 14 hours. The reaction was extracted with ethyl acetate (2×) and 1N HCl. The ethyl acetate layers were discarded. The aqueous layer was made basic with NaOH and then extracted with ethyl acetate. The ethyl acetate layer was then extracted with water at pH 2.6 until no more starting material (compound 125) was detected in the organic layer. The ethyl acetate layer was then dried (MgSO$_4$), filtered, and the volatiles removed by rotary evaporation. The resulting residue was dissolved in ethyl acetate and treated with 1N HCl in diethyl ether. The resulting solid was collected to yield 48 mg of compound 127 as the hydrochloride salt.

methyl 3-({[7-({[7-({[3-(methoxycarbonyl)phenyl]sulfonyl}amino)-2-naphthyl]amino}carbonylamino)-2-naphthyl]amino}sulfonyl)benzoate (compound 128) and 3-{[(7-{[(7-{[(3-carboxyphenyl)sulfonyl]amino}-2-naphthyl)amino]carbonylamino}-2-naphthyl)amino]sulfonyl}benzoic acid (Compound 129)

To 43 mg (0.11 mmol) of compound 127 was added 8 mL of 1 M sodium bicarbonate and 0.5 mL of THF to give a clear solution. Then, a solution of 33 mg (0.11 mmol) of triphosgene in 0.5 mL of THF was added dropwise. HPLC analysis showed the reaction was incomplete so another 33 mg of triphosgene was added dropwise. After HPLC analysis showed the reaction to still be incomplete, a third batch of triphosgene was added. The reaction was judged complete so the volatiles were removed by rotary evaporation and the resulting residue (compound 128) was treated with 2N NaOH. The reaction was allowed to stir at ambient temperature for 14 hours. Then, the solution was adjusted to pH 1 with 6 N HCl, and a precipitate formed. The solid was collected by vacuum filtration and purified by silica gel column chromatography to provide 16 mg of compound 129.

Example 8

The unsymmetrical compounds 136–145 were prepared according to the general procedures outlined in Reaction Scheme VIII for the synthesis of compounds 136 and 137. The various amines used in place of compound 18 were prepared by the general procedure for compound 18 that is outlined in Reaction Scheme II.

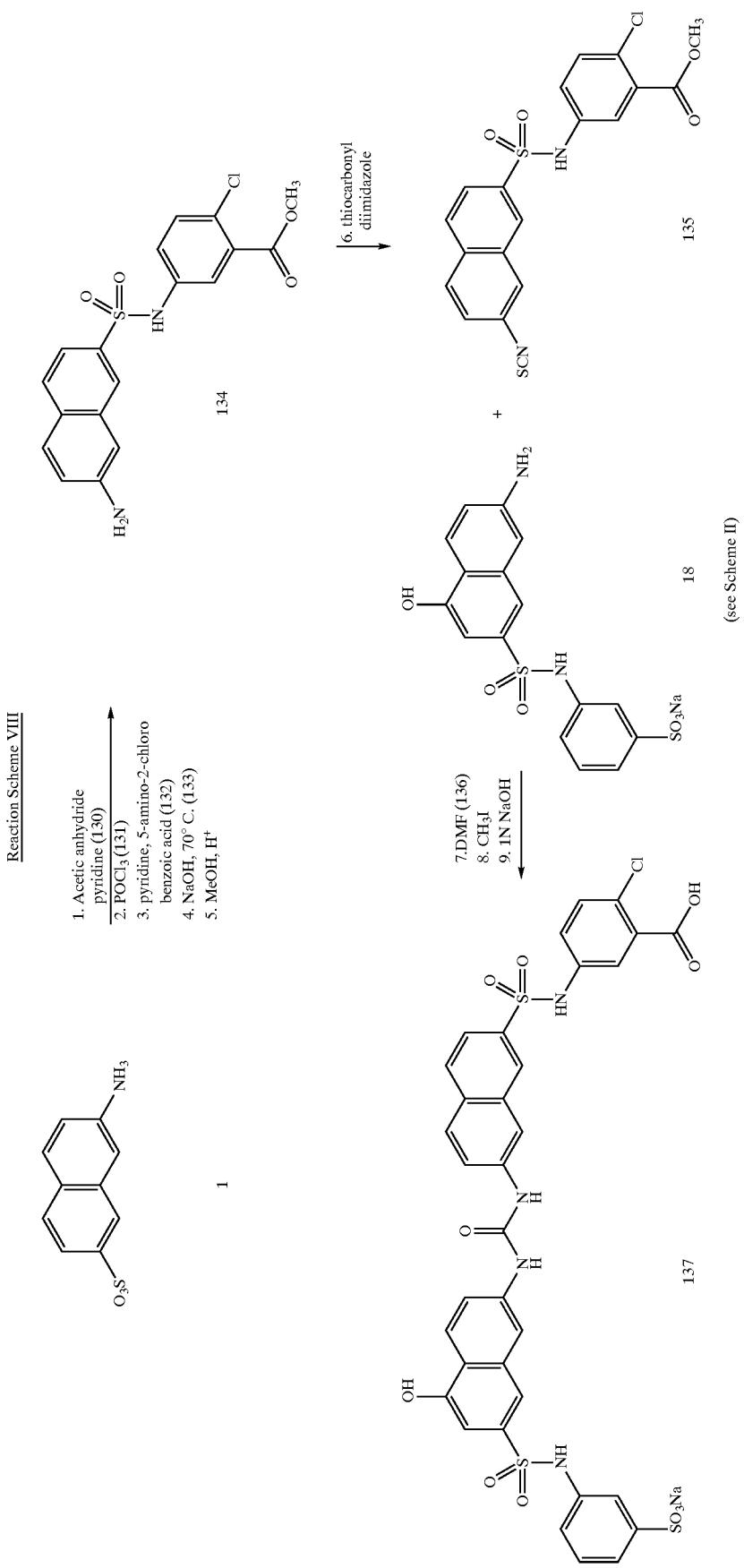

7-(acetylamino)naphthalene-2-sulfonic acid sodium salt (Compound 130)

To 3.75 g (16.8 mmol) of 7-amino-naphthalene-2-sulfonic acid (compound 1) was added 20 mL each of pyridine and acetic anhydride. The reaction was allowed to stir at ambient temperature for 24 hours. The black reaction was cooled in an ice bath and then 45 mL of methanol was added slowly. After 1 hour, a solution of sodium methoxide (425 mg of sodium in 10 mL methanol) was added. A precipitate formed. The suspension was allowed to stir for 2 hours and then the solid was collected by vacuum filtration and was washed with ethyl acetate. This provided 4.4 g of compound 130.

N-[7-(chlorosulfonyl)-2-naphthyl]acetamide (Compound 131)

To 3.6 g (12.5 mmol) of compound 130 was added 100 mL of phosphorous oxychloride. Then, 4 mL of dimethylacetamide was added dropwise. The reaction was allowed to stir at ambient temperature for 5 hours and then was poured onto 2 L of ice. After the ice had melted, the solid precipitate was collected by vacuum filtration and was washed with water. After drying in vacuo, this provided 3.4 g of compound 131.

5-({[7-(acetylamino)(2-naphthyl)]sulfonyl}amino)-2-chlorobenzoic acid (Compound 132)

To 15 g (0.087 mol) of 5-amino-2-chlorobenzoic acid was dissolved in 450 mL of THF and 15 mL of pyridine. The solution was cooled to 5° C. in an ice-water bath. Then, a solution of 20.8 g (0.074 mol) of compound 131 dissolved in 200 mL of THF was added over a 10 min period. The reaction was kept at 5° C. for 30 min, and then allowed to warm to room temperature. The reaction was allowed to stir for an additional 4 hours. Then, the reaction was filtered to remove some insoluble material and the resulting clear filtrate was reduced to a solid by the removal of the volatiles by rotary evaporation. This solid was extracted with ethyl acetate and 1 N HCl. The ethyl acetate layer was further extracted with 0.5 M NaOH (once) and 0.33 M NaOH (three times). The aqueous layers were combined, acidified with HCl, and back extracted into ethyl acetate. After drying (MgSO$_4$), filtration, and removal of the ethyl acetate by rotary evaporation, the solid residue was dissolved in 2.8 L of 50/50 methanol/water with heating. The solution was allowed to cool to room temperature and a small amount of solid was removed by vacuum filtration and discarded. The clear filtrate was allowed to sit for 48 hours and then was reduced in volume to about 500 mL by rotary evaporation. The solid was collected by vacuum filtration. After drying in vacuo, this provided 17.6 g of compound 132.

5-{[(7-amino(2-naphthyl))sulfonyl]amino}-2-chlorobenzoic acid (Compound 133)

To 13.5 g (0.032 mol) of compound 132 was added 100 mL of 5N NaOH. This solution was heated at 50° C. for 8 hours. Then, the reaction was acidified with 86 mL of 6N HCl and extracted with ethyl acetate. The ethyl acetate was washed with 1N HCl, water, and brine. The organic layer was dried (MgSO$_4$), filtered, and the volatiles removed by rotary evaporation to yield 11.3 g of compound 133.

methyl 5-{[(7-amino(2-naphthyl))sulfonyl]amino}-2-chlorobenzoate (Compound 134)

To 10.1 g (0.027 mol) of compound 133 dissolved in 250 mL of methanol was added 50 mL of 4 N HCl in dioxane. This solution was allowed to stir at ambient temperature for 18 hours. The reaction was incomplete, so it was heated at reflux for an additional 5 hours. Then, the volatiles were removed by rotary evaporation and the resulting solid was extracted with ethyl acetate and 0.4 N sodium bicarbonate, water, and brine. The organic layer was dried (MgSO$_4$), filtered, and the volatiles removed by rotary evaporation to yield 8.71 g of compound 134.

methyl 2-chloro-5-{[(7-isothiocyanato(2-naphthyl))sulfonyl]amino}benzoate (Compound 135)

To 4.5 g (11.5 mmol) of compound 134 and 9.01 g (50.6 mmol) of 1,1'-thiocarbonyldiimidazole was added 50 mL of TBF. The solution was allowed to stir at ambient temperature for 1.5 hours. Then, the reaction was poured into 300 mL of ethyl acetate and extracted with 1N HCl, water, and brine. The organic layer was dried (MgSO$_4$), filtered, and the volatiles removed by rotary evaporation to yield 4.77 g of compound 135.

3-[({7-[({[7-({[4-chloro-3-(methoxycarbonyl)phenyl]amino}sulfonyl) (2-naphthyl)]amino)-}-thioxomethyl)amino]-4-hydroxy-2-naphthyl}sulfonyl)amino]benzenesutfonic acid (Compound 136)

To 170 mg (0.39 mmol) of compound 135 dissolved in 5 mL of DMF was added a solution of 100 mg (0.25 mmol) of compound 18 in 5 mL of DMF. The reaction was allowed to stir at ambient temperature. After 4 days, the DMF was removed by rotary evaporation and kept under high vacuum to remove traces of DMF. Then, the resulting residue was treated with dichloromethane (50 mL) and sonicated to form a suspension. The solid, insoluble product was collected by vacuum filtration. This solid was dissolved in methanol and then the methanol was removed by rotary evaporation. The resulting solid was again treated with dichloromethane, sonicated, and collected by vacuum filtration. This provided 172 mg of an orange solid.

2-chloro-5-{[(7-{[(5-hydroxy-7-{[(3-sulfophenyl)amino]sulfonyl}(2-naphthyl))amino]-carbonylamino}(2-naphthyl))sulfonyl]amino}benzoic acid (Compound 137)

To 100 mg (0.12 mmol) of compound 136 was added 15 mL of acetonitrile followed by 10 mL of THF and 1 mL of iodomethane. The reaction was allowed to stir at ambient temperature for 4 days. HPLC analysis indicated that the reaction was complete. The volatiles were removed by rotary evaporation and the residue was dissolved in 1N NaOH (aqueous) at 0–50 C. The reaction was kept in an ice bath for 30 minutes, and then allowed to warm to room temperature over 2 hours. The reaction solution was filtered through a 0.2 um nylon filter to remove some cloudiness. Then the reaction pH was adjusted to about 1 with 6N HCl. The resulting solid precipitate was collected by vacuum filtration. This provided 60 mg of compound 137.

The compounds 138–145 (Table 7) were prepared by the same general procedures as described above for the synthesis of compounds 136 and 137 except that different amines were used in place of compound 18. The amines were prepared by the same general procedure as for the synthesis compound 18, as depicted in Reaction Scheme II. Compounds in Table 7 with are shown in the free acid form.

TABLE 7

| Compound # | R⁰ | R⁵ | R⁶ | R⁰⁰ | K |
|---|---|---|---|---|---|
| 136 | 3-sulfo-phenylamino (SO₂OH) | OH | H | 4-chloro-3-(methoxysulfinyl)phenylamino | S |
| 137 | 3-sulfo-phenylamino (SO₂OH) | OH | H | 4-chloro-3-(hydroxysulfinyl)phenylamino | S |
| 138 | 3-sulfo-phenylamino (SO₂OH) | OH | H | 4-chloro-3-(hydroxysulfinyl)phenylamino | O |
| 139 | 4-(methoxycarbonyl)phenylamino | H | H | 4-chloro-3-(methoxysulfinyl)phenylamino | S |
| 140 | 4-carboxyphenylamino | H | H | 4-chloro-3-(hydroxysulfinyl)phenylamino | S |
| 141 | 4-carboxyphenylamino | H | H | 4-chloro-3-(hydroxysulfinyl)phenylamino | O |
| 142 | 3-(methoxycarbonyl)phenylamino | H | H | 4-chloro-3-(methoxysulfinyl)phenylamino | S |
| 143 | 3-carboxyphenylamino | H | H | 4-chloro-3-(methoxysulfinyl)phenylamino | S |

TABLE 7-continued

| Compound # | R⁰ | R⁵ | R⁶ | R⁰⁰ | K |
|---|---|---|---|---|---|
| 144 | 3-carboxyphenylamino | H | H | 3-sulfo-4-chlorophenylamino | O |
| 145 | 3-sulfamoylphenylamino | H | H | 3-(methoxysulfonyl)-4-chlorophenylamino | S |
| 146 | 3-sulfamoylphenylamino | H | H | 3-sulfo-4-chlorophenylamino | S |
| 147 | 3-sulfamoylphenylamino | H | H | 3-sulfo-4-chlorophenylamino | O |
| 148 | 3-sulfamoylphenylamino | OH | H | 3-(methoxysulfonyl)-4-chlorophenylamino | O |
| 149 | 3-sulfamoylphenylamino | OH | H | 3-sulfo-4-chlorophenylamino | S |
| 150 | 3-sulfamoylphenylamino | OH | H | 3-sulfo-4-chlorophenylamino | O |

TABLE 7-continued
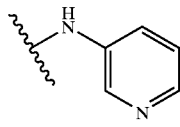
| Compound # | R⁰ | R⁵ | R⁶ | R⁰⁰ | K |
|---|---|---|---|---|---|
| 151 | 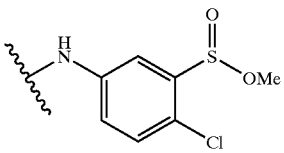 | H | H | 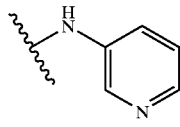 | O |
| 152 | 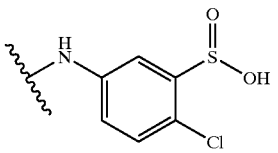 | H | H | 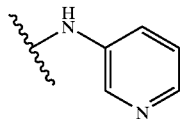 | O |
| 153 | 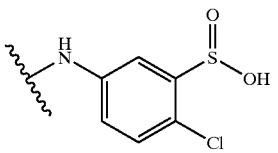 | H | H | 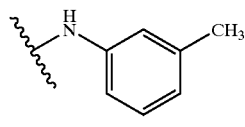 | O |
| 154 | 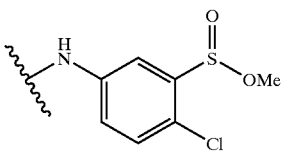 | H | H | 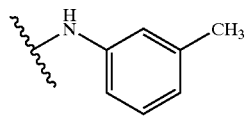 | S |
| 155 | 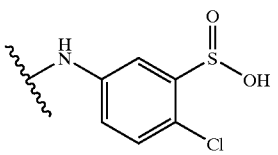 | H | H | 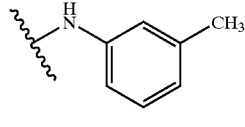 | S |
| 156 | 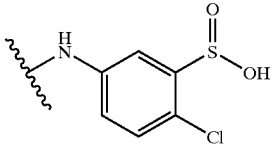 | H | H | | O |
Example 9
The compounds 157–168 were prepared according to the procedures outlined in Reaction Scheme IX.

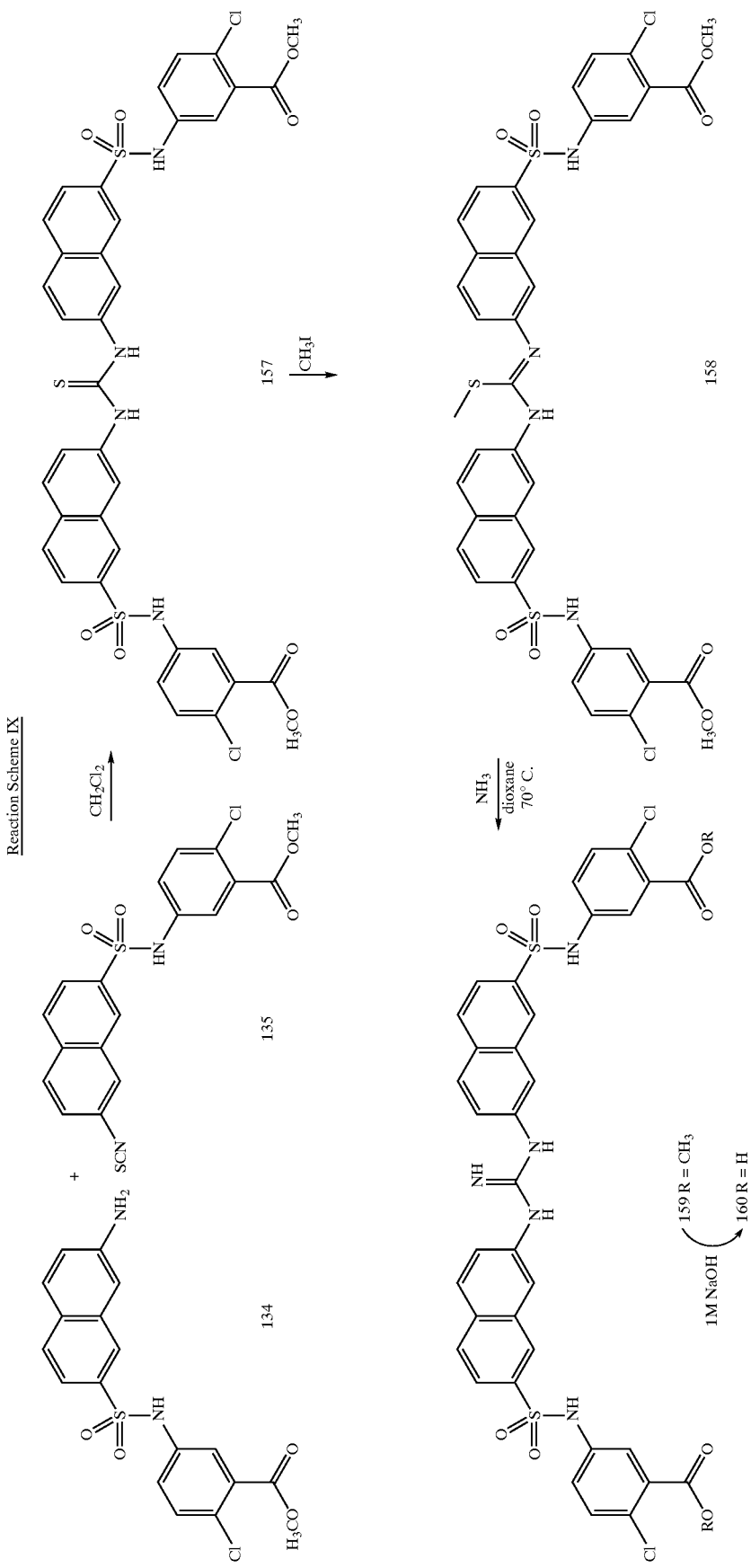
Reaction Scheme IX methyl 2-chloro-5-[({7-[({7-({[4chloro-3-(methoxycarbonyl)phenyl]amino}sulfonyl)(2-naphthyl)]amino}thioxomethyl)amino](2-naphthyl)}sulfonyl)amino]benzoate (Compound 157)

To 3.0 g (7.68 mmol) of compound 134 was added a solution of 4.0 g (9.24 mmol) of compound 135 in 200 mL of dichloromethane. The reaction was allowed to stir at ambient temperature for 48 hours. The fine, white solid was collected to give 5.2 g of compound 157.

methyl 5-({[7-(1-aza-2-{[7-({[4-chloro-3-(methoxycarbonyl)phenyl]amino}sulfonyl)(2-naphthyl)]amino)-2-methylthiovinyl)(2-naphthyl)]sulfonyl}amino)-2-chlorobenzoate (Compound 158)

To 1.0 g (1.21 mmol) of compound 157 dissolved in 50 mL of acetonitrile was added 1.1 mL of methyl iodide (17.7 mmol). The reaction was allowed to stir under an argon atmosphere for 72 hours. The volatiles were removed by rotary evaporation, and the resulting yellow solid was extracted using ethyl acetate and 1M sodium carbonate. The organic layer was washed with 50/50 brine/water followed by brine. The organic layer was separated and volatiles removed by rotary evaporation to yield 0.95 g of compound 158.

methyl 5-({[7-(2-amino-1-aza-2-{[7-({[4-chloro-3-(methoxycarbonyl)phenyl]amino}sulfonyl)(2-naphthyl)]amino}vinyl)(2-naphthyl)]sulfonyl}amino)-2-chlorobenzoate (Compound 159)

To 220 mg (0.24 mmol) of compound 158 was added 10 mL of a 0.5 M NH$_3$ solution in dioxane. The resulting solution was placed in a sealed tube and heated at 70° C. for 18 hours, followed by 24 hours at 80° C. Then, additional NH$_3$ gas was bubbled into the reaction for 4 min. The reaction was sealed and heating at 80° C. continued for an additional 51 hours. Then, the reaction temperature was lowered to 65° C. and continued for 11 days. At this point, the reaction had reached 70% completion based upon HPLC analysis. The reaction was stopped by removal of the volatiles by rotary evaporation. The product was purified by silica gel column chromatography eluting with 3% methanol in dichloromethane followed by 5% methanol in dichloromethane. Finally, the product was eluted with 90:2:1 ethyl acetate:isopropanol:water. This provided 117 mg of compound 159.

5-{[(7-{2-amino-1-aza-2-[(7-{[(3-carboxy-4-chlorophenyl)amino]sulfonyl}(2-naphthyl)amino]vinyl}(2-naphthyl))sulfonyl]amino}-2-chlorobenzoic acid (Compound 160)

To 50 mg (0.062 mmol) of compound 159 was added 10 mL of 1N NaOH. The resulting solution was allowed to stir at ambient temperature for 1 hour. The reaction was acidified to pH 1 using 11 mL of 1N HCl. A white precipitate formed, which was collected by vacuum filtration and was washed with water. The solid was dried in vacuo to provide 45 mg of compound 160.

The compounds 161–168 (Table 8) were prepared by the same. general procedures as described above for the synthesis of compounds 157–160 except that other amines were used in place of ammonia. Compounds in Table 8 with acidic groups are shown in the free acid form.

TABLE 8

| Compound # | K | R |
|---|---|---|
| 157 | S | OCH$_3$ |
| 158 | SCH$_3$ | OCH$_3$ |
| 159 | NH | OCH$_3$ |
| 160 | NH | OH |
| 161 | NCH$_3$ | OCH$_3$ |
| 162 | NCH$_3$ | OH |
| 163 | N(CH$_3$)$_2$ | OCH$_3$ |
| 164 | N(CH$_3$)$_2$ | OH |
| 165 | NCN | OCH$_3$ |
| 166 | NCN | OH |
| 167 | NHCH$_2$CH=CH$_2$ | OCH$_3$ |
| 168 | NHCH$_2$CH=CH$_2$ | OH |

Example 10

The compounds 169–181 (Table 9) were prepared according to the same general procedures outlined in Reaction Schemes I and II and described for compounds in Table 1. The compound 6-naphthalene-2-sulfonic acid was used in place of compounds 1 and 2.

TABLE 9

| Compound # | R$^0$ | R$^{00}$ |
|---|---|---|
| 169 | | |

TABLE 9-continued

| Compound # | R⁰ | R⁰⁰ |
|---|---|---|
| 170 | —NH—C₆H₄—C(O)OCH₃ (3-substituted) | —NH—C₆H₄—C(O)OCH₃ (3-substituted) |
| 171 | —NH—C₆H₄—C(O)OH (3-substituted) | —NH—C₆H₄—C(O)OH (3-substituted) |
| 172 | —NH—C₆H₄—C(O)OMe (4-substituted) | —NH—C₆H₄—C(O)OMe (4-substituted) |
| 173 | —NH—C₆H₄—C(O)OH (4-substituted) | —NH—C₆H₄—C(O)OH (4-substituted) |
| 174 | —NH—C₆H₃(CO₂Me)₂ (3,5-disubstituted) | —NH—C₆H₃(CO₂Me)₂ (3,5-disubstituted) |
| 175 | —NH—C₆H₃(CO₂H)₂ (3,5-disubstituted) | —NH—C₆H₃(CO₂H)₂ (3,5-disubstituted) |
| 176 | —NH—C₆F₃(CO₂Me) trifluoro substituted | —NH—C₆F₃(CO₂Me) trifluoro substituted |
| 177 | —NH—C₆F₃(CO₂H) trifluoro substituted | —NH—C₆F₃(CO₂H) trifluoro substituted |

TABLE 9-continued

| Compound # | R⁰ | R⁰⁰ |
|---|---|---|
| 178 | 4-(ethoxycarbonylmethyl)phenylamino | 4-(ethoxycarbonylmethyl)phenylamino |
| 179 | 4-(carboxymethyl)phenylamino | 4-(carboxymethyl)phenylamino |
| 180 | 4-(ethoxycarbonyl)phenylamino | 4-(ethoxycarbonyl)phenylamino |
| 181 | 3-carboxypyridin-1-yl | 3-carboxypyridin-1-yl |

Example 11

The [$^{14}$C] labeled compound 15 was prepared according to the procedure outlined in Reaction Scheme X.

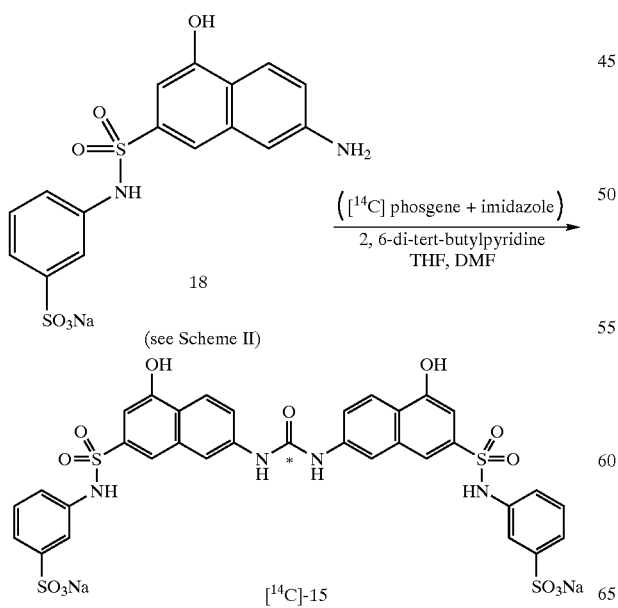

Reaction Scheme X

[$^{14}$C]-3-{[(4-hydroxy-7-{[(5-hydroxy-7-{[(3-sulfophenyl)amino]sulfonyl}(2-naphthyl))amino]-carbonylamino}-2-naphthyl)sulfonyl]amino}benzenesulfonic acid (Compound [$^{14}$C]-15)

To 51 mg (0.013 mmol) of compound 18 dissolved in 1.7 mL of DMF was added 58 μL (0.026 mmol) of 2,6-di-tert-butylpyridine. Then, in a separate test tube with 13.6 mg (0.020 mmol) of imidazole in 1.7 mL of THF, was added 36 μL (0.007 mmol) of [$^{14}$C]-phosgene (20% in toluene). This formed a white solid. After 2 min., 1.7 mL of DMF was added to the THF suspension to form a clear solution. This solution was added to the DMF solution of compound 18. After 4 hours, the product was purified by reverse-phase HPLC (C18, 250×20 mm column) using trifluoroacetic acid (TFA) buffer system (Buffer A: 5% acetonitrile, 95% water, 0.1% TFA; Buffer B: 95% acetonitrile, 5% water, 0.1% TFA) to give 16 mg of compound [$^{14}$C]-15 with an activity of 55 mCi/mmol. names of the compounds prepared according to the general procedures described and whose structures are indicated in Tables 1–9 are listed in Table 10. Compounds that have acidic functionalities are named as the parent free acid. The following IUPAC names were derived using the software program Chemistry 4D Draw™ from ChemInnovation Software, Inc.

TABLE 10

| Compound # | IUPAC Name |
|---|---|
| 3 | 7-{[(7-sulfo-2-naphthyl)amino]carbonylamino}naphthalene-2-sulfonic acid |
| 4 | 4-hydroxy-7-{[(5-hydroxy-7-sulfo(2-naphthyl))amino]carbonylamino}naphthalene-2-sulfonic acid |
| 8 | 7-[({7-[({3-[(4-methylphenyl)oxysulfonyl]phenyl}amino)sulfonyl]-2-naphthyl}amino)carbonylamino]naphthalene-2-sulfonic acid |
| 9 | 4-methylphenyl 3-[({7-[(N-{7-[({3-[(4-methylphenyl)oxysulfonyl]phenyl}amino)sulfonyl]-2-naphthyl}carbamoyl)amino]-2-naphthyl}sulfonyl)amino]benzenesulfonate |
| 10 | 4-hydroxy-7-[({5-hydroxy-7-[({3-[(4-methylphenyl)oxysulfonyl]phenyl}amino)sulfonyl](2-naphthyl)}amino)carbonylamino]naphthalene-2-sulfonic acid |
| 11 | 4-methylphenyl 3-[({4-hydroxy-7-[(N-{5-hydroxy-7-[({3-[(4-methylphenyl)oxysulfonyl]phenyl}amino)sulfonyl](2-naphthyl)}carbamoyl)amino]-2-naphthyl}sulfonyl)amino]benzenesulfonate |
| 12 | 7-{[(7-{[(3-sulfophenyl)amino]sulfonyl}-2-naphthyl)amino]carbonylamino}naphthalene-2-sulfonic acid |
| 13 | 3-{[(7-{[N-(7-{[(3-sulfophenyl)amino]sulfonyl}-2-naphthyl)carbamoyl]amino}-2-naphthyl)sulfonyl]amino}benzenesulfonic acid |
| 14 | 4-hydroxy-7-{[(5-hydroxy-7-{[(3-sulfophenyl)amino]sulfonyl}(2-naphthyl))amino]carbonylamino}naphthalene-2-sulfonic acid |
| 15 | 3-{[(4-hydroxy-7-{[N-(5-hydroxy-7-{[(3-sulfophenyl)amino]sulfonyl}(2-naphthyl))carbamoyl]amino}-2-naphthyl)sulfonyl]amino}benzenesulfonic acid |
| 16 | 3-bromo-7-{[(6-bromo-5-hydroxy-7-sulfo(2-naphthyl))amino]carbonylamino}-4-hydroxynaphthalene-2-sulfonic acid |
| 19 | 7-[({7-[({3-[(4-methylphenyl)oxysulfonyl]phenyl}amino)sulfonyl]-2-naphthyl}amino)carbonylamino]naphthalene-2-sulfonic acid |
| 20 | 7-{[(7-{[(4-sulfophenyl)amino]sulfonyl}-2-naphthyl)amino]carbonylamino}naphthalene-2-sulfonic acid |
| 21 | 4-methylphenyl 4-[({7-[(N-{7-[({4-[(4-methylphenyl)oxysulfonyl]phenyl}amino)sulfonyl]-2-naphthyl}carbamoyl)amino]-2-naphthyl}sulfonyl)amino]benzenesulfonate |
| 22 | 4-{[(7-{[N-(7-{[(4-sulfophenyl)amino]sulfonyl}-2-naphthyl)carbamoyl]amino}-2-naphthyl)sulfonyl]amino}benzenesulfonic acid |
| 23 | N-(7-{[(3-sulfamoylphenyl)amino]sulfonyl}(2-naphthyl))[(7-{[(3-sulfamoylphenyl)amino]sulfonyl}(2-naphthyl))amino]carboxamide |
| 24 | methyl 4-({[7-({[7-({[4-methoxycarbonyl)phenyl]amino}sulfonyl-2-naphthyl]amino}carbonylamino)-2-naphthyl]sulfonyl}amino)benzoate |
| 25 | 4-{[(7-{[N-(7-{[(4-carboxyphenyl)amino]sulfonyl}-2-naphthyl)carbamoyl]amino}-2-naphthyl)sulfonyl]amino}benzoic acid |
| 26 | 4-hydroxy-7-({[5-hydroxy-7-({[4-(methoxycarbonyl)phenyl]amino}sulfonyl)(2-naphthyl)]amino}carbonylamino)naphthalene-2-sulfonic acid |
| 27 | methyl 4-({[4-hydroxy-7-({[5-hydroxy-7-({[4-(methoxycarbonyl)phenyl]amino}sulfonyl)(2-naphthyl)]amino}carbonylamino)-2-naphthyl]sulfonyl}amino)benzoate |
| 28 | 4-{[(4-hydroxy-7-{[N-(5-hydroxy-7-sulfo(2-naphthyl))carbamoyl]amino}-2-naphthyl)sulfonyl]amino}benzoic acid |
| 29 | 4-{[(7-{[N-(7-{[(4-carboxyphenyl)amino]sulfonyl}-5-hydroxy(2-naphthyl))carbamoyl]amino}4-hydroxy-2-naphthyl)sulfonyl]amino}benzoic acid |
| 30 | 2-hydroxy-3-{[(7-{[N-(7-sulfo(2-naphthyl)}carbamoyl]amino}(2-naphthyl))sulfonyl]amino}benzoic acid |
| 31 | 3-{[(7-{[N-(7-{[(3-carboxy-2-hydroxyphenyl)amino]sulfonyl}(2-naphthyl))carbamoyl]amino}(2-naphthyl))sulfonyl]amino}-2-hydroxybenzoic acid |
| 32 | 2-hydroxy-5-{[(7-{[N-(7-sulfo(2-naphthyl))carbamoyl]amino}(2-naphthyl))sulfonyl]amino}benzoic acid |
| 33 | 5-{[(7-{[N-(7-{[(3-carboxy-4-hydroxyphenyl)amino]sulfonyl}(2-naphthyl))carbamoyl]amino}(2-naphthyl))sulfonyl]amino}-2-hydroxybenzoic acid |
| 34 | 2-hydroxy-4-{[(7-{[N-(7-sulfo(2-naphthyl))carbamoyl]amino}(2-naphthyl))sulfonyl]amino}benzoic acid |
| 35 | 4-{[(7-{[N-(7-{[(4-carboxy-3-hydroxyphenyl)amino]sulfonyl}(2-naphthyl))carbamoyl]amino}(2-naphthyl))sulfonyl]amino}-2-hydroxybenzoic acid |
| 36 | 7-({[7-({[3-(methoxycarbonyl)-4-nitrophenyl]amino}sulfonyl)-2-naphthyl]amino}carbonylamino)naphthalene-2-sulfonic acid |
| 37 | 2-nitro-5-{[(7-{[N-(7-sulfo(2-naphthyl))carbamoyl]amino}(2-naphthyl))sulfonyl]amino}benzoic acid |
| 38 | 5-{[(7-{[N-(7-{[(3-carboxy-4-nitrophenyl)amino]sulfonyl}(2-naphthyl))carbamoyl]amino}(2-naphthyl))sulfonyl]amino}-2-nitrobenzoic acid |
| 39 | methyl 3-({[7-({[7-({[3-(methoxycarbonyl)phenyl]amino}sulfonyl)-2-naphthyl]amino}carbonylamino)-2-naphthyl]sulfonyl}amino)benzoate |
| 40 | 3-{[(7-{[N-(7-{[(3-carboxyphenyl)amino]sulfonyl}-2-naphthyl)carbamoyl]amino}-2-naphthyl)sulfonyl]amino}benzoic acid |
| 41 | methyl 3-({[4-hydroxy-7-({[5-hydroxy-7-({[3-(methoxycarbonyl)phenyl]amino}sulfonyl)(2-naphthyl)]amino}carbonylamino)-2-naphthyl]sulfonyl}amino)benzoate |
| 42 | 3-{[(7-{[N-(7-{[(3-carboxyphenyl)amino]sulfonyl}-5-hydroxy(2-naphthyl))carbamoyl]amino}4-hydroxy-2-naphthyl)sulfonyl]amino}benzoic acid |
| 43 | 5-{[(7-{[N-(7-{[(3-carboxy-4-hydroxyphenyl)amino]sulfonyl}-5-hydroxy(2-naphthyl))carbamoyl]amino}-4-hydroxy(2-naphthyl))sulfonyl]amino}-2-hydroxybenzoic acid |
| 44 | methyl 2-({[7-({[7-({[2-(methoxycarbonyl)phenyl]amino}sulfonyl)-2-naphthyl]amino}carbonylamino)-2-naphthyl]sulfonyl}amino)benzoate |
| 45 | 2-{[(7-{[N-(7-{[(2-carboxyphenyl)amino]sulfonyl}-2-naphthyl)carbamoyl]amino}-2-naphthyl)sulfonyl]amino}benzoic acid |

TABLE 10-continued

| Compound # | IUPAC Name |
|---|---|
| 46 | methyl 2-({[4-hydroxy-7-({[5-hydroxy-7-({[2-(methoxycarbonyl)phenyl]amino}sulfonyl)(2-naphthyl)]amino}carbonylamino)-2-naphthyl]sulfonyl}amino)benzoate |
| 47 | 2-{[(7-{[N-(7-{[(2-carboxyphenyl)amino]sulfonyl}-5-hydroxy(2-naphthyl))carbamoyl]amino}-4-hydroxy-2-naphthyl)sulfonyl]amino}benzoic acid |
| 48 | 5-{[(7-{[N-(7-{[(3-carboxy-4-chlorophenyl)amino]sulfonyl}(2-naphthyl))carbamoyl]amino}(2-naphthyl))sulfonyl]amino}-2-chlorobenzoic acid |
| 49 | 5-{[(7-{[N-(7-{[(3-carboxy-4-chlorophenyl)amino]sulfonyl}-5-hydroxy(2-naphthyl))carbamoyl]amino}-4-hydroxy(2-naphthyl))sulfonyl]amino}-2-chlorobenzoic acid |
| 50 | methyl 3-({[7-({[7-({[3,5-bis(methoxycarbonyl)phenyl]amino}sulfonyl)-5-hydroxy(2-naphthyl)]amino}carbonylamino)-4-hydroxy-(2-naphthyl)]sulfonyl}amino)-5-(methoxycarbonyl)benzoate |
| 51 | 5-{[(7-{[N-(7-{[(3,5-dicarboxyphenyl)amino]sulfonyl}-5-hydroxy(2-naphthyl))carbamoyl]amino}4-hydroxy-2-naphthyl)sulfonyl]amino}benzene-1,3-dicarboxylic acid |
| 52 | 2-[3-({[7-({[7-({[3-(carboxymethyl)phenyl]amino}sulfonyl)-5-hydroxy(2-naphthyl)]amino}carbonylamino)-4-hydroxy-2-naphthyl]sulfonyl}amino)phenyl]acetic acid |
| 53 | methyl 2-hydroxy-5-({[7-({[7-({[4-hydroxy-3-(methoxycarbonyl)phenyl]amino}sulfonyl)(2-naphthyl)]amino}carbonylamino)(2-naphthyl)]sulfonyl}amino)benzoate |
| 54 | methyl 2-chloro-5-({[7-({[7-({[4-chloro-3-(methoxycarbonyl)phenyl]amino}sulfonyl)(2-naphthyl)]amino}carbonylamino)(2-naphthyl)]sulfonyl}amino)benzoate |
| 55 | methyl 2-bromo-5-({[7-({[7-({[4-bromo-3-(methoxycarbonyl)phenyl]amino}sulfonyl)(2-naphthyl)]amino}carbonylamino)(2-naphthyl)]sulfonyl}amino)benzoate |
| 56 | 2-bromo-5-{[(7-{[N-(7-{[(4-bromo-3-carboxyphenyl)amino]sulfonyl}(2-naphthyl))carbamoyl]amino}(2-naphthyl))sulfonyl]amino}benzoic acid |
| 57 | 5-{[(7-{[N-(7-{[(3-carboxy-4-methylphenyl)amino]sulfonyl}(2-naphthyl))carbamoyl]amino}(2-naphthyl))sulfonyl]amino}-2-methylbenzoic acid |
| 58 | 5-{[(7-{[N-(7-{[(3-carboxy-4-fluorophenyl)amino]sulfonyl}(2-naphthyl))carbamoyl]amino}(2-naphthyl))sulfonyl]amino}-2-fluorobenzoic acid |
| 59 | 3-{[(7-{[N-(7-{[(3-carboxy-2-chlorophenyl)amino]sulfonyl}-5-hydroxy(2-naphthyl))carbamoyl]amino}-4-hydroxy(2-naphthyl))sulfonyl]amino}-2-chlorobenzoic acid |
| 60 | 3-{[(7-{[N-(7-{[(3-carboxy-6-chlorophenyl)amino]sulfonyl}-5-hydroxy(2-naphthyl))carbamoyl]amino}-4-hydroxy(2-naphthyl))sulfonyl]amino}-4-chlorobenzoic acid |
| 61 | methyl 2-methoxy-5-({[7-({[7-({[4-methoxy-3-(methoxycarbonyl)phenyl]amino}sulfonyl)(2-naphthyl)]amino}carbonylamino)(2-naphthyl)]sulfonyl}amino)benzoate |
| 62 | 5-{[(7-{[N-(7-{[(3-carboxy-4-methoxyphenyl)amino]sulfonyl}(2-naphthyl))carbamoyl]amino}(2-naphthyl))sulfonyl]amino}-2-methoxybenzoic acid |
| 63 | methyl 4-hydroxy-3-({[7-({[7-({[2-hydroxy-5-(methoxycarbonyl)phenyl]amino}sulfonyl)(2-naphthyl)]amino}carbonylamino)(2-naphthyl)]sulfonyl}amino)benzoate |
| 64 | 3-{[(7-{[N-(7-{[(3-carboxy-6-hydroxyphenyl)amino]sulfonyl}(2-naphthyl))carbamoyl]amino}(2-naphthyl))sulfonyl]amino}4-hydroxybenzoic acid |
| 65 | methyl 4-methoxy-3-({[7-({[7-({[2-methoxy-5-(methoxycarbonyl)phenyl]amino}sulfonyl)(2-naphthyl)]amino}carbonylamino)(2-naphthyl)]sulfonyl}amino)benzoate |
| 66 | 3-{[(7-{[(7-{[(3-carboxy-6-methoxyphenyl)amino]sulfonyl}(2-naphthyl))amino]carbonylamino}(2-naphthyl))sulfonyl]amino}-4-methoxybenzoic acid |
| 67 | N-(7-{[(3-(1H-1,2,3,4-tetraazol-5-yl)phenyl)amino]sulfonyl}(2-naphthyl))[(7-{[(3-(1H-1,2,3,4-tetraazol-5-yl)phenyl)amino]sulfonyl}(2-naphthyl))amino]carboxamide |
| 68 | N-(5-hydroxy-7-{[(3-(1H-1,2,3,4-tetraazol-5-yl)phenyl)amino]sulfonyl}(2-naphthyl))[(5-hydroxy-7-{[(3-(1H-1,2,3,4-tetraazol-5-yl)phenyl)amino]sulfonyl}(2-naphthyl))amino]carboxamide |
| 69 | N-(5-hydroxy-7-{[(4-(1H-1,2,3,4-tetraazol-5-yl)phenyl)amino]sulfonyl}(2-naphthyl))[(5-hydroxy-7-{[(4-(1H-1,2,3,4-tetraazol-5-yl)phenyl)amino]sulfonyl}(2-naphthyl))amino]carboxamide |
| 70 | N-[7-({[3-(diethoxyphosphoryl)phenyl]amino}sulfonyl)(2-naphthyl)]{[7-({[3-(diethoxyphosphoryl)phenyl]amino}sulfonyl)(2-naphthyl)]amino}carboxamide |
| 71 | N-[7-({[3-(ethoxy(hydroxyphosphoryl))phenyl]amino}sulfonyl)(2-naphthyl)]{[7-({[3-(ethoxy(hydroxyphosphoryl))phenyl]amino}sulfonyl)(2-naphthyl)]amino}carboxamide |
| 72 | 7-({[7-({[(1S)-2-(4-hydroxyphenyl)-1-(methoxycarbonyl)ethyl]amino}sulfonyl)-2-naphthyl]amino}carbonylamino)naphthalene-2-sulfonic acid |
| 73 | (2S)-3-(4-hydroxyphenyl)-2-{[(7-{[N-(7-sulfo(2-naphthyl)}carbamoyl]amino}(2-naphthyl))sulfonyl]amino}propanoic acid |
| 74 | methyl (2S)-2-({[7-({N-[7-({[(1S)-2-(4-hydroxyphenyl)-1-(methoxycarbonyl)ethyl]amino}sulfonyl)(2-naphthyl)]carbamoyl}amino)(2-naphthyl)]sulfonyl}amino)-3-(4-hydroxyphenyl)propanoate |
| 75 | (2S)-2-({[7-({N-[7-({[(1S)-1-carboxy-2-(4-hydroxyphenyl)ethyl]amino}sulfonyl)(2-naphthyl)]carbamoyl}amino)(2-naphthyl)]sulfonyl}amino)-3-(4-hydroxyphenyl)propanoic acid |
| 76 | N-{7-[(phenylamino)sulfonyl](2-naphthyl)}({7-[(phenylamino)sulfonyl](2-naphthyl)}amino)carboxamide |
| 77 | N-{7-[(3-pyridylamino)sulfonyl](2-naphthyl)}({7-[(3-pyridylamino)sulfonyl](2-naphthyl)}amino)carboxamide |
| 78 | 7-[({7-[(pyrimidin-2-ylamino)sulfonyl]-2-naphthyl}amino)carbonylamino]naphthalene-2-sulfonic acid |
| 79 | N-{7-[(pyrimidin-2-ylamino)sulfonyl](2-naphthyl)}({7-[(pyrimidin-2-ylamino)sulfonyl](2-naphthyl)}amino)carboxamide |
| 80 | N-{7-[(pyrazin-2-ylamino)sulfonyl](2-naphthyl)}({7-[(pyrazin-2-ylamino)sulfonyl](2-naphthyl))amino)carboxamide |
| 81 | N-(7-{[(3-hydroxyphenyl)amino]sulfonyl}(2-naphthyl))[(7-{[(3-hydroxyphenyl)amino]sulfonyl}(2-naphthyl))amino]carboxamide |

TABLE 10-continued

| Compound # | IUPAC Name |
|---|---|
| 82 | N-[5-hydroxy-7-({[3-(hydroxymethyl)phenyl]amino}sulfonyl)(2-naphthyl)]{[5-hydroxy-7-({[3-(hydroxymethyl)phenyl]amino}sulfonyl)(2-naphthyl)]amino}carboxamide |
| 83 | N-(7-{[(3-cyanophenyl)amino]sulfonyl}(2-naphthyl))[(7-{[(3-cyanophenyl)amino]sulfonyl}(2-naphthyl))amino]carboxamide |
| 84 | N-(7-{[(3-nitrophenyl)amino]sulfonyl}(2-naphthyl))[(7-{[(3-nitrophenyl)amino]sulfonyl}(2-naphthyl))amino]carboxamide |
| 85 | N-[7-({[4-chloro-3-(hydroxymethyl)phenyl]amino}sulfonyl)(2-naphthyl)]{[7-({[4-chloro-3-(hydroxymethyl)phenyl]amino}sulfonyl)(2-naphthyl)]amino}carboxamide |
| 86 | N-(7-{[(3-chloro-4-hydroxyphenyl)amino]sulfonyl}(2-naphthyl))[(7-{[(3-chloro-4-hydroxyphenyl)amino]sulfonyl}(2-naphthyl))amino]carboxamide |
| 87 | N-[7-({[(3,4-dihydroxyphenyl)methyl]amino}sulfonyl)(2-naphthyl)]{[7-({[(3,4-dihydroxyphenyl)methyl]amino}sulfonyl)(2-naphthyl)]amino}carboxamide |
| 88 | N-[5-hydroxy-7-({[3-(trifluoromethyl)phenyl]amino}sulfonyl)(2-naphthyl)]{[5-hydroxy-7-({[3-(trifluoromethyl)phenyl]amino}sulfonyl)(2-naphthyl)]amino}carboxamide |
| 89 | N-(7-sulfanoyl(2-naphthyl))[(7-sulfamoyl(2-naphthyl))amino]carboxamide |
| 90 | 7-{[(7-{[(4-chloro-3-sulfophenyl)amino]sulfonyl}(2-naphthyl)amino]carbonylamino}naphthalene-2-sulfonic acid |
| 91 | 2-chloro-5-{[(7-{[(7-{[(4-chloro-3-sulfophenyl)amino]sulfonyl}(2-naphthyl))amino]carbonylamino}(2-naphthyl))sulfonyl]amino}benzenesulfonic acid |
| 92 | 7-{[(7-{[(4-chloro-3-sulfophenyl)amino]sulfonyl}-5-hydroxy(2-naphthyl))amino]carbonylamino}-4-hydroxynaphthalene-2-sulfonic acid |
| 93 | 2-chloro-5-{[(7-{[(7-{[(4-chloro-3-sulfophenyl)amino]sulfonyl}-5-hydroxy(2-naphthyl))amino]carbonylamino}-4-hydroxy(2-naphthyl))sulfonyl]amino}benzenesulfonic acid |
| 94 | 7-[({5-[(ethoxycarbonyl)methoxy]-7-sulfo(2-naphthyl)}amino)carbonylamino]-4-hydroxynaphthalene-2-sulfonic acid |
| 95 | 4-[(ethoxycarbonyl)methoxy]-7-[({5-[(ethoxycarbonyl)methoxy]-7-sulfo(2-naphthyl)}amino)carbonylamino]naphthalene-2-sulfonic acid |
| 96 | 2-(6-{[N-(5-hydroxy-7-sulfo(2-naphthyl))carbamoyl]amino}-3-sulfonaphthyloxy)acetic acid |
| 97 | 2-[6-({N-[5-(carboxymethoxy)-7-sulfo(2-naphthyl)]carbamoyl}amino)-3-sulfonaphthyloxy]acetic acid |
| 98 | 4-hydroxy-7-{[(5-methoxy-7-sulfo(2-naphthyl))amino]carbonylamino}naphthalene-2-sulfonic acid |
| 99 | 4-methoxy-7-{[(5-methoxy-7-sulfo(2-naphthyl))amino]carbonylamino}naphthalene-2-sulfonic acid |
| 100 | 4-[(2-sulfophenyl)methoxy]-7-[({7-sulfo-5-[(2-sulfophenyl)methoxy](2-naphthyl)}amino)carbonylamino]naphthalene-2-sulfonic acid |
| 101 | 4-(3-sulfopropoxy)-7-({[7-sulfo-5-(3-sulfopropoxy)(2-naphthyl)]amino}carbonylamino)naphthalene-2-sulfonic acid |
| 102 | 4-hydroxy-7-({[7-sulfo-5-(3-sulfopropoxy)(2-naphthyl)]amino}carbonylamino)naphthalene-2-sulfonic acid |
| 103 | 3-{methyl[(7-{[(7-{[methyl(3-sulfophenyl)amino]sulfonyl}(2-naphthyl))amino]carbonylamino}(2-naphthyl))sulfonyl]amino}benzenesulfonic acid |
| 104 | prop-2-enyl 2-chloro-5-({[7-({[7-({[4-chloro-3-(prop-2-enyloxycarbonyl)phenyl]prop-2-enylamino}sulfonyl)(2-naphthyl)]amino}carbonylamino)(2-naphthyl)]sulfonyl}prop-2-enylamino)benzoate |
| 105 | 5-{[(7-{[(7-{[(3-carboxy-4-chlorophenyl)prop-2-enylamino]sulfonyl}(2-naphthyl))amino]carbonylamino}(2-naphthyl))sulfonyl]prop-2-enylamino}-2-chlorobenzoic acid |
| 112 | 4-methylphenyl 3-{[7-({[7-(N-{3-[(4-methylphenyl)oxysulfonyl]phenyl}carbamoyl)-2-naphthyl]amino}carbonylamino)-2-naphthyl]carbonylamino}benzenesulfonate |
| 113 | methyl 3-[(7-{[(7-{N-[3-(methoxycarbonyl)phenyl]carbamoyl}-2-naphthyl)amino]carbonylamino}-2-naphthyl)carbonylamino]benzoate |
| 114 | 3-({7-[({7-[N-(3-sulfophenyl)carbamoyl]-2-naphthyl}amino)carbonylamino]-2-naphthyl}carbonylamino)benzenesulfonic acid |
| 116 | 3-({7-[({7-[N-(3-carboxyphenyl)carbamoyl]-2-naphthyl}amino)carbonylamino]-2-naphthyl}carbonylamino)benzoic acid |
| 122 | 5-[({7-[3-(7-{[(3-carboxy-4-hydroxyphenyl)amino]sulfonyl}(2-naphthyl))-2-oxoimidazolidinyl](2-naphthyl)}sulfonyl)amino]-2-hydroxybenzoic acid |
| 123 | 5-[({7-[3-(7-{[(3-carboxy-4-chlorophenyl)amino]sulfonyl}(2-naphthyl))-2-oxoimidazolidinyl](2-naphthyl)}sulfonyl)amino]-2-chlorobenzoic acid |
| 129 | 3-{[(7-{[N-(7-{[(3-carboxyphenyl)sulfonyl]amino}-2-naphthyl)carbamoyl]amino)-2-naphthyl)amino]sulfonyl}benzoic acid |
| 136 | 3-[({7-[({[7-({[4-chloro-3-(methoxycarbonyl)phenyl]amino}sulfonyl)(2-naphthyl)]amino}thioxomethyl)amino]-4-hydroxy-2-naphthyl}sulfonyl)amino]benzenesulfonic acid |
| 137 | 2-chloro-5-({[7-({[7-{[(5-hydroxy-7-{[(3-sulfophenyl)amino]sulfonyl}(2-naphthyl))amino]thioxomethyl}amino)(2-naphthyl)]sulfonyl}amino)benzoic acid |
| 138 | 2-chloro-5-{[(7-{[N-(5-hydroxy-7-{[(3-sulfophenyl)amino]sulfonyl}(2-naphthyl))carbamoyl]amino}(2-naphthyl))sulfonyl]amino}benzoic acid |
| 139 | methyl 2-chloro-5-[({7-[({[7-({[4-(methoxycarbonyl)phenyl]amino}sulfonyl)(2-naphthyl)]amino}thioxomethyl)amino](2-naphthyl)}sulfonyl)amino]benzoate |
| 140 | 5-({[7-({[(7-{[(4-carboxyphenyl)amino]sulfonyl}(2-naphthyl))amino]thioxomethyl}amino)(2-naphthyl)]sulfonyl}amino)-2-chlorobenzoic acid |
| 141 | 5-{[(7-{[N-(7-{[(4-carboxyphenyl)amino]sulfonyl}(2-naphthyl))carbamoyl]amino}(2-naphthyl))sulfonyl]amino}-2-chlorobenzoic acid |

TABLE 10-continued

| Compound # | IUPAC Name |
|---|---|
| 142 | methyl 2-chloro-5-[({7-[({[7-({[3-(methoxycarbonyl)phenyl]amino}sulfonyl)(2-naphthyl)]amino}thioxomethyl)amino](2-naphthyl)}sulfonyl)amino]benzoate |
| 143 | 5-({[7-({[(7-{[(3-carboxyphenyl)amino]sulfonyl}(2-naphthyl))amino]thioxomethyl}amino)(2-naphthyl)]sulfonyl}amino)-2-chlorobenzoic acid |
| 144 | 5-{[(7-{[(7-{[(3-carboxyphenyl)amino]sulfonyl}(2-naphthyl))carbamoyl]amino)(2-naphthyl))sulfonyl]amino}-2-chlorobenzoic acid |
| 145 | methyl 2-chloro-5-({[7-({[(7-{[(3-sulfamoylphenyl)amino]sulfonyl}(2-naphthyl))amino]thioxomethyl}amino)(2-naphthyl)]sulfonyl}amino)benzoate |
| 146 | 2-chloro-5-({[7-({[(7-{[(3-sulfamoylphenyl)amino]sulfonyl}(2-naphthyl))amino]thioxomethyl}amino)(2-naphthyl)]sulfonyl}amino)benzoic acid |
| 147 | 2-chloro-5-{[(7-{[N-(7-{[(3-sulfamoylphenyl)amino]sulfonyl}(2-naphthyl))carbamoyl]amino}(2-naphthyl))sulfonyl]amino}benzoic acid |
| 148 | methyl 2-chloro-5-({[7-({[(5-hydroxy-7-{[(3-sulfamoylphenyl)amino]sulfonyl}(2-naphthyl))amino]thioxomethyl}amino)(2-naphthyl)]sulfonyl}amino)benzoate |
| 149 | 2-chloro-5-({[7-({[(5-hydroxy-7-{[(3-sulfamoylphenyl)amino]sulfonyl}(2-naphthyl))amino]thioxomethyl}amino)(2-naphthyl)]sulfonyl}amino)benzoic acid |
| 150 | 2-chloro 5-{[(7-{[N-(5-hydroxy-7-{[(3-sulfamoylphenyl)amino]sulfonyl}(2-naphthyl))carbamoyl]amino}(2-naphthyl))sulfonyl]amino}benzoic acid |
| 151 | methyl 2-chloro-5-{[(7-{[({7-[(3-pyridylamino)sulfonyl](2-naphthyl)}amino)thioxomethyl]amino}(2-naphthyl))sulfonyl]amino}benzoate |
| 152 | 2-chloro-5-{[(7-{[({7-[(3-pyridylamino)sulfonyl](2-naphthyl)}amino)thioxomethyl]amino}(2-naphthyl))sulfonyl]amino}benzoic acid |
| 153 | 2-chloro-5-[({7-[N-{7-[(3-pyridylamino)sulfonyl](2-naphthyl)}carbamoyl)amino](2-naphthyl)}sulfonyl)amino]benzoic acid |
| 154 | methyl 2-chloro-5-({[7-({[(7-{[(3-methylphenyl)amino]sulfonyl}(2-naphthyl))amino]thioxomethyl}amino)(2-naphthyl)]sulfonyl}amino)benzoate |
| 155 | 2-chloro-5-({[7-({[(7-{[(3-methylphenyl)amino]sulfonyl}(2-naphthyl))amino]thioxomethyl}amino)(2-naphthyl))sulfonyl}amino)benzoic acid |
| 156 | 2-chloro-5-{[(7-{[N-(7-{[(3-methylphenyl)amino]sulfonyl}(2-naphthyl))carbamoyl]amino}(2-naphthyl))sulfonyl]amino}benzoic acid |
| 157 | methyl 2-chloro-5-[({7-[({[7-({[4-chloro-3-(methoxycarbonyl)phenyl]amino}sulfonyl)(2-naphthyl)]amino}thioxomethyl)amino](2-naphthyl)}sulfonyl)amino]benzoate |
| 158 | methyl 5-({[7-((1Z)-1-aza-2-{[7-({[4-chloro-3-(methoxycarbonyl)phenyl]amino}sulfonyl)(2-naphthyl)]amino}-2-methylthiovinyl)(2-naphthyl)]sulfonyl}amino)-2-chlorobenzoate |
| 159 | methyl 2-chloro-5-[({7-[({[7-({[4-chloro-3-(methoxycarbonyl)phenyl]amino}sulfonyl)(2-naphthyl))amino}iminomethyl)amino](2-naphthyl)}sulfonyl)amino]benzoate |
| 160 | 5-({[7-({[(7-{[(3-carboxy-4-chlorophenyl)amino]sulfonyl}(2-naphthyl))amino]iminomethyl}amino)(2-naphthyl)]sulfonyl}amino)-2-chlorobenzoic acid |
| 161 | methyl 5-[({7-[((1E)-2-aza-1-{[7-({[4-chloro-3-methoxycarbonyl)phenyl]sulfonyl}amino)(2-naphthyl)]amino}prop-1-enyl)amino](2-naphthyl)}amino)sulfonyl]-2-chlorobenzoate |
| 162 | 5-({[7-({(1E)-2-aza-1-[(7-{[(3-carboxy-4-chlorophenyl)sulfonyl]amino}(2-naphthyl))amino]prop 1-enyl}amino)(2-naphthyl)]amino}sulfonyl)-2-chlorobenzoic acid |
| 163 | methyl 5-({[7-({(1Z)-2-aza-1-dimethylamino)-2-[7-({[4-chloro-3-(methoxycarbonyl)phenyl]sulfonyl}amino)(2-naphthyl)]vinyl}amino)(2-naphthyl)]amino}sulfonyl)-2-chlorobenzoate |
| 164 | 5-{[(7-{(1Z)-1-aza-2-(dimethylamino)-2-[(7-{[(3-carboxy-4-chlorophenyl)sulfonyl]amino}(2-naphthyl))amino]vinyl}(2-naphthyl))amino]sulfonyl}-2-chlorobenzoic acid |
| 165 | methyl 5-[((7-[((1E)-2-aza-1-{[4-chloro-3-methoxycarbonyl)phenyl]sulfonyl}amino)(2-naphthyl)]amino}-2-cyanovinyl)amino](2-naphthyl)}amino)sulfonyl]-2-chlorobenzoate |
| 166 | 5-({[7-({(1E)-2-aza-1-[(7-{[(3-carboxy-4-chlorophenyl)sulfonyl]amino}(2-naphthyl))amino]-2-cyanovinyl}amino)(2-naphthyl)]amino}sulfonyl)-2-chlorobenzoic acid |
| 167 | methyl 5-[({7-[((1E)-2-aza-1-([7-({[4-chloro-3-methoxycarbonyl)phenyl]sulfonyl}amino)(2-naphthyl)]amino}penta-1,4-dienyl)amino](2-naphthyl)}amino)sulfonyl]-2-chlorobenzoate |
| 168 | 5-({[7-({(1E)-2-aza-1-[(7-{[(3-carboxy-4-chlorophenyl)sulfonyl]amino}(2-naphthyl))amino]penta-1,4-dienyl}amino)(2-naphthyl)]amino}sulfonyl)-2-chlorobenzoic acid |
| 169 | 3-{[(6-{[(6-{[(3-sulfophenyl)amino]sulfonyl}-2-naphthyl)amino]carbonylamino}-2-naphthyl)sulfonyl]amino}benzenesulfonic acid |
| 170 | methyl 3-({[6-{[6-({[3-(methoxycarbonyl)phenyl]amino}sulfonyl-2-naphthyl]amino}carbonylamino)-2-naphthyl]sulfonyl}amino)benzoate |
| 171 | 3-{[(6-{[(6-{[(3-carboxyphenyl)amino]sulfonyl}-2-naphthyl)amino]carbonylamino)-2-naphthyl)sulfonyl]amino}benzoic acid |
| 172 | methyl 4-({[6-({[6-({[4 methoxycarbonyl)phenyl]amino}sulfonyl)-2-naphthyl]amino}carbonylamino)-2-naphthyl]sulfonyl}amino)benzoate |
| 173 | 4-{[(6-{[(6-{[(4-carboxyphenyl)amino]sulfonyl}-2-naphthyl)amino]carbonylamino}-2-naphthyl)sulfonyl]amino}benzoic acid |
| 174 | methyl 3-({[6-({N-[6-({[3,5-bis(methoxycarbonyl)phenyl]amino}sulfonyl)(2-naphthyl)]carbamoyl}amino)(2-naphthyl)]sulfonyl}amino)-5-(methoxycarbonyl)benzoate |
| 175 | 5-{[(6-{[(6-{[(3,5-dicarboxyphenyl)amino]sulfonyl}-2-naphthyl)amino]carbonylamino}-2-naphthyl)sulfonyl]amino}benzene-1,3 dicarboxylic acid |
| 176 | methyl 2,4,5-trifluoro-3-({[6-({N-[6-({[2,5,6-trifluoro-3-(methoxycarbonyl)phenyl]amino}sulfonyl)(2-naphthyl)]carbamoyl}amino)(2-naphthyl)]sulfonyl}amino)benzoate |
| 177 | 3-{[(6-{[(6-{[(3-carboxy-2,5,6-trifluorophenyl)amino]sulfonyl}(2-naphthyl))amino]carbonylamino}(2-naphthyl))sulfonyl]amino}-2,4,8-trifluorobenzoic acid |
| 178 | ethyl 2-{4-[({6-[(N-{6-[({4-[(ethoxycarbonyl)methyl]phenyl}amino)sulfonyl]-2-naphthyl}carbamoyl)amino]-2-naphthyl}sulfonyl)amino]phenyl}acetate |

TABLE 10-continued

| Compound # | IUPAC Name |
|---|---|
| 179 | 2-[4-({[6-({N-[6-({[4-(carboxymethyl)phenyl]amino}sulfonyl)-2-naphthyl]carbamoyl}amino)-2-naphthyl]sulfonyl)amino)phenyl]acetic acid |
| 180 | ethyl 1-[(6-{[(6-{[3-ethoxycarbonyl)piperidyl]sulfonyl}-2-naphthyl)amino]carbonylamino}-2-naphthyl)sulfonyl]piperidine-3-carboxylate (mixture of 2 enantiomers and one meso) |
| 181 | 1-({6-[({6-[(3-carboxypiperidyl)sulfonyl]-2-naphthyl}amino)carbonylamino]-2-naphthyl}sulfonyl)piperidine-3-carboxylic acid (mixture of 2 enantiomers and one meso) |

Example 11
$^{32}$P-cytoplasmic Kinase Domain (CKD) Autophosphorylation Assay The insulin signaling pathway is activated through stimulation of the insulin receptor. A major component of this activation is the phosphorylation of a specific portion of the receptor called the β-kinase domain. The complete β-kinase domain of the human insulin receptor (CKD) was expressed in, and purified from, baculovirus. CKD (4.0 μg/ml), in a solution of 29 mM HEPES (pH 7.6), 0.05% Triton X-100, 10 mM MgCl$_2$, 2 mM MnCl$_2$ (50 μl final volume), was combined with 50 μM ATP, and 5 μCi $^{32}$P-ATP (3000 Ci/mmol.). A test compound, or the vehicle (dimethyl sulfoxide (DMSO)) was added to a final DMSO concentration of 1%. The mixture was incubated for 10 minutes at room temperature. The reaction was terminated by the addition of 10 μl of 200 mM EDTA. A 30 μl volume was removed, mixed with 5 μl of 6×Laemmeli sodium dodecyl sulfate (SDS) treatment buffer, and heated to 94° C. for 5 minutes. A 20 μl aliquot was then run on an SDS-PAGE gel. The radioactivity incorporated into the CKD band was quantified by phosphorimaging of the gel, or scintillation counting of the excised bands. The potency of a compound for increasing phosphorylation was expressed as % of the vehicle level. The results for this are shown in Table 11, below.

TABLE 11

| Compound | % Activity vs. Control |
|---|---|
| 3 | 88 |
| 4 | 152 |
| 9 | 118 |
| 11 | 96 |
| 12 | 131 |
| 13 | 135 |
| 14 | 110 |
| 15 | 125 |
| 16 | 144 |
| 23 | 80 |
| 26 | 124 |
| 27 | 112 |
| 28 | 124 |
| 29 | 106 |
| 39 | 93 |
| 40 | 130 |
| 41 | 109 |
| 42 | 124 |
| 76 | 89 |
| 77 | 171 |
| 89 | 104 |
| 94 | 279 |
| 95 | 101 |
| 97 | 99 |
| 98 | 166 |
| 99 | 110 |
| 100 | 79 |
| 101 | 104 |
| 102 | 115 |

Example 12
Whole-cell Phosphorylation Assay

The initial step in insulin signaling is phosphorylation of the insulin receptor in response to insulin binding. NIH 3T3 cells overexpressing human insulin receptor (3T3HIR) were grown for 2 days at a density of 2×10$^5$/ml cells in 6 well culture dishes in DMEM with 10% FBS and L-glutamine. Prior to the experiment the cells were serum-starved overnight with DMEM with 0.1% BSA. The following morning, the cells were washed with PBS and the medium was replaced with 150 mM NaCl, 1.7 mM KCl, 0.9 mM CaCl$_2$, K$_2$HPO$_4$ (pH 7.4), to which were added either the experimental compounds, or their vehicle (DMSO). Insulin or its vehicle (0.01% BSA) was diluted in the assay buffer (containing test compound or vehicle, respectively) to a final concentration of 2.5 nM. After incubating for 15 min, the cells were washed with cold PBS twice and lysed in 50 mM Tris.HCl, pH 7.4 150 mM NaCl, 0.25% sodium deoxycholate, 1% NP-40, 1 mM EGTA, 1 mM PMSF, 1 mM Na$_3$VO$_4$, 1 mM NaF, 1 ug/ml each of Aprotinin, Leupeptin and Pepstatin. The cell lysates were clarified by centrifugation at 12000 rpm, and the supernatants were estimated for protein concentration. Total cell lysate (~20×g) was boiled with 2×SDS-PAGE sample buffer for 3 min and loaded into 7.5% SDS-PAGE along with Amersham rainbow marker protein as a molecular weight standard.

Figure 2:
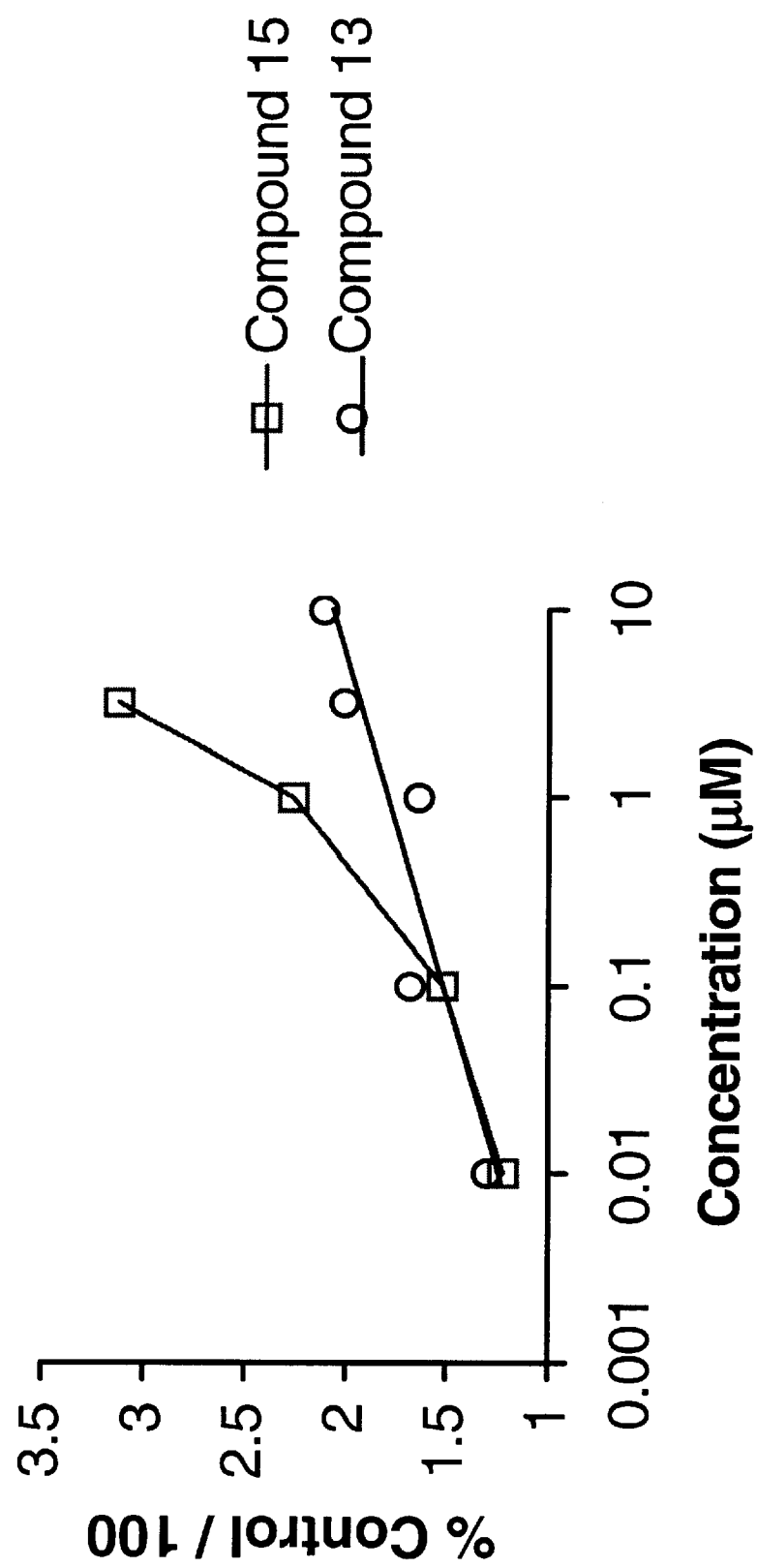
FIG. 2 shows the increase in the phosphorylation of the insulin receptor when treated with Compounds 13 and 15 at various concentrations.

After completing SDS-PAGE, the proteins were transferred onto Immobilon-P membrane and Western analysis was carried out by incubating the blot with anti-phosphotyrosine antibody and developed by Enhanced Chemiluminiscence (ECL), as Shown in FIG. 1. Shown in FIG. 2 is the increase of autophosphorylation by Compounds 13 and 15 at various concentrations.

Example 13
Glucose Transport Activity Assay

Stimulation of the insulin receptor leads to the transport of glucose from the blood into cells, thus modulating blood glucose levels. 3T3 L1 fibroblasts (ATCC) were grown in Dulbecco's modified Eagle's medium (DMEM) with 10% fetal bovine serum (FBS). The cells were plated at a density of 3×10$^4$ cells/well in 24-well plates. Two days after confluence was reached, the cells were treated for 3 days with 0.5 mM isobutylmethylxanthine (IBMX), 1 μM dexamethasone, and 1.7 μM insulin. The cells were then transferred to DMEM with 10% FBS and supplemented with 1.7 μM insulin for 2 more days. The cells were maintained in DMEM with 10% FBS for an additional 4 days. Finally the cells were sertun-starved overnight in 0.1% bovine serum albumin (BSA) in DMEM.

The following day, the medium was replaced with 150 mM NaCl, 1.7 mM KCl, 0.9 mM CaCl$_2$, K$_2$HPO$_4$ (pH 7.4) to which were added either the experimental compounds or their vehicle (DMSO). Insulin or its vehicle (0.01% BSA) was diluted in the assay buffer (containing test compound or vehicle, respectively) to final concentration of 5.6 nM. After incubation for 30 min at 37° C., 5 µCi/ml $^{14}$C-2-deoxy-D-glucose was added, and the incubation was continued for additional 30 min at 37° C. The cells were then washed 3 times with ice-cold PBS/20 mM glucose and lysed in 250 µl of lysis buffer (50 mM HEPES pH 7.6, 1% Triton X-100) for 30 min at room temperature. Radioactivity in the lysate was quantified by scintillation counting.

Figure 3:
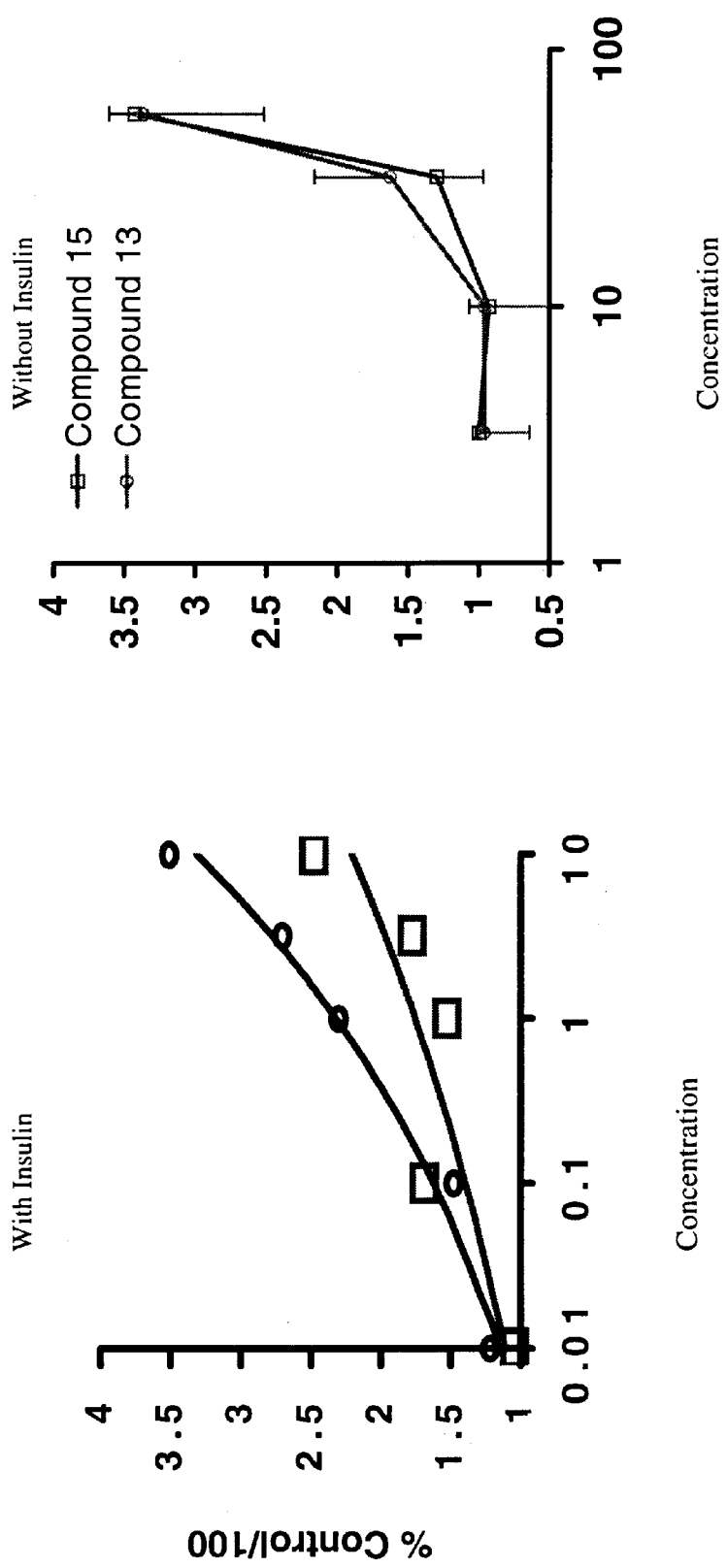
FIG. 3 shows the increase in glucose uptake of cells when treated with Compounds 13 or 15 in the presence or absence of insulin.

Once $^{14}$C-2-deoxy-D-glucose is transported into the cell, it is not released. Glucose transport is, therefore, proportional to the amount of radioactivity in the lysate. The concentration of compound necessary to produce an increase in glucose transport to greater than 150% of the vehicle control (generally representing the sum of the standard deviation of the vehicle control plus the largest standard deviation of a test sample) was recorded as the EC (effective concentration). The results are shown in Table 12. Shown in FIG. 3 is glucose uptake by cells at various concentrations when treated with Compound 13 and Compound 15.

TABLE 12

| Compound | Concentration (µM) to reach >150% activity of vehicle control |
|---|---|
| 3 | 3.2 |
| 4 | 32 |
| 13 | 3.2 |
| 15 | 3.2 |
| 16 | 32 |
| 20 | 3.2 |
| 22 | 3.2 |
| 23 | 10 |
| 25 | 3.2 |
| 26 | 32 |
| 28 | 32 |
| 29 | 3.2 |
| 30 | 3.2 |
| 31 | 3.2 |
| 32 | 32 |
| 33 | 3.2 |
| 34 | >32 |
| 35 | 32 |
| 37 | 3.2 |
| 38 | 3.2 |
| 39 | 32 |
| 40 | 3.2 |
| 41 | 32 |
| 42 | 3.2 |
| 43 | 10 |
| 45 | 3.2 |
| 47 | 3.2 |
| 48 | 3.2 |
| 49 | 3.2 |
| 50 | 3.2 |
| 51 | >32 |
| 52 | 3.2 |
| 56 | 3.2 |
| 57 | 3.2 |
| 59 | 32 |
| 60 | >32 |
| 62 | 10 |
| 64 | 3.2 |
| 65 | >32 |
| 66 | 3.2 |
| 67 | 3.2 |
| 68 | 3.2 |
| 69 | >32 |
| 71 | 3.2 |
| 72 | 3.2 |
| 73 | 10 |
| 74 | 3.2 |
| 75 | 3.2 |
| 77 | 3.2 |
| 78 | 10 |
| 79 | 10 |
| 80 | 3.2 |

TABLE 12-continued

| Compound | Concentration (µM) to reach >150% activity of vehicle control |
|---|---|
| 81 | 3.2 |
| 82 | 3.2 |
| 83 | 3.2 |
| 84 | 3.2 |
| 85 | 32 |
| 88 | >32 |
| 89 | 3.2 |
| 90 | 3.2 |
| 91 | 3.2 |
| 93 | 3.2 |
| 94 | 32 |
| 98 | 32 |
| 99 | 32 |
| 103 | 3.2 |
| 105 | >32 |
| 114 | 3.2 |
| 116 | >32 |
| 122 | 32 |
| 129 | 32 |
| 157 | >32 |
| 158 | >32 |
| 159 | 3.2 |
| 160 | 3.2 |
| 161 | >32 |
| 162 | >32 |
| 165 | 3.2 |
| 166 | 3.2 |
| 167 | >32 |
| 168 | >32 |
| 169 | 3.2 |
| 171 | 3.2 |
| 173 | 3.2 |
| 175 | 3.2 |
| 177 | >32 |
| 179 | >32 |
| 181 | 3.2 |

Example 14

Effect of Wortmannin and Cytochalasin on Glucose Uptake

Figure 4:
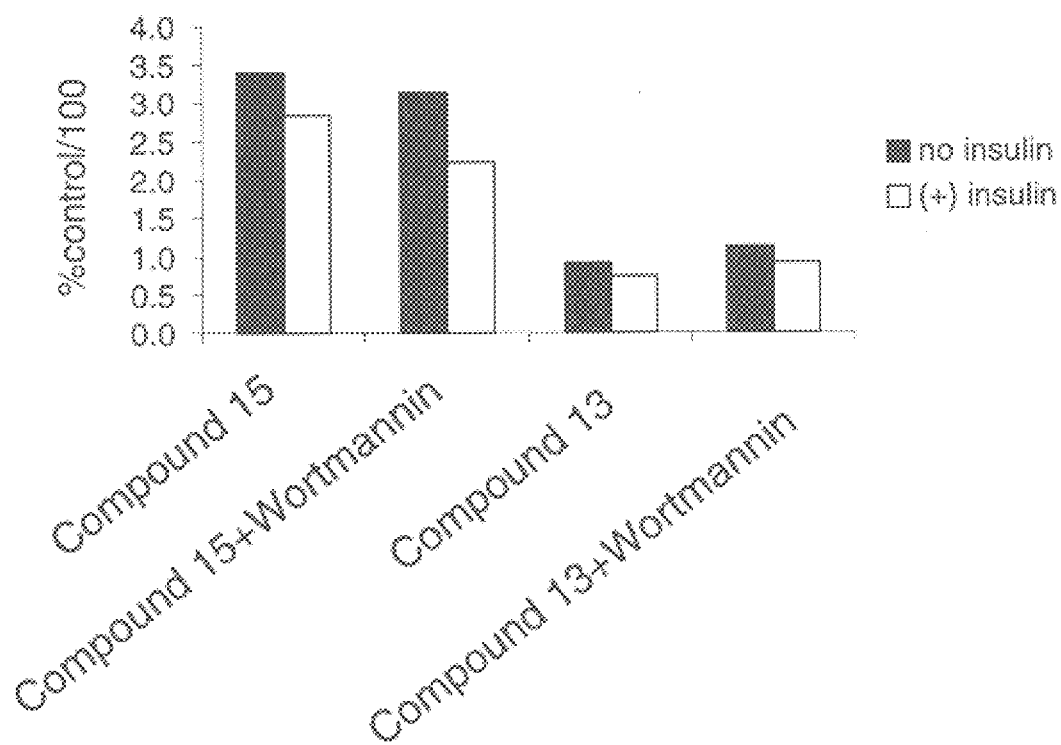
FIG. 4 shows the glucose transport effect of Compound 13 or 15 in the presence or absence of wortmannin.
Figure 5:
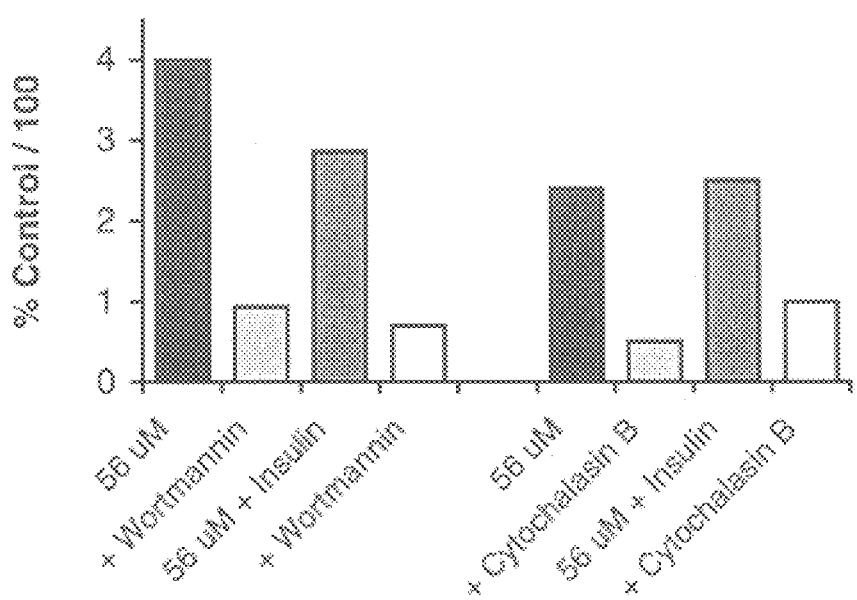
FIG. 5 shows the glucose transport effect of Compound 15 in the presence or absence of Wortmannin and Cytochalasin B.

The glucose pathway stimulated by insulin involves activation of P13 Kinase. Wortmannin is a selective inhibitor of P13 Kinase and inhibits insulin-stimulated glucose transport 3T3 L1 adipocytes were pretreated with 100 nM Wortmannin and stimulated with the compounds in the presence or absence of insulin. Wortmannin inhibited the stimulation of glucose transport, measured as in Example 11, by either Compound 15 alone or Compound 15 plus 5.6 nM insulin. Insulin-stimulated glucose transport is mediated by glucose transporter proteins. Cytochalasin B is an inhibitor of glucose transporters and inhibits insulin-stimulated glucose uptake. Like Wortmannin, Cytochalasin B (10 µM) also inhibited the stimulation of glucose transport, measured as in Example 13, by either Compound 15 alone or Compound 15 plus 5.5 Nm INSULIN. These results suggest that the activation of glucose transport by the compounds utilizes the insulin signaling machinery of the cells. Results are shown in FIGS. 4 and 5.

Example 15

Immunofluorescence Analysis of GLUT4 Mobilization in 3T3 L1 Adipocytes

Insulin-dependent transport of glucose into cells utilizes glucose transporter proteins, such as GLUT4. Stimulation with insulin causes these transporters to translocate from storage sites within the cell membrane, where they facilitate glucose entry.

3T3 L1 adipocytes were grown and differentiated as in Example 11, except that they were grown on a microscope chamber slide. The cells were serum-starved with 0.1% BSA in DMEM for 16 hrs and stimulated with 56 µM Compound 15 alone, 100 nM Insulin for 1 hr at 37° C. The cells were fixed with 3.5% paraformaldehyde for 5 min and permeabilized with 0.2% saponin in 1% BSA, TBS for 5 min followed by incubation with anti-GLUT4 antibody for 30 min at room temperature. The cells were extensively washed and incubated with FITC-conjugated secondary antibody for 30 min at room temperature. The cells were washed, air-dried and mounted with mounting medium and examined under confocal microscope (Stuart A. Ross et. al 1996, J. Biol. Chem. 271: 3328–3332.)

As shown in FIG. 6, in unstimulated cells, the GLUT4 immunofluorescence was distributed throughout the cell (FIG. 6A). Following stimulation by insulin, GLUT4 was seen primarily at the cell surface (FIG. 6B), consistent with insulin-induced translocation. Treatment of cells with Compound 15 also produced apparent translocation of GLUT4 to the cell surface (FIG. 6C), consistent with its ability to stimulate glucose transport into cells in an insulin-like manner.

Example 16
Selectivity vs. EGFR, PDGFR and IGFR

In order to determine the selectivity of these compounds for the insulin receptor, their effects on other receptors that share a similar mechanism of activation with the insulin receptor were examined. Human epidermoid carcinoma (A431) cells were plated at a density of $2\times10^5$ cells per well in 6-well dishes in DMEM with 10% FBS and L-Glutamine and allowed to grow to 75% confluence. Prior to the experiment, the cells were serum-starved overnight with DMEM with 0.1% BSA. The following morning, the cells were washed with PBS and the medium was replaced with 150 mM NaCl, 1.7 mM KCl, 0.9 mM $CaCl_2$, $K_2HPO_4$ (pH 7.4), to which was added either the experimental compound or its vehicle (DMSO). Epidermal Growth Factor (EGF) or its vehicle (0.01% BSA) was diluted in the assay buffer (containing test compound or vehicle respectively) to a final concentration of 2.5 ng/ml. After incubating for 15 min, the cells were washed with cold PBS twice and lysed in 50 mM Tris.HCl pH 7.4, 150 mM NaCl, 0.25% sodium deoxycholate, 1% NP40, 1 mM EGTA, 1 mM PMSF, 1 mM $Na_3VO_4$, 1 mM NaF, 1 ug/ml each of Aprotinin, Leupeptin and Pepstatin. The cell lysates were clarified by centrifugation at 12000 rpm, and the supernatants were estimated for protein concentration. Total cell lysate (~20 µg) was boiled with 2×SDS-PAGE sample buffer for 3 min and loaded in a 7.5% SDS-PAGE along with Amersham rainbow marker protein as a molecular weight standard.

Figure 7:
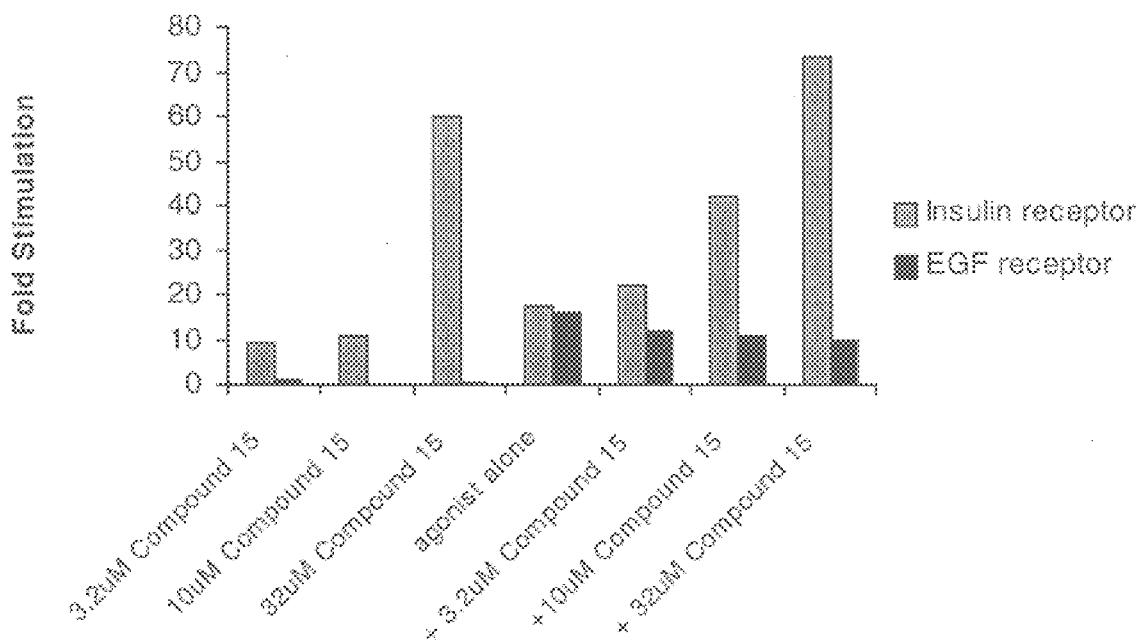
FIG. 7 shows the effect of Compound 15 against the insulin and EGF receptor.

After completing SDS-PAGE, the proteins were transferred onto Immobilon-P membrane and Western analysis was carried out by incubating the blot with anti-phosphotyrosine antibody and developed by Enhanced Chemiluminiscence (ECL). Results are shown in FIG. 7.

Compound 15 did not increase the phosphorylation of EGFR in the presence or absence of EGF. Using modifications of this protocol know to those skilled in the art, as well as the appropriate cell types, Compound 15 was likewise found not to increase the phosphorylation of the insulin-like growth factor type 1 (IGF-1) or the platelet-derived growth factor (PDGF) receptors either in the absence or presence of their endogenous ligands (1GF-1 and PDGF, respectively).

Example 17
Blood Glucose Level Determination in db/db Mouse

An accepted model for Type 2 diabetes which has been used to establish the potential anti-diabetic activity of compounds is the db/db mouse. Seven to 9 week old male db/db mice (Jackson Laboratories, Bar Harbor, Me.), were used to the study of the effects of compounds on blood glucose levels. Animals were kept in a 12 h/12 h light/dark cycle, and experiments were initiated immediately after the dark period (7:00 a.m.). Food was removed at this time and returned after the final blood glucose measurement was taken.

Insulin (0.5 U/ml, Humulin R, Catalog HI-201, Lilly, Indianapolis, Ind.) was prepared by diluting 100 U/mL stock insulin 1:200 with PBS (phosphate buffered saline, Gibco, BRL). Compounds were prepared in a vehicle of either PBS or 20% DMSO in PBS.

Five to 10 animals (average weight 40–50 g) were used in each treatment condition. The animals were injected subcutaneously with either 0.01 U insulin in PBS or PBS alone, followed by 0.1 mL of compound or its vehicle delivered intraperitoneally. Blood samples were taken 0 min, 15 min, 30 min, 1 hr, 2 hr and 4 hr after the administration of the drug or vehicle by tail bleeding. Glucose measurements were made with a Glucometer and Glucose strips (Bayer).

Figure 8:
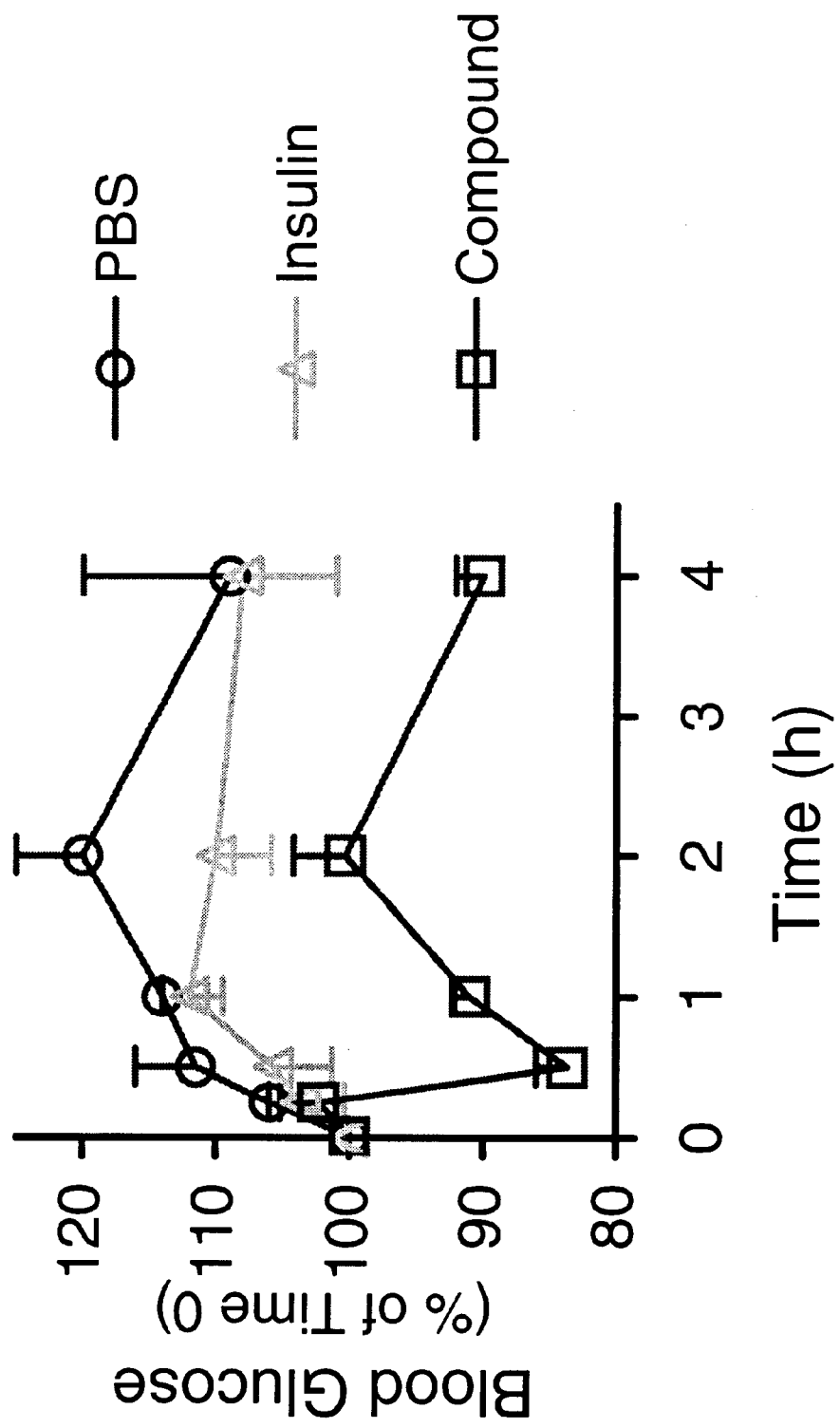
FIG. 8 shows the blood glucose lowering effect of Compound 15 with insulin in a db/db mouse.
Figure 9:
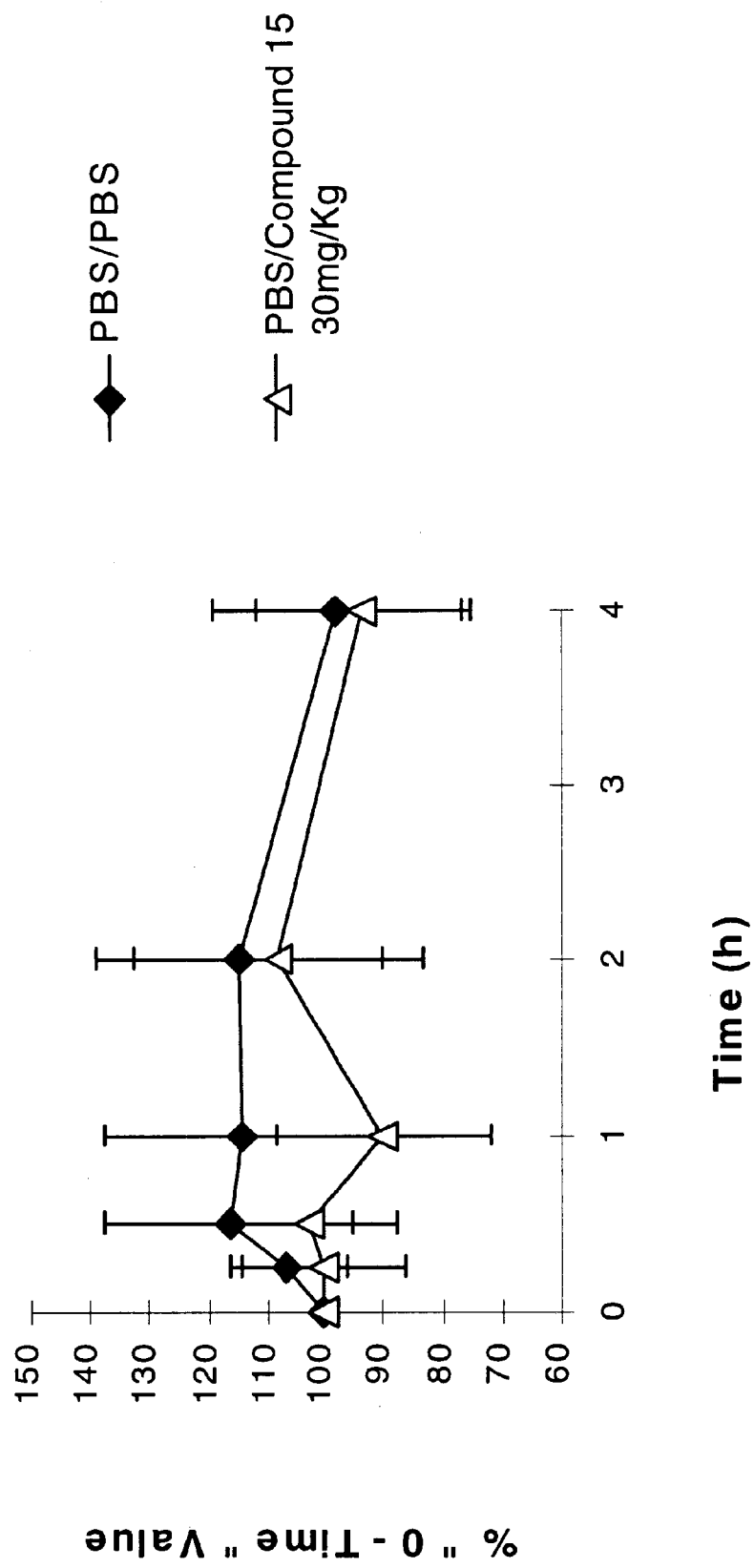
FIG. 9 shows the blood glucose lowering effect of Compound 15 only in a db/db mouse.

The resulting data are shown in FIGS. 8 and 9. In FIG. 8, blood glucose levels at various time points are shown following injections with phosphate buffered saline (PBS) only, insulin in PBS, or with compound 15 and insulin in PBS. The blood glucose levels are reported as the percentage of the "0-time" values at the time points indicated. FIG. 9 shows the effect of compound 15 alone (without added insulin) on blood glucose levels in db/db mice. Blood glucose levels at various time points are shown in FIG. 9 following injection of db/db mice with compound 15 together with its vehicle (DMSO) and insulin in PBS. Blood glucose levels at various time points following injections either with PBS alone are also shown for comparison. From the data it can be seen that compound 15 acts in an insulin-independent manner to lower blood glucose levels.

Figure 10:
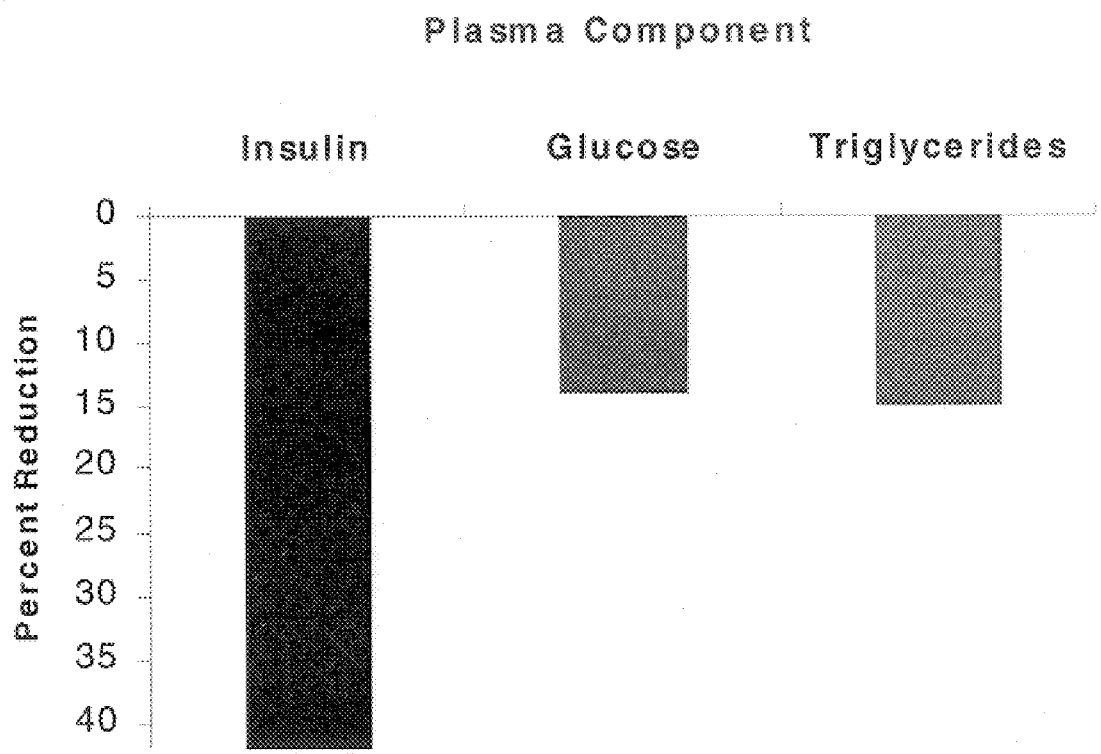
FIG. 10 shows the effect of Compound 15 on certain blood components in an ob/ob mouse.

Example 18
Lowering of Blood Glucose, Insulin and Triglycerides in the ob/ob Mouse Model of Type 2 Diabetes Another standard model of Type 2 diabetes is the ob/ob mouse. Male ob/ob mice (C57 BL/6J-ob) were housed 3–5 to a cage with free access to standard rodent chow pellets. After one week, they were given a single dose of Compound 15 (30 mg/kg, p.o.). Compound 15 produced a 13% decrease in blood glucose levels, a 42% decrease in plasma insulin levels, and a 15% decrease in plasma triglyceride levels. The concomitant reduction of plasma glucose and insulin levels are consistent with a reduction in insulin resistance. Results are shown in FIG. 10.

Example 19
Blood glucose Determination in the STZ/HFD Rat Model of Type 2 Diabetes Representative compounds were also profiled in genetically normal rats given a high-fat diet followed by treatment with a low dose of streptozotocin (STZ/HFD). This treatment regimen recreates both the insulin resistance and the hyperglycemia seen in human Type 2 diabetes. Male CD rats (Jackson Labs, Bar Harbor Me.) were maintained according to NIH guidelines, housed two per cage, and fed either standard lab chow (Tekland Laboratory Diets, James Grain, San Jose, Calif.) or the same chow supplemented with chocolate bars, cookies, and potato chips such that their final diet contained 30% fat by weight (high-fat diet; HFD). After two weeks of this diet, the animals were given an injection of freshly-prepared streptozotocin (35 mg/kg, i.p.) and continued on the HFD. Animals that achieved glucose levels of 190 to 380 mg/dl were used in this study. At the end of the 12-hour light/dark cycle, and just prior to the experiment, the animals were moved in cages with no food available until 4 hours after treatment. The compound or vehicle (PBS) was given p.o. by gavage, and blood was sampled by approved IACUC protocol using tail cap method. Glucose was determined using the Glucometer Elite (Bayer, Elkhart, Ind.).

Compound 15 produced a reduction in blood glucose levels beginning one hour after administration and persisting for the entire 6 hours of the experiment (FIG. 11). The reduction was maximal (20%) 4 hours after the administration of Compound 15. The potencies of other compounds in the model shown in Table 13.

TABLE 13

Reduction in blood glucose levels in the STZ/HFD rat model after oral compound administration (30 mg/kg). Results are shown as maximal reduction over the time at which it occurred.

| Compound Number | % Reduction in Blood Glucose/Time (h) |
|---|---|
| 41 | 20/4 |
| 13 | 20/1 |
| 29 | 18/6 |
| 48 | 24/2 |
| 93 | 25/4 |

Example 20

Rat Muscle Phosphorylation

Muscle is a partcularly important tissue for taking up glucose from the blood in response to insulin receptor stimulation. Activation of muscle insulin receptors is, therefore, an important factor in the control of blood glucose levels. STZ/HFD rats prepared as in Example 18 were given an oral dose of compound 15 (30 mg/kg), and muscle samples were harvested at different time points (0.5 hr, 1 hr, 2 hr, 3 hr, 4 hr, 6 hr) and homogenized in extraction buffer (50 mM Tris.HCl pH 7.4, 150 mM NaCl, 0.25% sodium deoxycholate, 1% NP40, 1 mM EGTA, 1 mM PMSF, 1 mM $Na_3VO_4$, 1 mM NaF, 1 ug/ml each of Aprotinin, Leupeptin and Pepstatin). The tissue homogenate was centrifuged at 12K for 30 min at 4° C., and the supernatants were saved. An equal protein amount from each sample was immunoprecipitated with anti-insulin receptor antibody for 2 hr at 4° C., followed by another 1 hr incubation with Protein G-Agarose beads. The immunecomplexes were washed three times with the extraction buffer, and the samples were boiled in 2×SDS-PAGE loading buffer for 5 min at 100° C. The samples were resolved in a 7.5% SDS-PAGE along with Amersham rainbow marker protein as a molecular weight standard.

Figure 12:
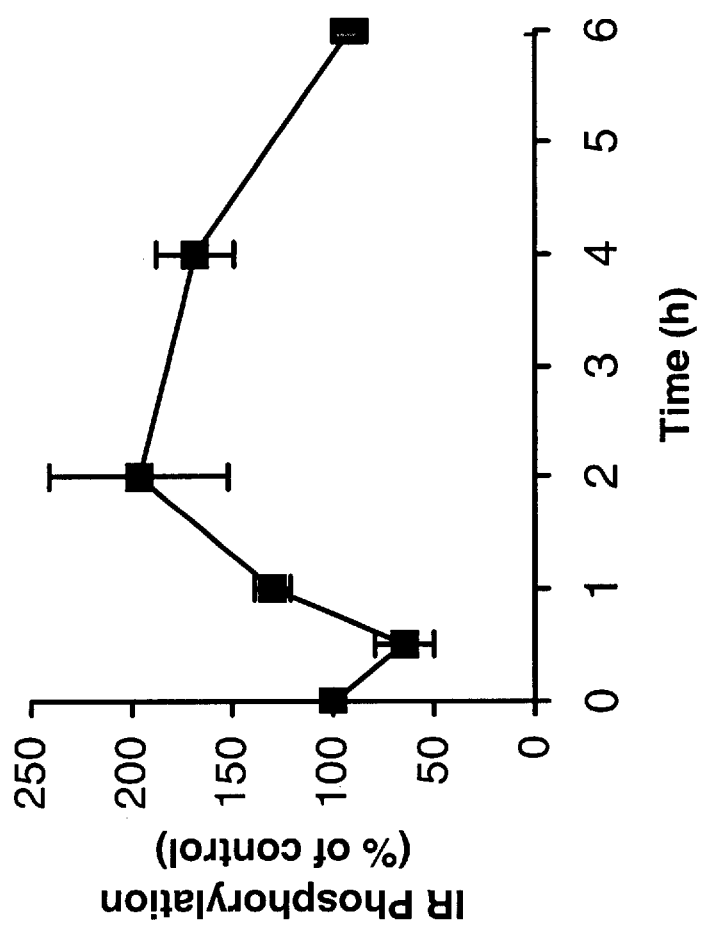
FIG. 12 shows the amount of insulin receptor phosphorylation found in muscle tissue after oral administration of Compound 15.

After completing SDS-PAGE, the proteins were transferred onto Immobilon-P membrane and Western analysis was carried out by incubating the blot with anti-phosphotyrosine antibody and developed by Enhanced Chemiluminiscence (ECL). FIG. 12 shows that Compound 15 produced an increase in phosphorylation of the insulin receptor with a time-course consistent with that of blood glucose reduction (FIG. 11).

Example 21

Multi-dosing in db/db Mice

Male db/db mice 7 to 8 weeks old (Jackson Laboratories, Bar Harbor, Maine) were given Compound 15 (56 mg/kg, p.o.) or an equivalent amount of its vehicle (PBS), as in Example 17, daily for 3 days. Blood samples were taken by an IACUC-approved protocol (tail cap method) immediately before each dose or 3 hours later. Blood glucose levels were measured using a Glucometer Elite (Bayer, Elkhart, Ind.). Blood glucose levels showed little change two hours after PBS administration (FIG. 13). In contrast, compound 15 lowered blood glucose levels 2 hours after administration on each of the 3 days by 14 to 29%.

Example 22

Multi-dosing in STZ/HFD Rats

STZ/HFD rats were prepared as in example 19. Compound 15 or an equivalent amount of the vehicle (PBS) was administered daily by the oral route at a dose of 30 mg/kg. Blood samples were taken by an IACUC-approved protocol (tail cap method) immediately before each dose and 4 and 6 (day one only) hours later. Blood glucose levels were measured using a Glucometer Elite (Bayer, Elkhart, Ind.). The blood glucose levels of the vehicle-treated group fell over the course of the experiment as the animals recovered from the low dose of STZ (FIG. 14). Compound 15 administration lowered blood glucose levels below those of the vehicle-treated group by 6 hours after administration, and this lowering was sustained throughout the remainder of the 3 days.

Example 23

Acute Toxicity

Compound 15 was administered in PBS vehicle to male db/db mice (i.p.) and male CD rats (p.o.) at 300 mg/kg; which is approximately 10 times its effective dose. No acute toxicity was seen.

Example 24

Ames Test (Compound 4)

Compound 4 was tested for its ability to cause mutations in the histidine operon of *Salmonella typhimurium* strains TA89, TA100, TA1535, and TA1537, and at the tryptophan operon of *Escherichia coli* strain WP2uvrA. These represent standard tests for the mutagenic potential of compounds and are collectively called the Ames Test. The compounds were tested at non-toxic doses (50 to 5000 µg/plate) in the absence of exogenous activation and in the presence of induced rat liver S-9 plus cofactors. Under the conditions of this study, the compounds did not induce any significant increase in the number of revertant colonies for any of the tester strains and were, therefore, judged negative in the *Salmonella typhimurium/Escherichia coli* Plate Incorporation Mutation Assay.

Example 25

P450 Interactions

A major pathway for elimination of drugs from the body, which may limit their effectiveness, is the cytochrome P450 system of the liver. Compound 15 did not inhibit the catalytic activity of the human cytochromes P450, CYPIA2, CYP2C9, CYP2CI9, CYP2D6, or CYP3A4. In addition, Compounds 15, 53, and 48 were not metabolized by rate liver microsomes after a 1-hour incubation.

Example 26

Oral Pharmaceutical Composition Preparation-solid Dosage Formulation

A pharmaceutical composition for oral administration may be prepared by combining the following:

| | % w/w |
|---|---|
| Compound of this invention | 10% |
| Magnesium stearate | 0.5% |
| Starch | 2.0% |
| HPM cellulose | 1.0% |
| Microcrystalline cellulose | 86.5% |

The mixture may be compressed to tablets, or filled into hard gelatin capsules.

The tablet may be coated by applying a suspension of film former (e.g., HPM cellulose), pigment (e.g., titanium dioxide) and plasticiser (e.g., diethyl phthalate) and drying the film by evaporation of the solvent. The film coat can comprise 2.0% to 6.0% of the tablet weight, preferably about 3.0%.

Example 27
Oral Pharmaceutical Composition Preparation-capsule

A pharmaceutical composition of a compound of the invention suitable for oral administration may also be prepared by combining the following:

| | % w/w |
|---|---|
| Compound of this invention | 20% |
| Polyethylene glycol 400 | 80% |

The medicinal compound is dispersed or dissolved in the liquid carrier, with a thickening agent added, if required. The formulation is then enclosed in a soft gelatin capsule by suitable technology.

Example 8
Pharmaceutical Composition for Parenteral Administration

A pharmaceutical composition for parenteral administration may be prepared by combining the following:

| | Preferred Level |
|---|---|
| Compound of this invention | 1.0% |
| Saline | 99.0% |

The solution is sterilized and sealed in sterile containers.

Example 28
Distribution of Compound-[14C]-15 After Oral Aministration

STZ/IFD rats, prepared as in Example 19, were given a single oral dose of 30 mg/kg compound-[14C]-15 labeled with 50 μCi of 14C prepared as in Example 11A. Two hours later the animals were euthanized and 200 mg samples of various tissues were removed by an IACUC-approved protocol. The tissue samples were homogenized and their radioactivity content was measured by scintillation counting. The highest levels of radioactivity were found in the pancreas, liver, and thigh muscle. These corresponded to Compound 15 concentrations of approximately 780 nM, 200 nM, and 175 nM, respectively. These concentrations would be sufficient to produce insulin receptor phosphorylation in vitro. Lower levels of radioactivity indicative of 50 nM to 100 nM concentrations of the compound were found in abdominal muscle, fat, kidney, and spleen. The amount of radioactivity in the blood was not above background levels.

All documents cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A compound of the formula:

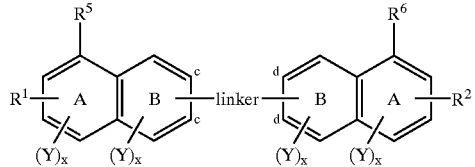

where $R^1$ and $R^2$ are substituents on the A rings and are, independently, $-SO_2NR^7_2$, $-C(O)NR^7_2$, $-NR^7SO_2R^7$, $-NR^7C(O)R^7$, $-SO_2OR^7$, $-C(O)OR^7$, $-OSO_2R^7$, or $-OC(O)R^7$, $R^3$ and $R^4$ are, independently, hydrogen or lower alkyl, or $R^3$ and $R^4$ together are $-(CH_2)_2-$, $-(CH_2)_3-$, or $-(CH_2)_4-$, $R^5$ and $R^6$ are, independently, hydrogen, alkyl, substituted alkyl, cyano, halo, nitro, $-SR^8$, $-C(O)R^8$, $-SO_2OR^8$, $-OSO_2R^8$, $-SO_2NR^8_2$, $-NR^8SO_2R^8$, $-OC(O)R^8$, $-C(O)OR^8$, $-C(O)NR^8_2$, $-NR^8C(O)R^8$, $-OR^8$, or $-NR^8_2$, each $R^7$ and $R^8$ is, independently, hydrogen, alkyl, substituted alkyl, aryl, substituted aryl, aryl(lower)alkyl, substituted aryl(lower)alkyl, heteroaryl(lower)alkyl, substituted heteroaryl(lower)alkyl, heterocyclyl, substituted heterocyclyl, heteroaryl, or substituted heteroaryl, each Y is, independently, alkyl, substituted alkyl, cyano, halo, nitro, $-SR$, $-OR$, or $-NR_2$, where each R is, independently, hydrogen, lower alkyl, or substituted lower alkyl, each x is, independently, 0, 1 or 2, and linker connects a carbon designated as c to a carbon designated as d, and is:

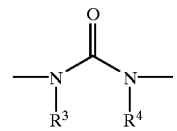

and, where, if $R^1$ and $R^2$ are both $-SO_2OH$, then:
(i) no Y is $-SO_2OH$;
(ii) neither $R^5$ nor $R^6$ is $-SO_2OR^8$ or $-OSO_2R^8$; and
(iii) $R^5$ and $R^6$ are not both selected from the group consisting of hydroxy and hydrogen unless at least one $(Y)_x$ is $(Y')_{x'}$, where x' is 1 or 2 and Y' is a halo, or a pharmaceutically acceptable salt thereof, as a single stereoisomer or mixture of stereoisomers.

2. The compound of claim 1, in which each x is 0.

3. The compound of claim 1 that is a compound of the formula:

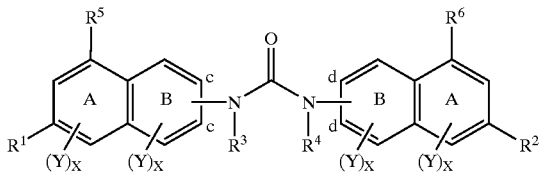

or a pharmaceutically acceptable salt thereof,
as a single stereoisomer or mixture of stereoisomers.

4. The compound of claim 1, where each Y is, independently, lower alkyl, halo-lower alkyl, lower alkyloxy, cyano, halo, thio, nitro, amino, or hydroxy.

5. The compound of claim 1, where
$R^1$ and $R^2$ are, independently, —$SO_2OR^{10}$, —$C(O)OR^{10}$, —$SO_2NR^{11}R^{10}$, —$C(O)NR^{11}R^{10}$, —$OSO_2R^{10}$, —$OC(O)R^{10}$, —$NR^{11}SO_2R^{10}$, or —$NR^{11}C(O)R^{10}$;
each $R^{10}$ is, independently, alkyl, substituted alkyl, aryl, substituted aryl, aryl(lower)alkyl, substituted aryl(lower)alkyl, heteroaryl(lower)alkyl, substituted heteroaryl(lower)alkyl, heterocyclyl, substituted heterocyclyl, heteroaryl, or substituted heteroaryl; and
each $R^{11}$ is, independently, hydrogen or lower alkyl.

6. The compound of claim 5, where $R^1$ and $R^2$ are, independently, —$SO_2NHR^{10}$ or —$NHSO_2R^{10}$.

7. The compound of claim 5, where each $R^{10}$ is, independently, aryl, heteroaryl, aryl(lower)alkyl, or heteroaryl(lower)alkyl.

8. The compound of claim 5, where
each $R^{10}$ is, independently, a substituted alkyl, substituted aryl, substituted aryl(lower)alkyl, substituted heteroaryl(lower)alkyl, substituted heterocyclyl or substituted heteroaryl;
at least one of the substituents on $R^{10}$ is $R^{12}$;
each $R^{12}$ is, independently, —$SO_2OR^{13}$, —$C(O)OR^{13}$, —$SO_2NR^{13}_2$, —$C(O)NR^{13}_2$, hydroxy, triazolyl, tetrazolyl, hydroxyisoxazolyl, a phosphonic acid residue, or a phosphonate residue; and
each $R^{13}$ is, independently, hydrogen or lower alkyl.

9. The compound of claim 8, where each $R^{10}$ is substituted aryl.

10. The compound of claim 9, where each $R^{10}$ is substituted phenyl.

11. The compound of claim 10, where each $R^{12}$ is, independently, —$C(O)OR^{13}$, —$C(O)NR^{13}_2$, hydroxy, triazolyl, tetrazolyl, hydroxyisoxazolyl, a phosphonic acid residue, or a phosphonate residue.

12. The compound of claim 10, where each $R^{12}$ is, independently, —$C(O)OR^{13}$, hydroxy, triazolyl, tetrazolyl, hydroxyisoxazolyl, or a phosphonic acid residue.

13. The compound of claim 10, where each $R^{12}$ is, independently, —$C(O)OR^{13}$.

14. The compound of claim 13, where $R^{12}$ is adjacent on the aryl, heteroaryl, or heterocyclyl ring to a further substituent.

15. The compound of claim 14, where the further substituent is selected from chloro and hydroxy.

16. The compound of claim 8, where each $R^{12}$ is independently, —$SO_2OR^{13}$ or —$SO_2NR^{13}_2$.

17. The compound of claim 16, where each $R^{12}$ is, independently, —$SO_2OR^{13}$.

18. The compound of claim 17, where $R^{12}$ is adjacent on the aryl, heteroaryl, or heterocyclyl ring to a further substituent.

19. The compound of claim 17, where the further substituent is selected from chloro and hydroxy.

20. The compound of claim 1, where
$R^1$ is —$SO_2OR^{10}$, —$C(O)OR^{10}$, —$SO_2NR^{11}R^{10}$, —$C(O)NR^{11}R_{10}$, —$OSO_2R^{10}$, —$OC(O)R^{10}$, —$NR^{11}SO_2R^{10}$, or —$NR^{11}C(O)R^{10}$;
$R^2$ is —$SO_2NR^{11}_2$, —$C(O)NR^{11}_2$, —$SO_2OR^{11}$, or —$C(O)OR^{11}$;
each $R^{10}$ is, independently, alkyl, substituted alkyl, aryl, substituted aryl, aryl(lower)alkyl, substituted aryl(lower)alkyl, heteroaryl(lower)alkyl, substituted heteroaryl(lower)alkyl, heterocyclyl, substituted heterocyclyl, heteroaryl, or substituted heteroaryl; and
each $R^{11}$ is, independently, hydrogen or lower alkyl.

21. The compound of claim 1, where
$R^1$ and $R^2$ are, independently, —$C(O)OR^7$ or —$C(O)NR^7_2$; and
each $R^7$ is, independently, hydrogen or lower alkyl.

22. The compound of claim 1, where
$R^1$ and $R^2$ are, independently, —$SO_2OR^7$ or —$SO_2NR^7_2$; and
each $R^7$ is, independently, hydrogen or lower alkyl.

23. The compound of claim 21, where $R^1$ and $R^2$ are —$SO_2OH$.

24. The compound of claim 1, where
$R^5$ and $R^6$ are, independently, hydrogen, alkyl, substituted alkyl, cyano, halo, nitro, —$SR^8$, —$OR^8$, or —$NR^8_2$; and
each $R^8$ is, independently, hydrogen, lower alkyl, substituted lower alkyl, aryl, substituted aryl, aryl(lower)alkyl, substituted aryl(lower)alkyl, heteroaryl, substituted heteroaryl, heteroaryl(lower)alkyl, or substituted heteroaryl(lower)alkyl.

25. The compound of claim 24, where $R^5$ and $R^6$ are, independently, hydrogen, lower alkyl, halo-lower alkyl, lower alkyloxy, cyano, halo, thio, amino, nitro or hydroxy.

26. The compound of claim 1 which is symmetrical.

27. The compound of claim 1 that is selected from the group consisting of:

3-{[(7-{[N-(7-{[(3-sulfophenyl)amino]sulfonyl}-(2-naphthyl))carbamoyl]amino}-2-naphthyl)-sulfonyl]amino}benzenesulfonic acid, 3-{[(4-hydroxy-7-{[N-(5-hydroxy-7-{[(3-sulfophenyl)-amino]sulfonyl}-(2-naphthyl))carbamoyl]amino}-2-naphthyl)sulfonyl]amino}benzenesulfonic acid, 4-{[(7-{[(7-{[(4-sulfophenyl)amino]sulfonyl}-2-naphthyl)amino]carbonylamino}-2-naphthyl)sulfonyl]amino}benzenesulfonic acid, methyl 4-({[7-({N-[7-({[4-(methoxycarbonyl)phenyl]amino}sulfonyl)-2-naphthyl]-carbamoyl}amino)-2-naphthyl]sulfonyl}amino)benzoate, 4-{[(7-{[(7-{[(4-carboxyphenyl)amino]sulfonyl}-2-naphthyl)amino]carbonylamino}-2-naphthyl)-sulfonyl]amino}benzoic acid, methyl 4-({[4-hydroxy-7-({N-[5-hydroxy-7-({[4-(methoxycarbonyl)phenyl]amino}sulfonyl)(2-naphthyl)]carbamoyl}amino)-2-naphthyl]sulfonyl}amino)benzoate, 4-{[(7-{[(7-{[(4-carboxyphenyl)amino]sulfonyl}-5-hydroxy-(2-naphthyl))amino]carbonylamino}-4-hydroxy-2-naphthyl)sulfonyl]-amino}benzoic acid, 3-{[(7-{[N-(7-{[(3-carboxy-2-hydroxyphenyl)amino]sulfonyl}-(2-naphthyl))carbamoyl]-amino}(2-naphthyl))sulfonyl]amino}-2-hydroxybenzoic acid, 5-{[(7-{[N-(7-{[(3-carboxy-4-hydroxyphenyl)-amino]sulfonyl}-(2-naphthyl))carbamoyl]amino}(2-naphthyl))sulfonyl]amino}-2-hydroxybenzoic acid, methyl 3-({[7-({[7-({[3-(methoxycarbonyl)-phenyl]amino}sulfonyl)-2-naphthyl]amino}carbonylamino)-2-naphthyl]sulfonyl}amino)benzoate, 3-{[(7-{[(7-{[(3-carboxyphenyl)amino]sulfonyl}-2-naphthyl)amino]carbonylamino}-2-naphthyl)sulfonyl]amino}benzoic acid, methyl 3-({[4-hydroxy-7-({[5-hydroxy-7-({[3-(methoxycarbonyl)phenyl]amino}sulfonyl)(2-naphthyl)amino}carbonylamino)-2-naphthyl]sulfonyl}amino)benzoate, 3-{[(7-{[(7-{[(3-carboxyphenyl)-amino]sulfonyl}-5-hydroxy-(2-naphthyl))amino]carbonylamino}-4-hydroxy-2-naphthyl)-sulfonyl]amino}benzoic acid, 5-{[(7-{[N-(7-{[(3-carboxy-4-hydroxyphenyl)-amino]sulfonyl}-5-hydroxy(2-naphthyl))carbamoyl]amino}-4-hydroxy(2-naphthyl))sulfonyl]amino}-2-hydroxybenzoic acid, 5-{[(7-{[N-(7-{[(3-carboxy-4-chlorophenyl)amino]sulfonyl}-(2-naphthyl))carbamoyl]amino}(2-naphthyl))sulfonyl]-amino}-2-chlorobenzoic acid, 5-{[(7-{[N-(7-{[(3-carboxy-4-chlorophenyl)-amino]sulfonyl}-5-hydroxy(2-naphthyl))carbamoyl]amino}-4-hydroxy(2-naphthyl))sulfonyl]amino}-2-chlorobenzoic acid, methyl 2-hydroxy-5-({[7-({[7-({[4-hydroxy-3-(methoxycarbonyl)phenyl]amino}sulfonyl)(2-naphthyl)]amino}carbonylamino)-(2-naphthyl)]sulfonyl}amino)benzoate, methyl 2-chloro-5-({[7-({N-[7-({[4-chloro-3-(methoxycarbonyl)phenyl]amino}sulfonyl)(2-naphthyl)]carbamoyl}amino)(2-naphthyl)]sulfonyl}amino)benzoate, N-(7-{[(3-(1H-1,2,3,4-tetraazol-5-yl)phenyl)amino]sulfonyl}-(2-naphthyl))-[(7-{[(3-(1H-1,2,3,4-tetraazol-5-yl)phenyl)amino]sulfonyl}(2-naphthyl))amino]carboxamide, N-(5-hydroxy-7-{[(3-(1H-1,2,3,4-tetraazol-5-yl)phenyl)amino]sulfonyl}(2-naphthyl))[(5-hydroxy-7-{[(3-(1H-1,2,3,4-tetraazol-5-yl)phenyl)amino]sulfonyl}(2-naphthyl))amino]-carboxamide, N-[7-({[3-(diethoxyphosphoryl)-phenyl]amino}sulfonyl)-(2-naphthyl)]{[7-({[3-(diethoxyphosphoryl)phenyl]amino}sulfonyl)-(2-naphthyl)]amino}carboxamide, N-[7-({[3-(ethoxy(hydroxyphosphoryl))-phenyl]amino}sulfonyl)-(2-naphthyl)]-{[7-({[3-(ethoxy(hydroxyphosphoryl))-phenyl]amino}sulfonyl)(2-naphthyl)]amino}carboxamide, 2-chloro-5-{[(7-{[(7-{[(4-chloro-3-sulfophenyl)amino]sulfonyl}-2-naphthyl))amino]-carbonylamino}(2-naphthyl))sulfonyl]amino}-benzenesulfonic acid, 2-chloro-5-{[(7-{[(7-{[(4-chloro-3-sulfophenyl)amino]sulfonyl}-5-hydroxy(2-naphthyl))amino]-carbonylamino}-4-hydroxy-(2-naphthyl))sulfonyl]amino}benzenesulfonic acid, 5-[({7-[3-(7-{[(3-carboxy-4-hydroxyphenyl)amino]sulfonyl}-(2-naphthyl))-2-oxoimidazolidinyl](2-naphthyl)}sulfonyl)amino]-2-hydroxybenzoic acid, 5-[({7-[3-(7-{[(3-carboxy-4-chlorophenyl)-amino]sulfonyl}-(2-naphthyl))-2-oxoimidazolidinyl](2-naphthyl)}-sulfonyl)amino]-2-chlorobenzoic acid, 2-chloro-5-{[(7-{[N-(5-hydroxy-7-{[(3-sulfophenyl)amino]sulfonyl}(2-naphthyl))carbamoyl]amino}(2-naphthyl))sulfonyl]-amino}benzoic acid, 5-{[(7-{[N-(7-{[(4-carboxyphenyl)amino]sulfonyl}(2-naphthyl))carbamoyl]amino}(2-naphthyl))sulfonyl]amino}-2-chlorobenzoic acid;

5-{[(7-{[N-(7-{[(3-carboxyphenyl)amino]sulfonyl}(2-naphthyl))-carbamoyl]amino}(2-naphthyl))sulfonyl]amino}-2-chlorobenzoic acid, and the pharmaceutically acceptable salts thereof.

28. A pharmaceutical composition for treating a mammalian disease state selected from the group consisting of hyperglycemia, type I diabetes, and type II diabetes, comprising:

(a) a therapeutically effective amount of a compound of claim 1; and (b) at least one pharmaceutically acceptable excipient.

29. A method of stimulating the kinase activity of the insulin receptor, comprising contacting the insulin receptor, or the kinase portion thereof, with a compound of claim 1 in an amount sufficient to stimulate the kinase activity of the insulin receptor.

30. A method of activating the insulin receptor, comprising contacting the insulin receptor, or the kinase portion thereof, with a compound of claim 1, in an amount sufficient to activate the insulin receptor.

31. A method of stimulating the uptake of glucose into cells displaying the insulin receptor, comprising contacting the cells with a compound of claim 1 in an amount sufficient to stimulate the uptake of glucose into the cells.

32. A method of treating a disease state in a mammal selected from the group consisting of hyperglycemia, type I diabetes, and type II diabetes, comprising administering a therapeutically effective amount of a compound of claim 1, or a pharmaceutical composition thereof, to the mammal.

33. The method of claim 32, further comprising treating said mammal with an additional form of therapy for said disease state.

34. The radiolabeled compound of claim 1.

35. The compound of claim 34 that is $^{14}$C-4-methylphenyl-3-[({4-hydroxy-7-[(N-{5-hydroxy-7-[({3-[(4-methylphenyl)oxysulfonyl]phenyl}amino)sulfonyl](2-naphthyl)}carbamoyl)amino]2-naphthyl}sulfonyl)amino]benzenesulfonate.

36. A method of identifying a compound that has the function of stimulating the kinase activity of the insulin receptor, activating the insulin receptor, and stimulating the uptake of glucose, comprising using the compound of claim 35 as a diagnostic.

37. A process for preparing a compound which mimics the function of the compound of claim 1, comprising:

(i) submitting a test compound to a screen for determining its stimulation of the kinase activity of the insulin receptor in relation to a compound of claim 1; and (ii) preparing the test compound if it exhibits stimulation of the kinase activity of the insulin receptor.

* * * * *